(12) United States Patent
Brinch-Pedersen et al.

(10) Patent No.: US 9,540,633 B2
(45) Date of Patent: Jan. 10, 2017

(54) HIGH EXPRESSION CEREAL PHYTASE GENE

(75) Inventors: Henrik Brinch-Pedersen, Skælskør (DK); Claus K Madsen, Ringsted (DK); Giuseppe Dionisio, Slagelse (DK); Preben Bach Holm, Valby (DK)

(73) Assignee: AARHUS UNIVERSITET, Aarhus C (DK)

( * ) Notice: Subject to any disclaimer, the term of this patent is extended or adjusted under 35 U.S.C. 154(b) by 346 days.

(21) Appl. No.: 14/110,763

(22) PCT Filed: Apr. 25, 2012

(86) PCT No.: PCT/EP2012/057515
§ 371 (c)(1),
(2), (4) Date: Jan. 23, 2014

(87) PCT Pub. No.: WO2012/146597
PCT Pub. Date: Nov. 1, 2012

(65) Prior Publication Data
US 2014/0259211 A1 Sep. 11, 2014

Related U.S. Application Data
(60) Provisional application No. 61/479,689, filed on Apr. 27, 2011.

(30) Foreign Application Priority Data
Apr. 27, 2011 (EP) .................................... 11163875

(51) Int. Cl.
| | |
|---|---|
| C12N 15/01 | (2006.01) |
| A01H 1/06 | (2006.01) |
| A01H 5/10 | (2006.01) |
| C12N 9/16 | (2006.01) |
| C12N 15/82 | (2006.01) |
| C12Q 1/68 | (2006.01) |

(52) U.S. Cl.
CPC ............... *C12N 15/01* (2013.01); *A01H 5/10* (2013.01); *C12N 9/16* (2013.01); *C12N 15/8234* (2013.01); *C12N 15/8243* (2013.01); *C12Q 1/6895* (2013.01); *C12Y 301/03026* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 7,214,786 B2 * | 5/2007 | Kovalic | ............... | C07K 14/415 530/324 |
| 2008/0311659 A1* | 12/2008 | Huynh | ............... | C12N 15/8218 435/375 |
| 2010/0186127 A1 | 7/2010 | Byrum et al. | | |

FOREIGN PATENT DOCUMENTS

| | | |
|---|---|---|
| WO | 01/83763 | 11/2001 |
| WO | WO 01/83763 A2 * | 11/2001 |
| WO | 2009091518 A2 | 7/2009 |

OTHER PUBLICATIONS

Sequence 8 from Patent WO0183763, Gen Bank Accession No. AX298209.1.*
Keskin et al., 2004, Protein Science 13: 1043-1055.*
Guo et al., 2004, Proceedings of the National Academy of Sciences USA 101: 9205-9210.*
Thornton et al., 2000, Nature Structural Biology, structural genomic supplement, Nov. 2000: 991-994.*
Clark et al., 2006, Nature Genetics 38: 594-597.*
"Accession No. NGB10901" SESTO data portal, May 30, 2001, XP000002658140, retrieved from the Internet: URL:http://nordgen.org/index.php/en/content/view/full/344 (retrieved on Sep. 2, 2011).
Baumlein, H., Nagy I., et al (1992) Cis-analysis of a seed protein gene promoter: the conservative RY repeat CATGCATG within the legumin box is essential for tissue-specific expression of a legumin gene, Plant Journal 2: 233-239.
Blackwell, T.K., Bowerman, B., et al., (1994) Formation of a monomeric DNA binding domain by Skn-1 bZIP and homeodomain elements, Science 266: 621-628.
Brinch-Pedersen, H. Galili, F., Knudsen, S., & Holm, P.B., (1996) Engineering of the aspartate family biosynthetic pathway in barley (*Hordeum vulgare* L.) by transformation with heterologous genes encoding feed-back-insensitive aspartate kinase and dihydrodipicolinate synthase, Plant Molecular Biology, 32(4), 611-620.
Brinch-Pedersen et al., (2002) Engineering crop plants: getting a handle on phosphate, Trends in Plant Science, vol. 7, No. 3, Mar. 2002, 118-125.
Database EmbL—Apr. 19, 2011 "Hordeum vulfare cv. Igri PAPhy_a gene for pruple acid phosphatase isoform a," XP 00000268141, retrieved from EBI accession No. EM_PL:FR851293, Database accession No. FR851293.
Database EmbL (Online) May 18, 2011, "Secale cereale cultivar Picasso clone ScPCRG1 PAPhy_a1 gene, complete cds," XP0000026858143, retrieved from EBI accession No. EM_PL: JF838319, Database accession No. JF838319, "sequence".
Database EmbL (Online) May 18, 2011, "Secale cereale cultivar Picasso clone Sc2G1 PAPhy_a1 gene, partial cds," XP0000026858144, retrieved from EBI accession No. EM_PL: JF838320, Database accesison No. JF838320, "sequence".
Database EMBL, May 18, 2011, "Triticum monococcum cultivar NGB10901 PAPhy_a1 gene, complete cds," XP0000026858142, retrieved from EBI accession No. EM_PL: JF838315, Database accesison No. JF838315.
Depater S., Katagirl, et al (1994) bZIP proteins bind to a palindromic sequence without an ACGT core located in a seed-specific element of the pea lectin promoter, Plant Journal 6: 133-140.
Dvorakova, 1998, Phystase: Sources, Preparation and Exploitation, Folia Microbiol. 43 (4), 323-338.

(Continued)

*Primary Examiner* — David T Fox
*Assistant Examiner* — Bratislav Stankovic
(74) *Attorney, Agent, or Firm* — McKee, Voorhees & Sease, PLC

(57) ABSTRACT

The present invention provides mutant cereal plants and mature grain thereof, characterised by enhanced levels of the enzyme phytase in the grain, and methods for inducing, detecting and selecting the mutant cereal plants. The invention further relates to animal feed comprising said grain having enhanced amounts of phytase.

4 Claims, 11 Drawing Sheets

(56) References Cited

OTHER PUBLICATIONS

Figure 1:
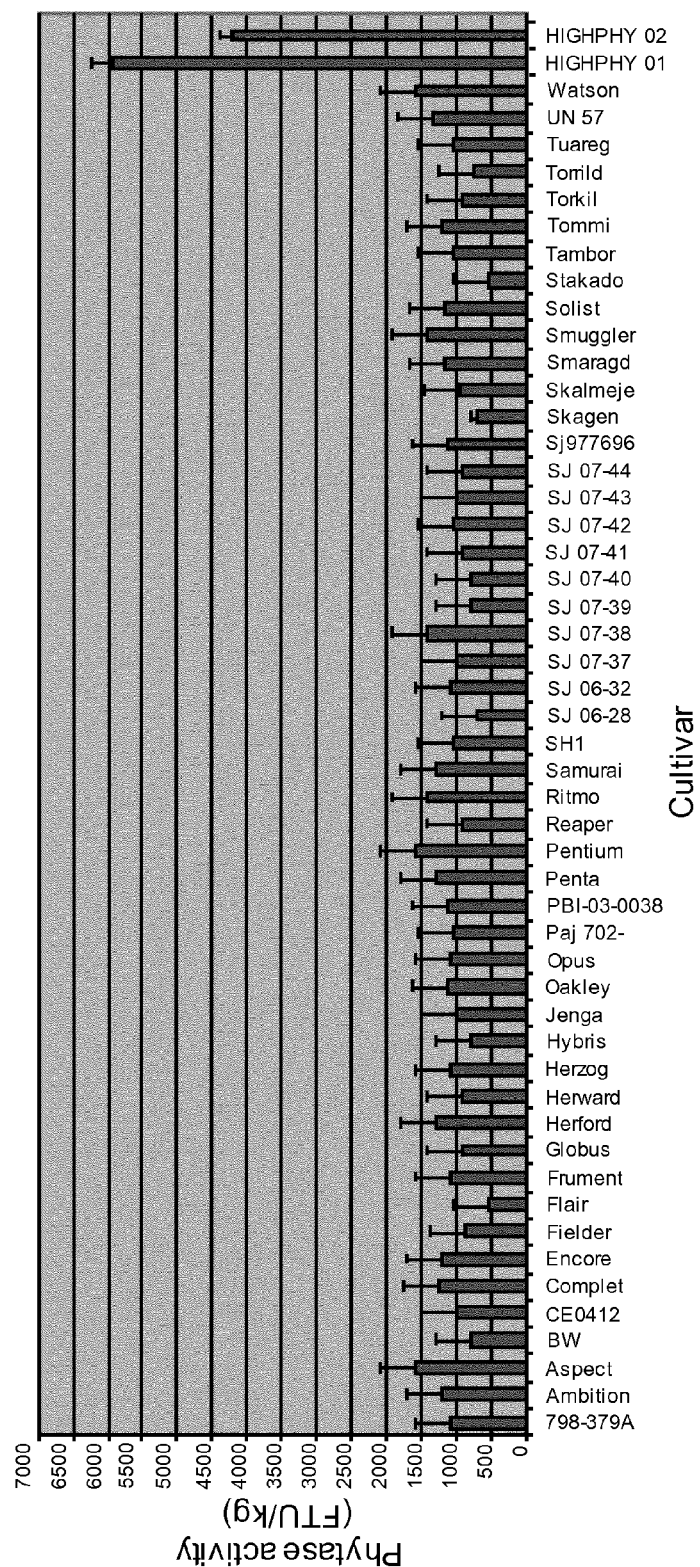

Eeckhout W., Depaepe M (1994) Total phosphorus, phytate-phosphorus and phytase activity in plant feedstuffs, Anim. Feed Sci Tech 47: 19-29.

Engelen, A.J., Vanderheeft, Randsorp, et al (1994, Simple and Rapid-Determination of Phystase Activity, Journal of Aoac international, 77(3), 760-764.

Fujiwaraa, T. Mabara E., et al (2002) Storage Proteins. The arabidopsis Book, 2002 American Scoiety of Plant Biologists.

G. Dionisio et al, "Cloning and Characterization of Purple Acid Phosphatase Phytases from Wheat, Barley, Maize, and Rice," Plant Physiology, vol. 156, No. 3, Jan. 10, 2011, pp. 1087-1100, XP55006061.

Mixed, Mutated and Random Nucleotide Sequences, Retrieved from Internet on Jan. 10, 2014, URL: http://molbio.ru/eng/scripts/01_16.html.

Jeffersen, R.A., Kavanagh, T.A., & Bevan, M. W. (1987) GUS fusions: beta-glucuronidase as a sensitive and versatile gene fusion marker in higher plants, Embo Journal 6(13), 3901-3907.

Kimber, G., * Sears, E.G. (1979) Use of wheat aneuploids, Basic Life Sciences, 13, 427.

Lott, 1984, Accumulation of Seed Reserves of Phosphorus and Other Minerals, Mineral Reserves, Seed Physiology, vol. 1, pp. 139-166.

Olsen, O., et al. Sodium azide mutagenesis: Preferential generation of AT -> GC transitions in the barley Ant18 gene, Proc. Natl. Acad. Sci USA (1993) vol. 90, pp. 8043-8047.

PlantCARE, a database of plant cis-acting regulatory elements and a portal to tools for in silico analysis of promoter sequences: Magali Lescot, Patrice Déhais, Gert Thijs, Kathleen Marchal, Yves Moreau, Yves Van de Peer, Pierre Rouzéand Stephane Rombauts, Nucleic Acids Res., Jan. 1, 2002; 30(1): 325-327.

Rasmussen et al, 2007, Transitions from Nonliving to Living Matter, Science, vol. 303, Feb. 13, 2004, pp. 963-965.

Veintraub, I. A. &Lapteva, N.A. (1988) Colorimetric determination of phytate in unpurified extracts of seeds and the products of their processing, Analytical Biochemistry 175(1), 227-23, dio:10. 1016/0003-2697(88)90382-x.

Wittwer, C. T., et al., (2003) High resolution genotyping by amplicon melting analysis using LCgreen Clinical Chemistry: 49:6 853-860.

Wu CY, Suzuki A, et al., ( 1998) The GCN4 motif in a rice glutelin gene is essential for endosperm-specific gene expression and is activated by Opaque-2 in transgenic rice plants. Plant Journal 14: 673-683.

Zhu, B. G., Cai, G. F., Hall, E. 0., & Freemen, G. J. (2007X. In-Fusion (TM) assembly: seamless engineering of multidomain fusion proteins. modular vectors, and mutations. Biotechniques, 43(3), 356-359. doi: 10.2144/000112536.

* cited by examiner

Figure 4.

| | 1 | 2 | 3 | 4 | 5 | 6 | 7 | 8 | 9 | 10 |
|---|---|---|---|---|---|---|---|---|---|---|
| 1 TaG2 lambda clone, Skagen cultivar | | 0 | 0 | 0 | 2 | 0 | 1 | 1 | 19 | 21 |
| 2 Skagen PCR clone | 100,00 | | 0 | 0 | 2 | 0 | 1 | 1 | 19 | 21 |
| 3 Bob White PCR clone | 100,00 | 100,00 | | 0 | 2 | 0 | 1 | 1 | 19 | 21 |
| 4 Pentium PCR clone | 100,00 | 100,00 | 100,00 | | 2 | 0 | 1 | 1 | 19 | 21 |
| 5 Flair PCR clone | 99,80 | 99,80 | 99,80 | 99,80 | | 2 | 3 | 3 | 21 | 23 |
| 6 Landrace 01 PCR clone | 100,00 | 100,00 | 100,00 | 100,00 | 99,80 | | 1 | 1 | 19 | 21 |
| 7 Landrace 02 PCR clone | 99,90 | 99,90 | 99,90 | 99,90 | 99,70 | 99,90 | | 2 | 20 | 22 |
| 8 Spelt PCR clone | 99,90 | 99,90 | 99,90 | 99,90 | 99,70 | 99,90 | 99,80 | | 20 | 22 |
| 9 HighPhy 01 PCR clone | 98,10 | 98,10 | 98,10 | 98,10 | 97,90 | 98,10 | 98,00 | 98,01 | | 2 |
| 10 HighPhy 02 PCR clone | 97,90 | 97,90 | 97,90 | 97,90 | 97,70 | 97,90 | 97,80 | 97,81 | 99,80 | |

Figure 5

|  |  | 1 | 2 | 3 | 4 | 5 | 6 | 7 | 8 | 9 | 10 | 11 | 12 |
|---|---|---|---|---|---|---|---|---|---|---|---|---|---|
| TaG2 lambda clone, Skagen cultivar | 1 |  | 0 | 0 | 0 | 0 | 0 | 0 | 0 | 2 | 2 | 3 | 3 |
| Skagen PCR clone | 2 | 100,00 |  | 0 | 0 | 0 | 0 | 0 | 0 | 2 | 2 | 3 | 3 |
| Bob White PCR clone | 3 | 100,00 | 100,00 |  | 0 | 0 | 0 | 0 | 0 | 2 | 2 | 3 | 3 |
| Pentium PCR clone | 4 | 100,00 | 100,00 | 100,00 |  | 0 | 0 | 0 | 0 | 2 | 2 | 3 | 3 |
| Flair PCR clone | 5 | 100,00 | 100,00 | 100,00 | 100,00 |  | 0 | 0 | 0 | 2 | 2 | 3 | 3 |
| Landrace 01 PCR clone | 6 | 100,00 | 100,00 | 100,00 | 100,00 | 100,00 |  | 0 | 0 | 2 | 2 | 3 | 3 |
| Landrace 02 PCR clone | 7 | 100,00 | 100,00 | 100,00 | 100,00 | 100,00 | 100,00 |  | 0 | 2 | 2 | 3 | 3 |
| Spelt PCR clone | 8 | 100,00 | 100,00 | 100,00 | 100,00 | 100,00 | 100,00 | 100,00 |  | 2 | 2 | 3 | 3 |
| HighPhy 01 PCR clone | 9 | 99,31 | 99,31 | 99,31 | 99,31 | 99,31 | 99,31 | 99,31 | 99,31 |  | 0 | 3 | 3 |
| HighPhy 02 PCR clone | 10 | 99,31 | 99,31 | 99,31 | 99,31 | 99,31 | 99,31 | 99,31 | 99,31 | 100,00 |  | 3 | 3 |
| NGB90403 PCR clone | 11 | 98,97 | 98,97 | 98,97 | 98,97 | 98,97 | 98,97 | 98,97 | 98,97 | 98,97 | 98,97 |  | 0 |
| NGB9855 PCR clone | 12 | 98,97 | 98,97 | 98,97 | 98,97 | 98,97 | 98,97 | 98,97 | 98,97 | 98,97 | 98,97 | 100,00 |  |

```
                                         -280                        -260
                                           |                          |
TaG2 lambda clone, Skagen cultivar  TTTTGTTGCTTGCGCTTTAGTTTCAAGCTACACTTTGTAGAACAT 45
              Skagen PCR clone      TTTTGTTGCTTGCGCTTTAGTTTCAAGCTACACTTTGTAGAACAT 45
           Bob White PCR clone      TTTTGTTGCTTGCGCTTTAGTTTCAAGCTACACTTTGTAGAACAT 45
             Pentium PCR clone      TTTTGTTGCTTGCGCTTTAGTTTCAAGCTACACTTTGTAGAACAT 45
                Flair PCR clone      TTTTGTTGCTTGCGCTTTAGTTTCAAGCTACACTTTGTAGAACAT 45
          Landrace 01 PCR clone     TTTTGTTGCTTGCGCTTTAGTTTCAAGCTACACTTTGTAGAACAT 45
          Landrace 02 PCR clone     TTTTGTTGCTTGCGCTTTAGTTTCAAGCTACACTTTGTAGAACAT 45
                Spelt PCR clone     TTTTGTTGCTTGCGCTTTAGTTTCAAGCTACACTTTGTAGAACAT 45
            HighPhy 01 PCR clone    TTTTGTTGCTTGCGCTTTAGTTTCAAGCTACACTTTGTAGAACAG 45
            HighPhy 02 PCR clone    TTTTGTTGCTTGCGCTTTAGTTTCAAGCTACACTTTGTAGAACAG 45
            NGB90403 PCR clone      TTTTGTTGCTTGCGCTTTAGTTTCAAGCTACATTTTGTAGAACAT 45
            NGB9855 PCR clone       TTTTGTTGCTTGCGCTTTAGTTTCAAGCTACATTTTGTAGAACAT 45
                                         -240                        -220                   -200
                                           |                          |                     |
TaG2 lambda clone, Skagen cultivar  GAGTCATGCATGGGACGAAGGCGTCCAAACTTGGCTAGTGCAGCT 90
              Skagen PCR clone      GAGTCATGCATGGGACGAAGGCGTCCAAACTTGGCTAGTGCAGCT 90
           Bob White PCR clone      GAGTCATGCATGGGACGAAGGCGTCCAAACTTGGCTAGTGCAGCT 90
             Pentium PCR clone      GAGTCATGCATGGGACGAAGGCGTCCAAACTTGGCTAGTGCAGCT 90
                Flair PCR clone     GAGTCATGCATGGGACGAAGGCGTCCAAACTTGGCTAGTGCAGCT 90
          Landrace 01 PCR clone     GAGTCATGCATGGGACGAAGGCGTCCAAACTTGGCTAGTGCAGCT 90
          Landrace 02 PCR clone     GAGTCATGCATGGGACGAAGGCGTCCAAACTTGGCTAGTGCAGCT 90
                Spelt PCR clone     GAGTCATGCATGGGACGAAGGCGTCCAAACTTGGCTAGTGCAGCT 90
            HighPhy 01 PCR clone    GAGTCATGCATGGGACGAAGGCGTCCAAACTTGGCTAGTGCAGCT 90
            HighPhy 02 PCR clone    GAGTCATGCATGGGACGAAGGCGTCCAAACTTGGCTAGTGCAGCT 90
            NGB90403 PCR clone      GAGTCATGCATGGGACGAAGGCGTCCAAACTTGGCTAGTGCAGCT 90
            NGB9855 PCR clone       GAGTCATGCATGGGACGAAGGCGTCCAAACTTGGCTAGTGCAGCT 90
                                         -180                        -160
                                           |                          |
TaG2 lambda clone, Skagen cultivar  GCCTGCGCGTTCACAAGGCACCAAAGCGCAGGCGGCAAAGTTTGC 135
              Skagen PCR clone      GCCTGCGCGTTCACAAGGCACCAAAGCGCAGGCGGCAAAGTTTGC 135
           Bob White PCR clone      GCCTGCGCGTTCACAAGGCACCAAAGCGCAGGCGGCAAAGTTTGC 135
             Pentium PCR clone      GCCTGCGCGTTCACAAGGCACCAAAGCGCAGGCGGCAAAGTTTGC 135
                Flair PCR clone     GCCTGCGCGTTCACAAGGCACCAAAGCGCAGGCGGCAAAGTTTGC 135
          Landrace 01 PCR clone     GCCTGCGCGTTCACAAGGCACCAAAGCGCAGGCGGCAAAGTTTGC 135
          Landrace 02 PCR clone     GCCTGCGCGTTCACAAGGCACCAAAGCGCAGGCGGCAAAGTTTGC 135
                Spelt PCR clone     GCCTGCGCGTTCACAAGGCACCAAAGCGCAGGCGGCAAAGTTTGC 135
            HighPhy 01 PCR clone    GCCTGCGCGTTCACAAGGCACCAAAGCGCAGGCGGCAAAGTTTGC 135
            HighPhy 02 PCR clone    GCCTGCGCGTTCACAAGGCACCAAAGCGCAGGCGGCAAAGTTTGC 135
            NGB90403 PCR clone      GCGTGCGCGTTCACAAGGCACCAAAGCGCAGGCGGCAAAGTTTGC 135
            NGB9855 PCR clone       GCGTGCGCGTTCACAAGGCACCAAAGCGCAGGCGGCAAAGTTTGC 135
                                         -140                        -120
                                           |                          |
TaG2 lambda clone, Skagen cultivar  TCGTTTATTATCTTGGCGGTCCAAGATGGGCGGCAGGTTCCAGAC 180
              Skagen PCR clone      TCGTTTATTATCTTGGCGGTCCAAGATGGGCGGCAGGTTCCAGAC 180
           Bob White PCR clone      TCGTTTATTATCTTGGCGGTCCAAGATGGGCGGCAGGTTCCAGAC 180
             Pentium PCR clone      TCGTTTATTATCTTGGCGGTCCAAGATGGGCGGCAGGTTCCAGAC 180
                Flair PCR clone     TCGTTTATTATCTTGGCGGTCCAAGATGGGCGGCAGGTTCCAGAC 180
          Landrace 01 PCR clone     TCGTTTATTATCTTGGCGGTCCAAGATGGGCGGCAGGTTCCAGAC 180
          Landrace 02 PCR clone     TCGTTTATTATCTTGGCGGTCCAAGATGGGCGGCAGGTTCCAGAC 180
                Spelt PCR clone     TCGTTTATTATCTTGGCGGTCCAAGATGGGCGGCAGGTTCCAGAC 180
            HighPhy 01 PCR clone    TCGTTTATTATCTTGGCGGTCCAAGATGGGCGGCAGGTTCCAGAC 180
            HighPhy 02 PCR clone    TCGTTTATTATCTTGGCGGTCCAAGATGGGCGGCAGGTTCCAGAC 180
            NGB90403 PCR clone      TCGTTTATTATCTTGGCGGTCCAAGATGGGCGGCAGGTTCCAGAC 180
            NGB9855 PCR clone       TCGTTTATTATCTTGGCGGTCCAAGATGGGCGGCAGGTTCCAGAC 180
                                         -100                        -80
                                           |                          |
TaG2 lambda clone, Skagen cultivar  GATGGACGAAGACCCACCGAGTTCCACTTCCGGCTCCAACCTCCT 225
              Skagen PCR clone      GATGGACGAAGACCCACCGAGTTCCACTTCCGGCTCCAACCTCCT 225
           Bob White PCR clone      GATGGACGAAGACCCACCGAGTTCCACTTCCGGCTCCAACCTCCT 225
             Pentium PCR clone      GATGGACGAAGACCCACCGAGTTCCACTTCCGGCTCCAACCTCCT 225
                Flair PCR clone     GATGGACGAAGACCCACCGAGTTCCACTTCCGGCTCCAACCTCCT 225
          Landrace 01 PCR clone     GATGGACGAAGACCCACCGAGTTCCACTTCCGGCTCCAACCTCCT 225
          Landrace 02 PCR clone     GATGGACGAAGACCCACCGAGTTCCACTTCCGGCTCCAACCTCCT 225
                Spelt PCR clone     GATGGACGAAGACCCACCGAGTTCCACTTCCGGCTCCAACCTCCT 225
            HighPhy 01 PCR clone    GATGGACGAAGACCCACCGAGTTCCACTTCCGGCTCCAACCTCCT 225
            HighPhy 02 PCR clone    GATGGACGAAGACCCACCGAGTTCCACTTCCGGCTCCAACCTCCT 225
            NGB90403 PCR clone      GATGGACGAAGACCCACCGAGTTCCACTTCCGGCTCCAACCTCCT 225
            NGB9855 PCR clone       GATGGACGAAGACCCACCGAGTTCCACTTCCGGCTCCAACCTCCT 225
                                         -60                         -40                  -20
                                           |                          |                    |
TaG2 lambda clone, Skagen cultivar  CTGCCCGATTCATATAAGTTTCCTGCCAAAGGCATTCCAATTCTG 270
              Skagen PCR clone      CTGCCCGATTCATATAAGTTTCCTGCCAAAGGCATTCCAATTCTG 270
           Bob White PCR clone      CTGCCCGATTCATATAAGTTTCCTGCCAAAGGCATTCCAATTCTG 270
             Pentium PCR clone      CTGCCCGATTCATATAAGTTTCCTGCCAAAGGCATTCCAATTCTG 270
                Flair PCR clone     CTGCCCGATTCATATAAGTTTCCTGCCAAAGGCATTCCAATTCTG 270
          Landrace 01 PCR clone     CTGCCCGATTCATATAAGTTTCCTGCCAAAGGCATTCCAATTCTG 270
          Landrace 02 PCR clone     CTGCCCGATTCATATAAGTTTCCTGCCAAAGGCATTCCAATTCTG 270
                Spelt PCR clone     CTGCCCGATTCATATAAGTTTCCTGCCAAAGGCATTCCAATTCTG 270
            HighPhy 01 PCR clone    CTGCCCGATTCATATAAGTTTCCTGCCAAAGGCATCCCAATTCTG 270
            HighPhy 02 PCR clone    CTGCCCGATTCATATAAGTTTCCTGCCAAAGGCATCCCAATTCTG 270
            NGB90403 PCR clone      CTGCCCGATTCATATAAGTTTCCTGCCAAAGGCATCCCAATTCTG 270
            NGB9855 PCR clone       CTGCCCGATTCATATAAGTTTCCTGCCAAAGGCATCCCAATTCTG 270
                                           1
                                           |
TaG2 lambda clone, Skagen cultivar  TCAATGCCAAGCAACAACATG 291
              Skagen PCR clone      TCAATGCCAAGCAACAACATG 291
           Bob White PCR clone      TCAATGCCAAGCAACAACATG 291
             Pentium PCR clone      TCAATGCCAAGCAACAACATG 291
                Flair PCR clone     TCAATGCCAAGCAACAACATG 291
          Landrace 01 PCR clone     TCAATGCCAAGCAACAACATG 291
          Landrace 02 PCR clone     TCAATGCCAAGCAACAACATG 291
                Spelt PCR clone     TCAATGCCAAGCAACAACATG 291
            HighPhy 01 PCR clone    TCAATGCCAAGCAACAACATG 291
            HighPhy 02 PCR clone    TCAATGCCAAGCAACAACATG 291
            NGB90403 PCR clone      TCAATGCCAAGCAACAACATG 291
            NGB9855 PCR clone       TCAATGCCAAGCAACAACATG 291
```

Figure 6

Figure 7

SEQUENCE LISTING

```
<160> NUMBER OF SEQ ID NOS: 66

<210> SEQ ID NO 1
<211> LENGTH: 15
<212> TYPE: DNA
<213> ORGANISM: Triticum aestivum
<220> FEATURE:
<221> NAME/KEY: enhancer
<222> LOCATION: (1)..(15)
<220> FEATURE:
<221> NAME/KEY: modified_base
<222> LOCATION: (4)..(4)
<223> OTHER INFORMATION: V = C, G or A
<220> FEATURE:
<221> NAME/KEY: modified_base
<222> LOCATION: (4)..(4)

<400> SEQUENCE: 1
acavgagtca tgcat                                                      15

<210> SEQ ID NO 2
<211> LENGTH: 19
<212> TYPE: DNA
<213> ORGANISM: Triticum aestivum
<220> FEATURE:
<221> NAME/KEY: enhancer
<222> LOCATION: (1)..(19)
<220> FEATURE:
<221> NAME/KEY: modified_base
<222> LOCATION: (8)..(8)
<223> OTHER INFORMATION: V = C, G or A

<400> SEQUENCE: 2
tagaacavga gtcatgcat                                                  19

<210> SEQ ID NO 3
<211> LENGTH: 15
<212> TYPE: DNA
```

```
<213> ORGANISM: Triticum aestivum
<220> FEATURE:
<221> NAME/KEY: enhancer
<222> LOCATION: (1)..(15)

<400> SEQUENCE: 3
acatgagtca tgcat                                                    15

<210> SEQ ID NO 4
<211> LENGTH: 20
<212> TYPE: DNA
<213> ORGANISM: Triticum aestivum
<220> FEATURE:
<221> NAME/KEY: enhancer
<222> LOCATION: (1)..(20)

<400> SEQUENCE: 4
aacatgagtc atgcatggga                                               20

<210> SEQ ID NO 5
<211> LENGTH: 288
<212> TYPE: DNA
<213> ORGANISM: Triticum aestivum
<220> FEATURE:
<221> NAME/KEY: promoter
<222> LOCATION: (1)..(288)
<223> OTHER INFORMATION: Mutant promoter and 5' untranslated region
<220> FEATURE:
<221> NAME/KEY: enhancer
<222> LOCATION: (42)..(56)

<400> SEQUENCE: 5
ttttgttgct tgcgctttag tttcaagcta cactttgtag aacacgagtc atgcatggga    60
cgaaggcgtc caaacttggc tagtgcagct gcctgcgcgt tcacaaggca ccaaagcgca   120
ggcggcaaag tttgctcgtt tattatcttg gcggtccaag atgggcggca ggttccagac   180
gatggacgaa gacccaccga gttccacttc cggctccaac ctcctctgcc cgattcatat   240
aagtttcctg ccaaaggcat cccaattctg tcaatgccaa gcaacaac                288

<210> SEQ ID NO 6
<211> LENGTH: 271
<212> TYPE: DNA
<213> ORGANISM: Triticum aestivum
<220> FEATURE:
<221> NAME/KEY: promoter
<222> LOCATION: (1)..(271)
<223> OTHER INFORMATION: TaPAPhy_a1 mutant promoter and 5' untranslated
      region
<220> FEATURE:
<221> NAME/KEY: enhancer
<222> LOCATION: (25)..(39)

<400> SEQUENCE: 6
tagtttcaag ctacactttg tagaacacga gtcatgcatg gacgaaggc gtccaaactt     60 ggctagtgca gctgcctgcg cgttcacaag gcaccaaagc gcaggcggca agtttgctc    120 gtttattatc ttggcggtcc aagatgggcg gcaggttcca gacgatggac gaagacccac   180
cgagttccac ttccggctcc aacctcctct gcccgattca taagtttc ctgccaaagg     240 catcccaatt ctgtcaatgc caagcaacaa c                                  271

<210> SEQ ID NO 7
<211> LENGTH: 288
<212> TYPE: DNA
<213> ORGANISM: Triticum aestivum
<220> FEATURE:
```

<221> NAME/KEY: promoter
<222> LOCATION: (1)..(288)
<223> OTHER INFORMATION: Wild typeTaPAPhy Promoter and 5' untranslated
      region
<220> FEATURE:
<221> NAME/KEY: enhancer
<222> LOCATION: (42)..(56)

<400> SEQUENCE: 7
ttttgttgct tgcgctttag tttcaagcta cactttgtag aacatgagtc atgcatggga      60
cgaaggcgtc caaacttggc tagtgcagct gcctgcgcgt tcacaaggca ccaaagcgca     120
ggcggcaaag tttgctcgtt tattatcttg gcggtccaag atgggcggca ggttccagac     180
gatggacgaa gacccaccga gttccacttc cggctccaac ctcctctgcc cgattcatat     240
aagtttcctg ccaaaggcat tccaattctg tcaatgccaa gcaacaac                  288

<210> SEQ ID NO 8
<211> LENGTH: 288
<212> TYPE: DNA
<213> ORGANISM: Triticum tauschii
<220> FEATURE:
<221> NAME/KEY: promoter
<222> LOCATION: (1)..(288)
<223> OTHER INFORMATION: Wild typeTtPAPhy Promoter and 5' untranslated
      region
<220> FEATURE:
<221> NAME/KEY: enhancer
<222> LOCATION: (42)..(56)

<400> SEQUENCE: 8
ttttgttgct tgcgctttag tttcaagcta cattttgtag aacatgagtc atgcatggga      60
cgaaggcgtc caaacttggc tagtgcagct gcgtgcgcgt tcacaaggca ccaaagcgca     120
ggcggcaaag tttgctcgtt tattatcttg gcggtccaag atgggcggca ggttccagac     180
gatggacgaa gacccaccga gttccacttc cggctccaac ctcctctgcc cgattcatat     240
aagtttcctg ccaaaggcat cccaattctg tcaatgccaa gcaacaac                  288

<210> SEQ ID NO 9
<211> LENGTH: 271
<212> TYPE: DNA
<213> ORGANISM: Triticum aestivum
<220> FEATURE:
<221> NAME/KEY: promoter
<222> LOCATION: (1)..(271)
<223> OTHER INFORMATION: Wild typeTaPAPhy_a1 Promoter and 5'
      untranslated region
<220> FEATURE:
<221> NAME/KEY: enhancer
<222> LOCATION: (25)..(39)

<400> SEQUENCE: 9
tagtttcaag ctacactttg tagaacatga gtcatgcatg gacgaaggc gtccaaactt       60 ggctagtgca gctgcctgcg cgttcacaag gcaccaaagc gcaggcggca aagtttgctc    120
gtttattatc ttggcggtcc aagatgggcg gcaggttcca gacgatggac gaagacccac    180
cgagttccac ttccggctcc aacctcctct gcccgattca tataagtttc ctgccaaagg    240
cattccaatt ctgtcaatgc caagcaacaa c                                   271

<210> SEQ ID NO 10
<211> LENGTH: 287
<212> TYPE: DNA
<213> ORGANISM: Triticum aestivum
<220> FEATURE:
<221> NAME/KEY: promoter

```
<222> LOCATION: (1)..(287)
<223> OTHER INFORMATION: Wild type TaPAPhy_a3 promoter and 5'
      non-coding region
<220> FEATURE:
<221> NAME/KEY: enhancer
<222> LOCATION: (25)..(39)

<400> SEQUENCE: 10
tagtttcaag ctacattttg tagaacatga gtcatgcatg ggacgaaggt gtccaaagtc      60
caaactcggc tagtgcagct gcctgcacgt tctgacgttc acaaggcacc aaagcgcagg     120
cggcaaactt tgctcgttta ttatctcgcc ggtccaagat gggcggcaag ttctagacgc     180
tggacgaaga cccaccgaat tccatttccg gctcccaacc tcctctgccc gattcctgta     240
agtttcctgc caaatcatc ccaattctct caatgccaag caacacc                    287

<210> SEQ ID NO 11
<211> LENGTH: 240
<212> TYPE: DNA
<213> ORGANISM: Triticum aestivum
<220> FEATURE:
<221> NAME/KEY: promoter
<222> LOCATION: (1)..(240)
<223> OTHER INFORMATION: Wild type TaPAPhy_a4 promoter and 5'
      non-coding region
<220> FEATURE:
<221> NAME/KEY: enhancer
<222> LOCATION: (25)..(39)

<400> SEQUENCE: 11
tattttcaag ctacattttg tagaacatga gtcatgcatg ggacgaaggt ggccaaagtc      60
caaacttggc aggcggcaaa gtttgctcgt ttatcatctt gccggtccaa gatgggcggc     120
aggttccagg cgatggacga agacccaccg agtcccactt ccggctccca acctcctctg     180
cccgattcat ataagtttcc tgccaaaggc atcctaattc tgtcaatacc aagcaacaac     240

<210> SEQ ID NO 12
<211> LENGTH: 278
<212> TYPE: DNA
<213> ORGANISM: Triticum monococcum
<220> FEATURE:
<221> NAME/KEY: promoter
<222> LOCATION: (1)..(278)
<223> OTHER INFORMATION: High Phy TmPAPhy mutant promoter and
      5' untranslated region
<220> FEATURE:
<221> NAME/KEY: enhancer
<222> LOCATION: (25)..(39)

<400> SEQUENCE: 12
tagtttcaag ctacattttg tagaacagga gtcatgcatg gacgaaggtg tccaaagtcc      60
aaacttggct agcgcagctg cctgcacgtt cacaaggcac caaagcgcag gcggcaaagt     120
tgctcgtttt attatcttgc cggtccaaga cgggcggcag gttccagacg atggacgaag     180
acccaccgaa ttccatttcc ggctcccaac ctcctctgcc cgattcctac aagtttcctg     240
ccaaaggcat cccaattctg tcaatgccaa gcaacgcc                             278

<210> SEQ ID NO 13
<211> LENGTH: 262
<212> TYPE: DNA
<213> ORGANISM: Hordeum vulgare
<220> FEATURE:
<221> NAME/KEY: promoter
<222> LOCATION: (1)..(262)
<223> OTHER INFORMATION: Wild type HvPAPhy promoter and 5'
      untranslated region
```

```
<220> FEATURE:
<221> NAME/KEY: enhancer
<222> LOCATION: (25)..(39)
<223> OTHER INFORMATION: Wild type cereal enhancer

<400> SEQUENCE: 13
taatttcaag ctacattttg tagaacatga gccatgcatg agacgtaggc gtccaaactt      60
tggctagcgc agctgcatgc acgtccacaa ggcaccaaag gcgcaggcgg caactttgct     120
cgtttatttt cttgcgggtc caagatgagt tccagaccat ggacgaattc cacttcgggc     180
tcccaatctc ctctgccgga ttcctataag tttcctgcca agaagcatcc caatcccctc     240
aatgccaagc aacaacatca ac                                              262

<210> SEQ ID NO 14
<211> LENGTH: 262
<212> TYPE: DNA
<213> ORGANISM: Hordeum vulgare
<220> FEATURE:
<221> NAME/KEY: promoter
<222> LOCATION: (1)..(262)
<223> OTHER INFORMATION: High Phy HvPAPhy mutant promoter and
      5' non-coding region
<220> FEATURE:
<221> NAME/KEY: enhancer
<222> LOCATION: (25)..(39)

<400> SEQUENCE: 14
taatttcaag ctacattttg tagaacacga gccatgcatg agacgtaggc gtccaaactt      60
tggctagcgc agctgcatgc acgtccacaa ggcaccaaag gcgcaggcgg caactttgct     120
cgtttatttt cttgcgggtc caagatgagt tccagaccat ggacgaattc cacttcgggc     180
tcccaatctc ctctgccgga ttcctataag tttcctgcca agaagcatcc caatcccctc     240
aatgccaagc aacaacatca ac                                              262

<210> SEQ ID NO 15
<211> LENGTH: 270
<212> TYPE: DNA
<213> ORGANISM: Secale cereale
<220> FEATURE:
<221> NAME/KEY: promoter
<222> LOCATION: (1)..(270)
<223> OTHER INFORMATION: HighPhy ScPAPhy_a1 promoter and 5' non-coding
      region
<220> FEATURE:
<221> NAME/KEY: enhancer
<222> LOCATION: (25)..(39)

<400> SEQUENCE: 15
tagtttcaag ctacattttc tagaacacga gtcatgcatg ggacgaaggt gtccaaagtc      60
caaacttggc ttttgtgcag ctgcctgcac gttcacaagg caccaaagcg caggcggcaa     120
acttaatttg ctcgttcatt atcttgctgg tccaagatgg gcggcaggtt gcacccaccg     180
agttccactt ccggctccca atctcctgtg cctgattcct ataagtttcc tgccaaaagc     240
atcccaattc tgtcaatgcc aagcaacaac                                      270

<210> SEQ ID NO 16
<211> LENGTH: 280
<212> TYPE: DNA
<213> ORGANISM: Secale cereale
<220> FEATURE:
<221> NAME/KEY: promoter
<222> LOCATION: (1)..(280)
<223> OTHER INFORMATION: Wild type ScPAPhy_a2 promoter and 5'
      non-coding region
```

```
<220> FEATURE:
<221> NAME/KEY: enhancer
<222> LOCATION: (25)..(39)

<400> SEQUENCE: 16
agtttcaagc tacattttgt agaacatgag tcatgcatgg gacgaaggtg tccaaagtcc      60
aaacttggct tttgtgcagc tgcctgcacg ttcacaaggc accaaagcgc aggcggcaaa     120
ctttgctcgt tcattatctt gctggtccaa gatgggcggc aggttgcaga agatggacga     180
agacccaccg agttccactt ccggctccca atcgcctctg cccgattcct ataagtttcc     240
tgccaaaggc atcccaattc tgtcaatgcc aagcaacaac                          280

<210> SEQ ID NO 17
<211> LENGTH: 1749
<212> TYPE: DNA
<213> ORGANISM: Triticum aestivum
<220> FEATURE:
<221> NAME/KEY: CDS
<222> LOCATION: (27)..(1670)
<223> OTHER INFORMATION: Coding sequence for phytase of TaPAPhy_a1
      phytase cDNA

<400> SEQUENCE: 17
```

| | | |
|---|---|---|
| caattctgtc aatgccaagc aacaac atg tgg tgg ggg tcg ctg ctg ctg ctg | | 53 |
| Met Trp Trp Gly Ser Leu Leu Leu Leu | | |
| 1 5 | | |
| ctg ctc gcg gcc gcg gtg gcg gcg gct gct gag ccg gcg tcg acg | | 101 |
| Leu Leu Ala Ala Ala Val Ala Ala Ala Ala Glu Pro Ala Ser Thr | | |
| 10 15 20 25 | | |
| ctc acg ggc ccg tca cgg ccg gtc acg gtg gcg ctg cgg gaa gac agg | | 149 |
| Leu Thr Gly Pro Ser Arg Pro Val Thr Val Ala Leu Arg Glu Asp Arg | | |
| 30 35 40 | | |
| ggc cac gcg gtg gac ctg ccg gac acg gac ccc cgg gtg cag cgc cgg | | 197 |
| Gly His Ala Val Asp Leu Pro Asp Thr Asp Pro Arg Val Gln Arg Arg | | |
| 45 50 55 | | |
| gcc acg ggc tgg gct ccc gag cag atc gcc gtc gcg ctc tcc gcc gct | | 245 |
| Ala Thr Gly Trp Ala Pro Glu Gln Ile Ala Val Ala Leu Ser Ala Ala | | |
| 60 65 70 | | |
| ccc acc tct gcc tgg gtc tcc tgg atc acc ggg gaa ttc cag atg ggc | | 293 |
| Pro Thr Ser Ala Trp Val Ser Trp Ile Thr Gly Glu Phe Gln Met Gly | | |
| 75 80 85 | | |
| ggc acc gtc aag ccg ctg gac ccc ggc acg gtc ggc agc gtc gtg cgc | | 341 |
| Gly Thr Val Lys Pro Leu Asp Pro Gly Thr Val Gly Ser Val Val Arg | | |
| 90 95 100 105 | | |
| tac ggg ctc gcc gcc gat tct ttg gtt cgc cag gcc agc ggc gac gcg | | 389 |
| Tyr Gly Leu Ala Ala Asp Ser Leu Val Arg Gln Ala Ser Gly Asp Ala | | |
| 110 115 120 | | |
| ctc gtg tac agc cag ctc tac ccc ttc gag ggt ctc cag aac tac acc | | 437 |
| Leu Val Tyr Ser Gln Leu Tyr Pro Phe Glu Gly Leu Gln Asn Tyr Thr | | |
| 125 130 135 | | |
| tcc ggc atc atc cac cac gtc cgc ctc caa ggg ctt gag cct gcg acg | | 485 |
| Ser Gly Ile Ile His His Val Arg Leu Gln Gly Leu Glu Pro Ala Thr | | |
| 140 145 150 | | |
| aag tac tac tac cag tgc ggc gac ccg gcc ctc ccg ggg gcg atg agc | | 533 |
| Lys Tyr Tyr Tyr Gln Cys Gly Asp Pro Ala Leu Pro Gly Ala Met Ser | | |
| 155 160 165 | | |
| gcc gtc cac gcg ttc cgg acg atg ccg gcg gtg ggg ccg cgg agc tac | | 581 |
| Ala Val His Ala Phe Arg Thr Met Pro Ala Val Gly Pro Arg Ser Tyr | | |
| 170 175 180 185 | | |
| ccg ggg agg atc gcc gtg gtg gga gac ctc ggg ctc acg tac aac acc | | 629 |
| Pro Gly Arg Ile Ala Val Val Gly Asp Leu Gly Leu Thr Tyr Asn Thr | | |

```
                    190                 195                 200
acc tcc acc gtg gac cac atg gcg agc aac cgg ccg gac ctg gtc ctc         677
Thr Ser Thr Val Asp His Met Ala Ser Asn Arg Pro Asp Leu Val Leu
                205                 210                 215 ctc gtc ggc gac gtg tgc tac gcc aac atg tac ctc acc aac ggc acc         725
Leu Val Gly Asp Val Cys Tyr Ala Asn Met Tyr Leu Thr Asn Gly Thr
            220                 225                 230 gga gcg gac tgc tac tcg tgc gcg ttc ggc aag tcg acg ccc atc cac         773
Gly Ala Asp Cys Tyr Ser Cys Ala Phe Gly Lys Ser Thr Pro Ile His
        235                 240                 245 gag acg tac cag ccg cgc tgg gac tac tgg gga agg tac atg gag gcg         821
Glu Thr Tyr Gln Pro Arg Trp Asp Tyr Trp Gly Arg Tyr Met Glu Ala
250                 255                 260                 265 gtg acg tcg ggg acg ccg atg atg gtg gtg gaa ggg aac cat gag ata         869
Val Thr Ser Gly Thr Pro Met Met Val Val Glu Gly Asn His Glu Ile
                270                 275                 280 gag gag cag atc ggg aac aag acg ttc gcg gcc tac cgc tcc cgg ttc         917
Glu Glu Gln Ile Gly Asn Lys Thr Phe Ala Ala Tyr Arg Ser Arg Phe
            285                 290                 295 gcg ttc ccg tcg acg gag agc ggg tcc ttc tcc ccc ttc tac tac tcg         965
Ala Phe Pro Ser Thr Glu Ser Gly Ser Phe Ser Pro Phe Tyr Tyr Ser
        300                 305                 310 ttc gac gcc ggc ggg atc cat ttc ctc atg ctc ggc gcc tac gcc gac        1013
Phe Asp Ala Gly Gly Ile His Phe Leu Met Leu Gly Ala Tyr Ala Asp
315                 320                 325 tac ggc agg tca ggg gag cag tac aga tgg ctg gag aag gac ctg gcg        1061
Tyr Gly Arg Ser Gly Glu Gln Tyr Arg Trp Leu Glu Lys Asp Leu Ala
330                 335                 340                 345 aag gtg gac agg tcg gtg acg ccg tgg ctg gtc gcc ggc tgg cac gcg        1109
Lys Val Asp Arg Ser Val Thr Pro Trp Leu Val Ala Gly Trp His Ala
                350                 355                 360 cca tgg tac acc acc tac aag gct cac tac agg gag gtg gag tgc atg        1157
Pro Trp Tyr Thr Thr Tyr Lys Ala His Tyr Arg Glu Val Glu Cys Met
            365                 370                 375 aga gtg gcc atg gag gag ctg ctc tac tcc cac ggc ctc gac atc gcc        1205
Arg Val Ala Met Glu Glu Leu Leu Tyr Ser His Gly Leu Asp Ile Ala
        380                 385                 390 ttc acc ggc cat gtg cac gcg tat gag cgc tcc aac cgg gtg ttc aac        1253
Phe Thr Gly His Val His Ala Tyr Glu Arg Ser Asn Arg Val Phe Asn
395                 400                 405 tac acg ctg gac ccg tgc ggc gcc gtg cac atc tcg gtg ggc gac ggc        1301
Tyr Thr Leu Asp Pro Cys Gly Ala Val His Ile Ser Val Gly Asp Gly
410                 415                 420                 425 ggg aac cgc gag aag atg gcc acc acc cac gcc gac gag ccg ggg cac        1349
Gly Asn Arg Glu Lys Met Ala Thr Thr His Ala Asp Glu Pro Gly His
                430                 435                 440 tgc ccg gac ccg cgg ccc aag ccc aac gcc ttc atc ggc ggc ttc tgc        1397
Cys Pro Asp Pro Arg Pro Lys Pro Asn Ala Phe Ile Gly Gly Phe Cys
            445                 450                 455 gcc tcc aac ttc acg tcc ggc ccg gcc gcc ggc agg ttc tgc tgg gac        1445
Ala Ser Asn Phe Thr Ser Gly Pro Ala Ala Gly Arg Phe Cys Trp Asp
        460                 465                 470 cgg cag ccg gac tac agc gcc tac cgg gag agc agc ttc ggc cac ggc        1493
Arg Gln Pro Asp Tyr Ser Ala Tyr Arg Glu Ser Ser Phe Gly His Gly
475                 480                 485 atc ctc gag gtg aag aac gag acg cac gct ctg tgg aga tgg cac agg        1541
Ile Leu Glu Val Lys Asn Glu Thr His Ala Leu Trp Arg Trp His Arg
                490                 495                 500                 505 aac cag gac cac tac ggg agc gcc gga gat gag att tac att gtc cgg        1589
```

-continued

```
Asn Gln Asp His Tyr Gly Ser Ala Gly Asp Glu Ile Tyr Ile Val Arg
                510                 515                 520 gag ccg cac agg tgc ttg cac aag cac aac tcg agc agg ccg gca cac    1637
Glu Pro His Arg Cys Leu His Lys His Asn Ser Ser Arg Pro Ala His
    525                 530                 535 ggt cga tca aac acc aca cgg gaa tcg gga ggt taaccgttgt accactggag  1690
Gly Arg Ser Asn Thr Thr Arg Glu Ser Gly Gly
540                 545 tagatcgcgt ggtgtaatgg caactgtata gacggttcgc ccaagcgtgg aaataaaaa   1749

<210> SEQ ID NO 18
<211> LENGTH: 548
<212> TYPE: PRT
<213> ORGANISM: Triticum aestivum

<400> SEQUENCE: 18

Met Trp Trp Gly Ser Leu Leu Leu Leu Leu Ala Ala Ala Val
1               5                   10                  15

Ala Ala Ala Ala Glu Pro Ala Ser Thr Leu Thr Gly Pro Ser Arg Pro
                20                  25                  30

Val Thr Val Ala Leu Arg Glu Asp Arg Gly His Ala Val Asp Leu Pro
            35                  40                  45

Asp Thr Asp Pro Arg Val Gln Arg Ala Thr Gly Trp Ala Pro Glu
        50                  55                  60

Gln Ile Ala Val Ala Leu Ser Ala Pro Thr Ser Ala Trp Val Ser
65                  70                  75                  80

Trp Ile Thr Gly Glu Phe Gln Met Gly Gly Thr Val Lys Pro Leu Asp
                85                  90                  95

Pro Gly Thr Val Gly Ser Val Val Arg Tyr Gly Leu Ala Ala Asp Ser
            100                 105                 110

Leu Val Arg Gln Ala Ser Gly Asp Ala Leu Val Tyr Ser Gln Leu Tyr
        115                 120                 125

Pro Phe Glu Gly Leu Gln Asn Tyr Thr Ser Gly Ile Ile His His Val
    130                 135                 140

Arg Leu Gln Gly Leu Glu Pro Ala Thr Lys Tyr Tyr Tyr Gln Cys Gly
145                 150                 155                 160

Asp Pro Ala Leu Pro Gly Ala Met Ser Ala Val His Ala Phe Arg Thr
                165                 170                 175

Met Pro Ala Val Gly Pro Arg Ser Tyr Pro Gly Arg Ile Ala Val Val
            180                 185                 190

Gly Asp Leu Gly Leu Thr Tyr Asn Thr Thr Ser Thr Val Asp His Met
        195                 200                 205

Ala Ser Asn Arg Pro Asp Leu Val Leu Leu Val Gly Asp Val Cys Tyr
    210                 215                 220

Ala Asn Met Tyr Leu Thr Asn Gly Thr Gly Ala Asp Cys Tyr Ser Cys
225                 230                 235                 240

Ala Phe Gly Lys Ser Thr Pro Ile His Glu Thr Tyr Gln Pro Arg Trp
                245                 250                 255

Asp Tyr Trp Gly Arg Tyr Met Glu Ala Val Thr Ser Gly Thr Pro Met
            260                 265                 270

Met Val Val Glu Gly Asn His Glu Ile Glu Glu Gln Ile Gly Asn Lys
        275                 280                 285

Thr Phe Ala Ala Tyr Arg Ser Arg Phe Ala Phe Pro Ser Thr Glu Ser
    290                 295                 300

Gly Ser Phe Ser Pro Phe Tyr Tyr Ser Phe Asp Ala Gly Gly Ile His
```

```
                305                 310                 315                 320
        Phe Leu Met Leu Gly Ala Tyr Ala Asp Tyr Gly Arg Ser Gly Glu Gln
                        325                 330                 335

Tyr Arg Trp Leu Glu Lys Asp Leu Ala Lys Val Asp Arg Ser Val Thr
                        340                 345                 350

Pro Trp Leu Val Ala Gly Trp His Ala Pro Trp Tyr Thr Thr Tyr Lys
                        355                 360                 365

Ala His Tyr Arg Glu Val Glu Cys Met Arg Val Ala Met Glu Glu Leu
                370                 375                 380

Leu Tyr Ser His Gly Leu Asp Ile Ala Phe Thr Gly His Val His Ala
        385                 390                 395                 400

Tyr Glu Arg Ser Asn Arg Val Phe Asn Tyr Thr Leu Asp Pro Cys Gly
                        405                 410                 415

Ala Val His Ile Ser Val Gly Asp Gly Gly Asn Arg Glu Lys Met Ala
                        420                 425                 430

Thr Thr His Ala Asp Glu Pro Gly His Cys Pro Asp Pro Arg Pro Lys
                435                 440                 445

Pro Asn Ala Phe Ile Gly Gly Phe Cys Ala Ser Asn Phe Thr Ser Gly
        450                 455                 460

Pro Ala Ala Gly Arg Phe Cys Trp Asp Arg Gln Pro Asp Tyr Ser Ala
        465                 470                 475                 480

Tyr Arg Glu Ser Ser Phe Gly His Gly Ile Leu Glu Val Lys Asn Glu
                        485                 490                 495

Thr His Ala Leu Trp Arg Trp His Arg Asn Gln Asp His Tyr Gly Ser
                        500                 505                 510

Ala Gly Asp Glu Ile Tyr Ile Val Arg Glu Pro His Arg Cys Leu His
                515                 520                 525

Lys His Asn Ser Ser Arg Pro Ala His Gly Arg Ser Asn Thr Thr Arg
           530                 535                 540

Glu Ser Gly Gly
        545

<210> SEQ ID NO 19
<211> LENGTH: 1743
<212> TYPE: DNA
<213> ORGANISM: Triticum aestivum
<220> FEATURE:
<221> NAME/KEY: CDS
<222> LOCATION: (22)..(1665)
<223> OTHER INFORMATION: CDS encoding phytase of TaPAPhy_a2 Phytase cDNA

<400> SEQUENCE: 19
ctctcaatgc caagcaacac c atg tgg tgg ggg tcg ctg cgg ctg ctg ctg         51
                        Met Trp Trp Gly Ser Leu Arg Leu Leu Leu
                         1               5                  10 ctg ctc gcg gcg gcg gtg gcg gcg gct gct gag ccg gcg tcg acg ctc         99
Leu Leu Ala Ala Ala Val Ala Ala Ala Ala Glu Pro Ala Ser Thr Leu
            15                  20                  25 acc ggc ccg tcg cgg ccg gtg acg gtg gcg ctg cgg aaa gac agg ggc        147
Thr Gly Pro Ser Arg Pro Val Thr Val Ala Leu Arg Lys Asp Arg Gly
        30                  35                  40 cac gcg gtg gac ctg ccg gac acg gac ccc cgg gtg cag cgc cgg gcc        195
His Ala Val Asp Leu Pro Asp Thr Asp Pro Arg Val Gln Arg Arg Ala
    45                  50                  55 acg ggc tgg gct ccc gag cag atc acc gtc gcg ctc tcc gcc gct ccc        243
Thr Gly Trp Ala Pro Glu Gln Ile Thr Val Ala Leu Ser Ala Ala Pro
60                  65                  70
```

```
acc tct gcc tgg gtc tcc tgg atc acc ggc gaa ttc cag atg ggc ggc     291
Thr Ser Ala Trp Val Ser Trp Ile Thr Gly Glu Phe Gln Met Gly Gly
 75              80                  85                  90 acc gtc aag ccg ctg aac ccc ggc acg gtc gcc agc gtc gtg cgc tac     339
Thr Val Lys Pro Leu Asn Pro Gly Thr Val Ala Ser Val Val Arg Tyr
                 95                 100                 105 ggg ctc gcc gcc gat tct ttg gtt cac gag gcc acc ggc gac gcg ctc     387
Gly Leu Ala Ala Asp Ser Leu Val His Glu Ala Thr Gly Asp Ala Leu
            110                 115                 120 gtg tac agc cag ctc tac ccc ttc gag ggc ctc cag aac tac acc tcc     435
Val Tyr Ser Gln Leu Tyr Pro Phe Glu Gly Leu Gln Asn Tyr Thr Ser
        125                 130                 135 ggc atc atc cac cac gtc cgc ctc caa ggg ctt gag cct gcg acg aag     483
Gly Ile Ile His His Val Arg Leu Gln Gly Leu Glu Pro Ala Thr Lys
    140                 145                 150 tac tac tac cag tgc ggc gac ccg ggc atc ccg ggg gcg atg agc gcc     531
Tyr Tyr Tyr Gln Cys Gly Asp Pro Gly Ile Pro Gly Ala Met Ser Ala
155                 160                 165                 170 gtc cac gcg ttc cgg acg atg ccg gcg gtg ggg ccg cgg agc tac ccg     579
Val His Ala Phe Arg Thr Met Pro Ala Val Gly Pro Arg Ser Tyr Pro
                175                 180                 185 ggg agg atc gcc gtg gtg gga gac ctc ggg ctc acg tac aac acc acc     627
Gly Arg Ile Ala Val Val Gly Asp Leu Gly Leu Thr Tyr Asn Thr Thr
            190                 195                 200 tcg acc gtg gac cac atg gtc agc aac cgg ccc gac ctg gtc ctc ctc     675
Ser Thr Val Asp His Met Val Ser Asn Arg Pro Asp Leu Val Leu Leu
        205                 210                 215 gtc ggc gac gtg tgc tac gcc aac atg tac ctc acc aac ggc acc gga     723
Val Gly Asp Val Cys Tyr Ala Asn Met Tyr Leu Thr Asn Gly Thr Gly
    220                 225                 230 gcg gac tgc tac tcg tgc gcg ttc ggc aag tcg acg ccc atc cac gag     771
Ala Asp Cys Tyr Ser Cys Ala Phe Gly Lys Ser Thr Pro Ile His Glu
235                 240                 245                 250 acg tac cag ccg cgc tgg gac tac tgg gga agg tac atg gag gcg gtg     819
Thr Tyr Gln Pro Arg Trp Asp Tyr Trp Gly Arg Tyr Met Glu Ala Val
                255                 260                 265 acg tcg ggc acg ccg atg atg gtg gtg gaa ggg aac cat gag ata gag     867
Thr Ser Gly Thr Pro Met Met Val Val Glu Gly Asn His Glu Ile Glu
            270                 275                 280 gag cag atc ggc aac aag acg ttc gcg gcc tac cgc tcc cgg ttc gcg     915
Glu Gln Ile Gly Asn Lys Thr Phe Ala Ala Tyr Arg Ser Arg Phe Ala
        285                 290                 295 ttc ccg tcg acg gag agc ggc tcc ttc tcc ccc ttc tac tac tcg ttc     963
Phe Pro Ser Thr Glu Ser Gly Ser Phe Ser Pro Phe Tyr Tyr Ser Phe
    300                 305                 310 gac gcc ggc ggg atc cat ttc atc atg ctc gcc gcc tac gcc gat tac    1011
Asp Ala Gly Gly Ile His Phe Ile Met Leu Ala Ala Tyr Ala Asp Tyr
315                 320                 325                 330 agc agg tca ggg gag cag tac aga tgg ctg gtg aag gac ctg gcg aag    1059
Ser Arg Ser Gly Glu Gln Tyr Arg Trp Leu Val Lys Asp Leu Ala Lys
                335                 340                 345 gtg gac agg gcg gtg acc ccc tgg ctg gtc gcc ggc tgg cac gcg cca    1107
Val Asp Arg Ala Val Thr Pro Trp Leu Val Ala Gly Trp His Ala Pro
            350                 355                 360 tgg tac acc acc tac aag gct cac tac agg gag gtg gag tgc atg aga    1155
Trp Tyr Thr Thr Tyr Lys Ala His Tyr Arg Glu Val Glu Cys Met Arg
        365                 370                 375 gtg gcc atg gag gag ctg ctc tac tcc cac ggc ctc gac atc gcc ttc    1203
Val Ala Met Glu Glu Leu Leu Tyr Ser His Gly Leu Asp Ile Ala Phe
    380                 385                 390
```

```
acc ggc cat gtg cac gcg tac gag cgc tcc aac cgg gtg ttc aac tac      1251
Thr Gly His Val His Ala Tyr Glu Arg Ser Asn Arg Val Phe Asn Tyr
395                 400                 405                 410 acg ctg gac ccg tgc ggc gcg gtg cac atc tcg gtg ggc gac ggc ggg      1299
Thr Leu Asp Pro Cys Gly Ala Val His Ile Ser Val Gly Asp Gly Gly
            415                 420                 425 aac cgg gag aag atg gcc acc acc cac gcc gac gag ccg ggg cac tgc      1347
Asn Arg Glu Lys Met Ala Thr Thr His Ala Asp Glu Pro Gly His Cys
        430                 435                 440 ccg gac ccg cgg ccc aag ccc aac gcc ttc atc ggc tgc ttc tgc gcc      1395
Pro Asp Pro Arg Pro Lys Pro Asn Ala Phe Ile Gly Cys Phe Cys Ala
    445                 450                 455 ttc aac ttc acg tcc ggc ccg gcc gcc ggc agg ttc tgc tgg gac cgg      1443
Phe Asn Phe Thr Ser Gly Pro Ala Ala Gly Arg Phe Cys Trp Asp Arg
460                 465                 470 cag ccg gac tac agc gcc tac cgg gag agc agc ttc ggc cac ggc atc      1491
Gln Pro Asp Tyr Ser Ala Tyr Arg Glu Ser Ser Phe Gly His Gly Ile
475                 480                 485                 490 ctc gag gtg aag aac gag acg cac gct ctg tgg aga tgg cac agg aac      1539
Leu Glu Val Lys Asn Glu Thr His Ala Leu Trp Arg Trp His Arg Asn
            495                 500                 505 cag gac cac tac gga agc gcc gga gat gag att tac att gtc cgg gag      1587
Gln Asp His Tyr Gly Ser Ala Gly Asp Glu Ile Tyr Ile Val Arg Glu
        510                 515                 520 ccg cac agg tgc ttg cac aag cac aac tcg acc agg ccg gca cac ggt      1635
Pro His Arg Cys Leu His Lys His Asn Ser Thr Arg Pro Ala His Gly
    525                 530                 535 cga caa aac acc aca cgg gaa tcg gga ggt taactgctgt actgctggag        1685
Arg Gln Asn Thr Thr Arg Glu Ser Gly Gly
540                 545 tagatcgcgc ggtgtaatgg caactttata gatgattcgc ccaagcgtgg aaataaaa     1743

<210> SEQ ID NO 20
<211> LENGTH: 548
<212> TYPE: PRT
<213> ORGANISM: Triticum aestivum

<400> SEQUENCE: 20

Met Trp Trp Gly Ser Leu Arg Leu Leu Leu Leu Ala Ala Val
1               5                   10                  15

Ala Ala Ala Glu Pro Ala Ser Thr Leu Thr Gly Pro Ser Arg Pro
            20                  25                  30

Val Thr Val Ala Leu Arg Lys Asp Arg Gly His Ala Val Asp Leu Pro
        35                  40                  45

Asp Thr Asp Pro Arg Val Gln Arg Arg Ala Thr Gly Trp Ala Pro Glu
    50                  55                  60

Gln Ile Thr Val Ala Leu Ser Ala Ala Pro Thr Ser Ala Trp Val Ser
65                  70                  75                  80

Trp Ile Thr Gly Glu Phe Gln Met Gly Gly Thr Val Lys Pro Leu Asn
                85                  90                  95

Pro Gly Thr Val Ala Ser Val Val Arg Tyr Gly Leu Ala Ala Asp Ser
            100                 105                 110

Leu Val His Glu Ala Thr Gly Asp Ala Leu Val Tyr Ser Gln Leu Tyr
        115                 120                 125

Pro Phe Glu Gly Leu Gln Asn Tyr Thr Ser Gly Ile Ile His His Val
    130                 135                 140

Arg Leu Gln Gly Leu Glu Pro Ala Thr Lys Tyr Tyr Tyr Gln Cys Gly
```

```
            145                 150                 155                 160
Asp Pro Gly Ile Pro Gly Ala Met Ser Ala Val His Ala Phe Arg Thr
                    165                 170                 175

Met Pro Ala Val Gly Pro Arg Ser Tyr Pro Gly Arg Ile Ala Val Val
            180                 185                 190

Gly Asp Leu Gly Leu Thr Tyr Asn Thr Thr Ser Thr Val Asp His Met
        195                 200                 205

Val Ser Asn Arg Pro Asp Leu Val Leu Leu Val Gly Asp Val Cys Tyr
    210                 215                 220

Ala Asn Met Tyr Leu Thr Asn Gly Thr Gly Ala Asp Cys Tyr Ser Cys
225                 230                 235                 240

Ala Phe Gly Lys Ser Thr Pro Ile His Glu Thr Tyr Gln Pro Arg Trp
                245                 250                 255

Asp Tyr Trp Gly Arg Tyr Met Glu Ala Val Thr Ser Gly Thr Pro Met
            260                 265                 270

Met Val Val Glu Gly Asn His Glu Ile Glu Glu Gln Ile Gly Asn Lys
        275                 280                 285

Thr Phe Ala Ala Tyr Arg Ser Arg Phe Ala Phe Pro Ser Thr Glu Ser
    290                 295                 300

Gly Ser Phe Ser Pro Phe Tyr Ser Phe Asp Ala Gly Ile His
305                 310                 315                 320

Phe Ile Met Leu Ala Ala Tyr Ala Asp Tyr Ser Arg Ser Gly Glu Gln
                325                 330                 335

Tyr Arg Trp Leu Val Lys Asp Leu Ala Lys Val Asp Arg Ala Val Thr
            340                 345                 350

Pro Trp Leu Val Ala Gly Trp His Ala Pro Trp Tyr Thr Thr Tyr Lys
        355                 360                 365

Ala His Tyr Arg Glu Val Glu Cys Met Arg Val Ala Met Glu Glu Leu
    370                 375                 380

Leu Tyr Ser His Gly Leu Asp Ile Ala Phe Thr Gly His Val His Ala
385                 390                 395                 400

Tyr Glu Arg Ser Asn Arg Val Phe Asn Tyr Thr Leu Asp Pro Cys Gly
                405                 410                 415

Ala Val His Ile Ser Val Gly Asp Gly Gly Asn Arg Glu Lys Met Ala
            420                 425                 430

Thr Thr His Ala Asp Glu Pro Gly His Cys Pro Asp Pro Arg Pro Lys
        435                 440                 445

Pro Asn Ala Phe Ile Gly Cys Phe Cys Ala Phe Asn Phe Thr Ser Gly
    450                 455                 460

Pro Ala Ala Gly Arg Phe Cys Trp Asp Arg Gln Pro Asp Tyr Ser Ala
465                 470                 475                 480

Tyr Arg Glu Ser Ser Phe Gly His Gly Ile Leu Glu Val Lys Asn Glu
                485                 490                 495

Thr His Ala Leu Trp Arg Trp Arg Asn Gln Asp His Tyr Gly Ser
            500                 505                 510

Ala Gly Asp Glu Ile Tyr Ile Val Arg Glu Pro His Arg Cys Leu His
        515                 520                 525

Lys His Asn Ser Thr Arg Pro Ala His Gly Arg Gln Asn Thr Thr Arg
    530                 535                 540

Glu Ser Gly Gly
545

<210> SEQ ID NO 21
```

```
<211> LENGTH: 1734
<212> TYPE: DNA
<213> ORGANISM: Triticum aestivum
<220> FEATURE:
<221> NAME/KEY: CDS
<222> LOCATION: (22)..(1638)
<223> OTHER INFORMATION: phytase coding sequence of TaPAPhy_a3 phytase
      cDNA

<400> SEQUENCE: 21
ctgtcaatac caagcaacaa c atg tgg tgg ggg tcg ctg cgg ctg ctg ctg           51
                        Met Trp Trp Gly Ser Leu Arg Leu Leu Leu
                        1               5                   10 ctg ctc gcg gcg gcg gtg gcg gcg gct gct gag cca gcg tcg acg ctc           99
Leu Leu Ala Ala Ala Val Ala Ala Ala Ala Glu Pro Ala Ser Thr Leu
                15                  20                  25 acg ggg ccg tcg cgg ccg gtg acg gtg acg ctt cgg gaa gac agg ggc          147
Thr Gly Pro Ser Arg Pro Val Thr Val Thr Leu Arg Glu Asp Arg Gly
            30                  35                  40 cac gcg gtg gac ctg ccg gac acg gac ccc cgg gtg cag cgc cgg gcc          195
His Ala Val Asp Leu Pro Asp Thr Asp Pro Arg Val Gln Arg Arg Ala
        45                  50                  55 acg ggc tgg gct ccc gag cag atc gcc gtc gcg ctc tcc gcc gct ccc          243
Thr Gly Trp Ala Pro Glu Gln Ile Ala Val Ala Leu Ser Ala Ala Pro
    60                  65                  70 acc tct gcc tgg gtc tcc tgg atc acc ggg gaa ttc cag atg ggc ggc          291
Thr Ser Ala Trp Val Ser Trp Ile Thr Gly Glu Phe Gln Met Gly Gly
75                  80                  85                  90 acc gtc aag ccg ctg gac ccc ggc acg gtc gcc agc gtc gtg cgc tac          339
Thr Val Lys Pro Leu Asp Pro Gly Thr Val Ala Ser Val Val Arg Tyr
                95                  100                 105 ggg ctc gcc gcc gat tct ttg gtt cgc cag gcc acc ggc gac gcg ctc          387
Gly Leu Ala Ala Asp Ser Leu Val Arg Gln Ala Thr Gly Asp Ala Leu
            110                 115                 120 gtg tac agc cag ctc tac ccc ttc gag ggc ctc cag aac tac acc tcc          435
Val Tyr Ser Gln Leu Tyr Pro Phe Glu Gly Leu Gln Asn Tyr Thr Ser
        125                 130                 135 ggc atc atc cac cac gtc cgc ctc caa ggg ctt gag cct gcg acg aag          483
Gly Ile Ile His His Val Arg Leu Gln Gly Leu Glu Pro Ala Thr Lys
    140                 145                 150 tac tac tac cag tgt ggc gac ccg gcc ctc ccg ggg gcg atg agc gcc          531
Tyr Tyr Tyr Gln Cys Gly Asp Pro Ala Leu Pro Gly Ala Met Ser Ala
155                 160                 165                 170 gtc cac gcg ttc cgg acg atg ccg gcg gtg ggg ccg cgg agc tac ccg          579
Val His Ala Phe Arg Thr Met Pro Ala Val Gly Pro Arg Ser Tyr Pro
                175                 180                 185 ggg agg atc gcc gtg gtg gga gac ctc ggg ctc acg tac aac acc acg          627
Gly Arg Ile Ala Val Val Gly Asp Leu Gly Leu Thr Tyr Asn Thr Thr
            190                 195                 200 tcg acc gtg gac cac atg gcg agc aac cgg ccg gac ctg gtc ctc ctc          675
Ser Thr Val Asp His Met Ala Ser Asn Arg Pro Asp Leu Val Leu Leu
        205                 210                 215 ctc ggt gac gtc agc tac gcc aac ctg tac ctc acc aac ggc acc gga          723
Leu Gly Asp Val Ser Tyr Ala Asn Leu Tyr Leu Thr Asn Gly Thr Gly
    220                 225                 230 gcg gac tgc tac tcg tgc gcg ttc ggc aag tcc acg ccc atc cac gag          771
Ala Asp Cys Tyr Ser Cys Ala Phe Gly Lys Ser Thr Pro Ile His Glu
235                 240                 245                 250 acg tac cag ccg cgc tgg gac tac tgg gga agg tac atg gag gcg gtg          819
Thr Tyr Gln Pro Arg Trp Asp Tyr Trp Gly Arg Tyr Met Glu Ala Val
                255                 260                 265
```

```
acg tcg ggg acg ccg atg gtg gtg gtg gag ggg aac cat gag ata gag    867
Thr Ser Gly Thr Pro Met Val Val Val Glu Gly Asn His Glu Ile Glu
            270                 275                 280 gag cag atc ggc aac aag acg ttc gcg gcc tac cgc tcc cgg ttc gcg    915
Glu Gln Ile Gly Asn Lys Thr Phe Ala Ala Tyr Arg Ser Arg Phe Ala
        285                 290                 295 ttc ccg tcg acg gag agc ggg tcc ttc tcc ccc ttc tac tac tcg ttc    963
Phe Pro Ser Thr Glu Ser Gly Ser Phe Ser Pro Phe Tyr Tyr Ser Phe
    300                 305                 310 gac gcc ggg ggg atc cat ttc gtc atg ctc ggc gcc tac gcc gac tac   1011
Asp Ala Gly Gly Ile His Phe Val Met Leu Gly Ala Tyr Ala Asp Tyr
315                 320                 325                 330 ggc agg tca ggg gag cag tac aga tgg ctc gag aag gac ctg gcg aag   1059
Gly Arg Ser Gly Glu Gln Tyr Arg Trp Leu Glu Lys Asp Leu Ala Lys
                335                 340                 345 gtg gac agg tcg gtg acg ccg tgg ctg gtc gcc ggc tgg cac gcg cca   1107
Val Asp Arg Ser Val Thr Pro Trp Leu Val Ala Gly Trp His Ala Pro
            350                 355                 360 tgg tac acc acc tat aag gct cac tac agg gag gtg gag tgc atg aga   1155
Trp Tyr Thr Thr Tyr Lys Ala His Tyr Arg Glu Val Glu Cys Met Arg
        365                 370                 375 gtg gcc atg gag gag ctg ctc tac tcc cac ggc ctc gac atc gcc ttc   1203
Val Ala Met Glu Glu Leu Leu Tyr Ser His Gly Leu Asp Ile Ala Phe
    380                 385                 390 acc ggc cat gtg cac gcg tac gag cgc tcc aac cgg gtg ttc aac tac   1251
Thr Gly His Val His Ala Tyr Glu Arg Ser Asn Arg Val Phe Asn Tyr
395                 400                 405                 410 acg ctg gac ccg tgc ggc gcc gtg cac atc tcg gtg ggc gac ggc ggg   1299
Thr Leu Asp Pro Cys Gly Ala Val His Ile Ser Val Gly Asp Gly Gly
                415                 420                 425 aac cgc gag aag atg gcc acc acc cac gcc gac gag ccg ggg cac tgc   1347
Asn Arg Glu Lys Met Ala Thr Thr His Ala Asp Glu Pro Gly His Cys
            430                 435                 440 ccg gaa ccg cgg gcc aag ccc aac gcc ttc atc ggc ggc ttc tgc gcc   1395
Pro Glu Pro Arg Ala Lys Pro Asn Ala Phe Ile Gly Gly Phe Cys Ala
        445                 450                 455 ttt aac ttc acg tcc ggc ccg gcc gcc ggc agg ttc tgc tgg gac cgg   1443
Phe Asn Phe Thr Ser Gly Pro Ala Ala Gly Arg Phe Cys Trp Asp Arg
    460                 465                 470 cag ccg gac tac agc gcc tac cgg gag agc agc ttc ggc cac ggc atc   1491
Gln Pro Asp Tyr Ser Ala Tyr Arg Glu Ser Ser Phe Gly His Gly Ile
475                 480                 485                 490 ctc gag gtg aag aac gag acg cac gct ctg tgg aga tgg cac agg aac   1539
Leu Glu Val Lys Asn Glu Thr His Ala Leu Trp Arg Trp His Arg Asn
                495                 500                 505 cag gac atg tac ggg agc gcc gga gat gag att tac att gtc cgg gag   1587
Gln Asp Met Tyr Gly Ser Ala Gly Asp Glu Ile Tyr Ile Val Arg Glu
            510                 515                 520 ccc cac agg tgc ttg cac aaa cac aac tcg acc agg ccg aca cac ggt   1635
Pro His Arg Cys Leu His Lys His Asn Ser Thr Arg Pro Thr His Gly
        525                 530                 535 cga taaaacatca cacgggaatc tggaggtact actggagtaa acctcccggt        1688
Arg gtaataatgg caactattga cggttcgtcc aagcgtggaa ataaaa                1734

<210> SEQ ID NO 22
<211> LENGTH: 539
<212> TYPE: PRT
<213> ORGANISM: Triticum aestivum
```

```
<400> SEQUENCE: 22

Met Trp Trp Gly Ser Leu Arg Leu Leu Leu Leu Ala Ala Ala Val
1               5                   10                  15

Ala Ala Ala Ala Glu Pro Ala Ser Thr Leu Thr Gly Pro Ser Arg Pro
            20                  25                  30

Val Thr Val Thr Leu Arg Glu Asp Arg Gly His Ala Val Asp Leu Pro
            35                  40                  45

Asp Thr Asp Pro Arg Val Gln Arg Arg Ala Thr Gly Trp Ala Pro Glu
        50                  55                  60

Gln Ile Ala Val Ala Leu Ser Ala Ala Pro Thr Ser Ala Trp Val Ser
65                  70                  75                  80

Trp Ile Thr Gly Glu Phe Gln Met Gly Gly Thr Val Lys Pro Leu Asp
                85                  90                  95

Pro Gly Thr Val Ala Ser Val Val Arg Tyr Gly Leu Ala Ala Asp Ser
                100                 105                 110

Leu Val Arg Gln Ala Thr Gly Asp Ala Leu Val Tyr Ser Gln Leu Tyr
            115                 120                 125

Pro Phe Glu Gly Leu Gln Asn Tyr Thr Ser Gly Ile Ile His His Val
    130                 135                 140

Arg Leu Gln Gly Leu Glu Pro Ala Thr Lys Tyr Tyr Tyr Gln Cys Gly
145                 150                 155                 160

Asp Pro Ala Leu Pro Gly Ala Met Ser Ala Val His Ala Phe Arg Thr
                165                 170                 175

Met Pro Ala Val Gly Pro Arg Ser Tyr Pro Gly Arg Ile Ala Val Val
            180                 185                 190

Gly Asp Leu Gly Leu Thr Tyr Asn Thr Thr Ser Thr Val Asp His Met
        195                 200                 205

Ala Ser Asn Arg Pro Asp Leu Val Leu Leu Gly Asp Val Ser Tyr
    210                 215                 220

Ala Asn Leu Tyr Leu Thr Asn Gly Thr Gly Ala Asp Cys Tyr Ser Cys
225                 230                 235                 240

Ala Phe Gly Lys Ser Thr Pro Ile His Glu Thr Tyr Gln Pro Arg Trp
                245                 250                 255

Asp Tyr Trp Gly Arg Tyr Met Glu Ala Val Thr Ser Gly Thr Pro Met
            260                 265                 270

Val Val Val Glu Gly Asn His Glu Ile Glu Gln Ile Gly Asn Lys
        275                 280                 285

Thr Phe Ala Ala Tyr Arg Ser Arg Phe Ala Phe Pro Ser Thr Glu Ser
    290                 295                 300

Gly Ser Phe Ser Pro Phe Tyr Ser Phe Asp Ala Gly Gly Ile His
305                 310                 315                 320

Phe Val Met Leu Gly Ala Tyr Ala Asp Tyr Gly Arg Ser Gly Glu Gln
                325                 330                 335

Tyr Arg Trp Leu Glu Lys Asp Leu Ala Lys Val Asp Arg Ser Val Thr
            340                 345                 350

Pro Trp Leu Val Ala Gly Trp His Ala Pro Trp Tyr Thr Thr Tyr Lys
        355                 360                 365

Ala His Tyr Arg Glu Val Glu Cys Met Arg Val Ala Met Glu Glu Leu
    370                 375                 380

Leu Tyr Ser His Gly Leu Asp Ile Ala Phe Thr Gly His Val His Ala
385                 390                 395                 400

Tyr Glu Arg Ser Asn Arg Val Phe Asn Tyr Thr Leu Asp Pro Cys Gly
                405                 410                 415
```

```
Ala Val His Ile Ser Val Gly Asp Gly Gly Asn Arg Glu Lys Met Ala
            420                 425                 430

Thr Thr His Ala Asp Glu Pro Gly His Cys Pro Glu Pro Arg Ala Lys
        435                 440                 445

Pro Asn Ala Phe Ile Gly Gly Phe Cys Ala Phe Asn Phe Thr Ser Gly
450                 455                 460

Pro Ala Ala Gly Arg Phe Cys Trp Asp Arg Gln Pro Asp Tyr Ser Ala
465                 470                 475                 480

Tyr Arg Glu Ser Ser Phe Gly His Gly Ile Leu Glu Val Lys Asn Glu
                485                 490                 495

Thr His Ala Leu Trp Arg Trp His Arg Asn Gln Asp Met Tyr Gly Ser
            500                 505                 510

Ala Gly Asp Glu Ile Tyr Ile Val Arg Glu Pro His Arg Cys Leu His
        515                 520                 525

Lys His Asn Ser Thr Arg Pro Thr His Gly Arg
        530                 535

<210> SEQ ID NO 23
<211> LENGTH: 1730
<212> TYPE: DNA
<213> ORGANISM: Triticum monococcum
<220> FEATURE:
<221> NAME/KEY: CDS
<222> LOCATION: (17)..(1651)
<223> OTHER INFORMATION: Phytase coding sequence of TmPAPhy_a1 phytase
      cDNA

<400> SEQUENCE: 23
aatgccaagc aacgcc atg tgg tgg ggg gcg ctg cag ctg ctg ctg ctg ctc     52
                Met Trp Trp Gly Ala Leu Gln Leu Leu Leu Leu Leu
                1               5                   10 gtg gcg gcg gct gct gag ccg gcg tcg acg ctc acc ggc ccg tcg cgg       100
Val Ala Ala Ala Ala Glu Pro Ala Ser Thr Leu Thr Gly Pro Ser Arg
            15                  20                  25 ccg gtg acg gtg gcg ctg cgg aaa gac agg ggc cac gcg gtg gac ctg       148
Pro Val Thr Val Ala Leu Arg Lys Asp Arg Gly His Ala Val Asp Leu
    30                  35                  40 ccg gac acg gac ccc cgg gtg cag cgc cgg gcc acg ggc tgg gct ccc       196
Pro Asp Thr Asp Pro Arg Val Gln Arg Arg Ala Thr Gly Trp Ala Pro
45                  50                  55                  60 gag cag atc acc gtc gcg ctc tcc gcc gct ccc acc tct gcc tgg gtc       244
Glu Gln Ile Thr Val Ala Leu Ser Ala Ala Pro Thr Ser Ala Trp Val
                65                  70                  75 tcc tgg atc acc ggg gaa ttc cag atg ggc ggc aca gtc aag ccg ctg       292
Ser Trp Ile Thr Gly Glu Phe Gln Met Gly Gly Thr Val Lys Pro Leu
            80                  85                  90 cac ccc ggc acg gtc gcc agc gtc gtg cgc tac ggg ctc gcc gcc gat       340
His Pro Gly Thr Val Ala Ser Val Val Arg Tyr Gly Leu Ala Ala Asp
        95                  100                 105 tct ttg gtt cgc gag gcc acc ggc gac gcg ctt gtg tac agc cag ctc       388
Ser Leu Val Arg Glu Ala Thr Gly Asp Ala Leu Val Tyr Ser Gln Leu
    110                 115                 120 tac ccc ttc gag ggc ctc cag aac tac acc tcc ggc atc atc cac cac       436
Tyr Pro Phe Glu Gly Leu Gln Asn Tyr Thr Ser Gly Ile Ile His His
125                 130                 135                 140 gtc cgc ctc caa ggg ctt gag cct gcg acg aag tac tac tac cag tgc       484
Val Arg Leu Gln Gly Leu Glu Pro Ala Thr Lys Tyr Tyr Tyr Gln Cys
                145                 150                 155 ggc gac ccg ggc atc ccg ggg gcg atg agc gcc gtc cac gcg ttc cgg       532
```

-continued

| | | | |
|---|---|---|---|
| Gly Asp Pro Gly Ile Pro Gly Ala Met Ser Ala Val His Ala Phe Arg<br>160                        165                      170 | | | |

```
acg atg ccg gcg gtg ggg ccg cgg agc tac ccg ggg agg atc gcc gtg      580
Thr Met Pro Ala Val Gly Pro Arg Ser Tyr Pro Gly Arg Ile Ala Val
        175                 180                 185 gtg gga gac ctc ggg ctc acg tac aac acc acc tcc acc gtg gac cac      628
Val Gly Asp Leu Gly Leu Thr Tyr Asn Thr Thr Ser Thr Val Asp His
        190                 195                 200 atg gtc agc aac cgg ccg gac ctg gtc ctc ctc gtc ggc gac gtg tgc      676
Met Val Ser Asn Arg Pro Asp Leu Val Leu Leu Val Gly Asp Val Cys
205                 210                 215                 220 tac gcc aac atg tac ctc acc aac ggc acc gga gcg gac tgc tac tcg      724
Tyr Ala Asn Met Tyr Leu Thr Asn Gly Thr Gly Ala Asp Cys Tyr Ser
                225                 230                 235 tgc gcg ttc ggc aag tcg acg ccc atc cac gag acg tac cag ccg cgc      772
Cys Ala Phe Gly Lys Ser Thr Pro Ile His Glu Thr Tyr Gln Pro Arg
        240                 245                 250 tgg gac tac tgg gga agg tac atg gag gcg gtg acg tcg ggg acg ccg      820
Trp Asp Tyr Trp Gly Arg Tyr Met Glu Ala Val Thr Ser Gly Thr Pro
        255                 260                 265 atg atg gtg gtg gaa ggg aac cat gag atc gag gag cag atc cgc aac      868
Met Met Val Val Glu Gly Asn His Glu Ile Glu Glu Gln Ile Arg Asn
270                 275                 280 agg acg ttc gcg gcc tac cgc tcc cgg ttc gcg ttc ccg tcg acg gag      916
Arg Thr Phe Ala Ala Tyr Arg Ser Arg Phe Ala Phe Pro Ser Thr Glu
285                 290                 295                 300 agc ggc tcc ttc tcc ccc ttc tac tac tcc ttc gac gcc ggc ggg atc      964
Ser Gly Ser Phe Ser Pro Phe Tyr Tyr Ser Phe Asp Ala Gly Gly Ile
                305                 310                 315 cat ttc gtc atg ctc gcc gcg tac gcc gac tac agc agg tca ggg gag     1012
His Phe Val Met Leu Ala Ala Tyr Ala Asp Tyr Ser Arg Ser Gly Glu
        320                 325                 330 cag tac aga tgg ctg aag aag gac ctg gcg aag gtg gac agg gcg gtg     1060
Gln Tyr Arg Trp Leu Lys Lys Asp Leu Ala Lys Val Asp Arg Ala Val
        335                 340                 345 acc ccc tgg ctg gtc gcc ggc tgg cac gcg cca tgg tac acc acc tac     1108
Thr Pro Trp Leu Val Ala Gly Trp His Ala Pro Trp Tyr Thr Thr Tyr
350                 355                 360 aag gct cac tac agg gag gtg gag tgc atg aga gtg gcc atg gag gag     1156
Lys Ala His Tyr Arg Glu Val Glu Cys Met Arg Val Ala Met Glu Glu
365                 370                 375                 380 ctg ctc tac tcc cac ggc ctc gac atc gcc ttc acc ggc cat gtg cac     1204
Leu Leu Tyr Ser His Gly Leu Asp Ile Ala Phe Thr Gly His Val His
                385                 390                 395 gcg tac gag cgc tcc aac cgg gtg ttc aac tac acg ctg gac ccg tgc     1252
Ala Tyr Glu Arg Ser Asn Arg Val Phe Asn Tyr Thr Leu Asp Pro Cys
        400                 405                 410 ggc gcg gtg cac atc tcg gtg ggc gac ggg ggg aac cgg gag aag atg     1300
Gly Ala Val His Ile Ser Val Gly Asp Gly Gly Asn Arg Glu Lys Met
        415                 420                 425 gcc acc acc cac gcc gac gag ccg ggg cac tgc ccg gac ccg cgg ccc     1348
Ala Thr Thr His Ala Asp Glu Pro Gly His Cys Pro Asp Pro Arg Pro
430                 435                 440 aag ccc aac gcc ttc atc ggc ggc ttc tgc gcc tcc aac ttc acg tcc     1396
Lys Pro Asn Ala Phe Ile Gly Gly Phe Cys Ala Ser Asn Phe Thr Ser
445                 450                 455                 460 ggc ccg gcc gcc ggc agg ttc tgc tgg gac cgg cag ccg gac tac agc     1444
Gly Pro Ala Ala Gly Arg Phe Cys Trp Asp Arg Gln Pro Asp Tyr Ser
                465                 470                 475
```

```
gcc tac cgg gaa agc agc ttc ggc cac ggc atc ctc gag gtg aag aac    1492
Ala Tyr Arg Glu Ser Ser Phe Gly His Gly Ile Leu Glu Val Lys Asn
            480                 485                 490 gag acg cac gct ctg tgg aga tgg cac agg aac cag gac cac tac gga    1540
Glu Thr His Ala Leu Trp Arg Trp His Arg Asn Gln Asp His Tyr Gly
        495                 500                 505 agc gcc gga gat gag att tac att gtc cgg gag ccg cac agg tgc ttg    1588
Ser Ala Gly Asp Glu Ile Tyr Ile Val Arg Glu Pro His Arg Cys Leu
    510                 515                 520 cac aag cac aac tcg acc agg ccg gca cac ggt cga caa aac acc aca    1636
His Lys His Asn Ser Thr Arg Pro Ala His Gly Arg Gln Asn Thr Thr
525                 530                 535                 540 cgg gaa tcg gga ggc taactgctgt actgctggag tagatcgcgc ggtgtaatgg    1691
Arg Glu Ser Gly Gly
                545 caactatata gacggttcgc ccaagcgtgg aaataaaaa                         1730
```

<210> SEQ ID NO 24
<211> LENGTH: 545
<212> TYPE: PRT
<213> ORGANISM: Triticum monococcum

<400> SEQUENCE: 24

```
Met Trp Trp Gly Ala Leu Gln Leu Leu Leu Leu Val Ala Ala Ala
1               5                   10                  15

Ala Glu Pro Ala Ser Thr Leu Thr Gly Pro Ser Arg Pro Val Thr Val
                20                  25                  30

Ala Leu Arg Lys Asp Arg Gly His Ala Val Asp Leu Pro Asp Thr Asp
            35                  40                  45

Pro Arg Val Gln Arg Arg Ala Thr Gly Trp Ala Pro Glu Gln Ile Thr
        50                  55                  60

Val Ala Leu Ser Ala Ala Pro Thr Ser Ala Trp Val Ser Trp Ile Thr
65                  70                  75                  80

Gly Glu Phe Gln Met Gly Gly Thr Val Lys Pro Leu His Pro Gly Thr
                85                  90                  95

Val Ala Ser Val Val Arg Tyr Gly Leu Ala Ala Asp Ser Leu Val Arg
            100                 105                 110

Glu Ala Thr Gly Asp Ala Leu Val Tyr Ser Gln Leu Tyr Pro Phe Glu
        115                 120                 125

Gly Leu Gln Asn Tyr Thr Ser Gly Ile Ile His His Val Arg Leu Gln
    130                 135                 140

Gly Leu Glu Pro Ala Thr Lys Tyr Tyr Tyr Gln Cys Gly Asp Pro Gly
145                 150                 155                 160

Ile Pro Gly Ala Met Ser Ala Val His Ala Phe Arg Thr Met Pro Ala
                165                 170                 175

Val Gly Pro Arg Ser Tyr Pro Gly Arg Ile Ala Val Val Gly Asp Leu
            180                 185                 190

Gly Leu Thr Tyr Asn Thr Thr Ser Thr Val Asp His Met Val Ser Asn
        195                 200                 205

Arg Pro Asp Leu Val Leu Leu Val Gly Asp Val Cys Tyr Ala Asn Met
    210                 215                 220

Tyr Leu Thr Asn Gly Thr Gly Ala Asp Cys Tyr Ser Cys Ala Phe Gly
225                 230                 235                 240

Lys Ser Thr Pro Ile His Glu Thr Tyr Gln Pro Arg Trp Asp Tyr Trp
                245                 250                 255

Gly Arg Tyr Met Glu Ala Val Thr Ser Gly Thr Pro Met Met Val Val
```

```
                260                 265                 270
Glu Gly Asn His Glu Ile Glu Glu Gln Ile Arg Asn Arg Thr Phe Ala
            275                 280                 285

Ala Tyr Arg Ser Arg Phe Ala Phe Pro Ser Thr Glu Ser Gly Ser Phe
        290                 295                 300

Ser Pro Phe Tyr Tyr Ser Phe Asp Ala Gly Ile His Phe Val Met
305                 310                 315                 320

Leu Ala Ala Tyr Ala Asp Tyr Ser Arg Ser Gly Glu Gln Tyr Arg Trp
                325                 330                 335

Leu Lys Lys Asp Leu Ala Lys Val Asp Arg Ala Val Thr Pro Trp Leu
            340                 345                 350

Val Ala Gly Trp His Ala Pro Trp Tyr Thr Thr Tyr Lys Ala His Tyr
        355                 360                 365

Arg Glu Val Glu Cys Met Arg Val Ala Met Glu Leu Leu Tyr Ser
370                 375                 380

His Gly Leu Asp Ile Ala Phe Thr Gly His Val His Ala Tyr Glu Arg
                385                 390                 395                 400

Ser Asn Arg Val Phe Asn Tyr Thr Leu Asp Pro Cys Gly Ala Val His
            405                 410                 415

Ile Ser Val Gly Asp Gly Gly Asn Arg Glu Lys Met Ala Thr Thr His
        420                 425                 430

Ala Asp Glu Pro Gly His Cys Pro Asp Pro Arg Pro Lys Pro Asn Ala
    435                 440                 445

Phe Ile Gly Gly Phe Cys Ala Ser Asn Phe Thr Ser Gly Pro Ala Ala
450                 455                 460

Gly Arg Phe Cys Trp Asp Arg Gln Pro Asp Tyr Ser Ala Tyr Arg Glu
465                 470                 475                 480

Ser Ser Phe Gly His Gly Ile Leu Glu Val Lys Asn Glu Thr His Ala
            485                 490                 495

Leu Trp Arg Trp His Arg Asn Gln Asp His Tyr Gly Ser Ala Gly Asp
        500                 505                 510

Glu Ile Tyr Ile Val Arg Glu Pro His Arg Cys Leu His Lys His Asn
    515                 520                 525

Ser Thr Arg Pro Ala His Gly Arg Gln Asn Thr Thr Arg Glu Ser Gly
530                 535                 540

Gly
545

<210> SEQ ID NO 25
<211> LENGTH: 1744
<212> TYPE: DNA
<213> ORGANISM: Secale cereale
<220> FEATURE:
<221> NAME/KEY: CDS
<222> LOCATION: (17)..(1639)
<223> OTHER INFORMATION: ScPAPhy_a1 phytase cDNA

<400> SEQUENCE: 25
aatgccaagc aacaac atg tgg cgg ggg tcg ctg cgg ctg ctg ctg ctg ctc      52
                Met Trp Arg Gly Ser Leu Arg Leu Leu Leu Leu Leu
                  1               5                  10 gcg gcg gcg gtg acg gcg gct gct gag ccg ggg tcg acg ctc atg ggc       100
Ala Ala Ala Val Thr Ala Ala Ala Glu Pro Gly Ser Thr Leu Met Gly
         15                  20                  25 ccg tca cgg ccg gtt acg gtg gcg ctg cgg gaa gac agg ggc cac gcg       148
Pro Ser Arg Pro Val Thr Val Ala Leu Arg Glu Asp Arg Gly His Ala
 30                  35                  40
```

-continued

```
gtg gac ctg ccg gac acg gac ccg cgg gtg cag cgc cgg gca aat ggc    196
Val Asp Leu Pro Asp Thr Asp Pro Arg Val Gln Arg Arg Ala Asn Gly
 45              50                  55                  60 tgg gct cct gag cag atc gcc gtc gcg ctc tcc gct gct ccc acc tct    244
Trp Ala Pro Glu Gln Ile Ala Val Ala Leu Ser Ala Ala Pro Thr Ser
                 65                  70                  75 gcc tgg gtc tcc tgg atc aca ggg gaa ttc cag atg ggc ggc acc gtc    292
Ala Trp Val Ser Trp Ile Thr Gly Glu Phe Gln Met Gly Gly Thr Val
             80                  85                  90 aag ccg ctg gac ccc ggc acg gtc ggt agc gtc gtg cgc tac ggg ctc    340
Lys Pro Leu Asp Pro Gly Thr Val Gly Ser Val Val Arg Tyr Gly Leu
         95                 100                 105 gcc gcc gat tct ttg gtt cgt gtg gcc acc ggc gac gcg ctc gtg tac    388
Ala Ala Asp Ser Leu Val Arg Val Ala Thr Gly Asp Ala Leu Val Tyr
     110                 115                 120 agc cag ctc tac cca ttc gag ggc ctc cag aac tac acc tcc ggc atc    436
Ser Gln Leu Tyr Pro Phe Glu Gly Leu Gln Asn Tyr Thr Ser Gly Ile
125                 130                 135                 140 atc cac cac gtc cgc ctc caa ggg ctt gag cct ggg acg aag tac tac    484
Ile His His Val Arg Leu Gln Gly Leu Glu Pro Gly Thr Lys Tyr Tyr
                145                 150                 155 tac cag tgc ggc gac ccg gcc ctc ccg ggg gcg atg agc gcc gtc cac    532
Tyr Gln Cys Gly Asp Pro Ala Leu Pro Gly Ala Met Ser Ala Val His
            160                 165                 170 gcg ttc cgg acg atg ccg gcg gtg ggg ccg cgg agc tac ccg ggg agg    580
Ala Phe Arg Thr Met Pro Ala Val Gly Pro Arg Ser Tyr Pro Gly Arg
        175                 180                 185 atc gcc gtg gtg gga gac ctc ggg ctc acg tac aac acc acc tcc acc    628
Ile Ala Val Val Gly Asp Leu Gly Leu Thr Tyr Asn Thr Thr Ser Thr
    190                 195                 200 gtg gac cac atg gtg agc aac cgg ccg gac ctg gtg gtc ctc gtc ggc    676
Val Asp His Met Val Ser Asn Arg Pro Asp Leu Val Val Leu Val Gly
205                 210                 215                 220 gac gtg agc tac gcc aac ctg tac ctc acc aac ggc acc gga gcg gac    724
Asp Val Ser Tyr Ala Asn Leu Tyr Leu Thr Asn Gly Thr Gly Ala Asp
                225                 230                 235 tgc tac tcg tgc gcg ttc ggc aag tcg acg ccc atc cac gag acg tac    772
Cys Tyr Ser Cys Ala Phe Gly Lys Ser Thr Pro Ile His Glu Thr Tyr
            240                 245                 250 cag ccg cgc tgg gac tac tgg ggg agg tac atg gag gcg gtg acg tcg    820
Gln Pro Arg Trp Asp Tyr Trp Gly Arg Tyr Met Glu Ala Val Thr Ser
        255                 260                 265 ggg acg ccg atg atg gtg gtg gag ggg aac cat gag ata gag gag cag    868
Gly Thr Pro Met Met Val Val Glu Gly Asn His Glu Ile Glu Glu Gln
    270                 275                 280 atc ggt aaa aag acg ttc gag gcg tac cgc tcc cgg ttc gcg ttc ccg    916
Ile Gly Lys Lys Thr Phe Glu Ala Tyr Arg Ser Arg Phe Ala Phe Pro
285                 290                 295                 300 tcg gcg gag agc ggg tcc ttc tcc ccc ttc tac tac tcc ttc gac gcc    964
Ser Ala Glu Ser Gly Ser Phe Ser Pro Phe Tyr Tyr Ser Phe Asp Ala
                305                 310                 315 ggc ggg atc cat ttc atc atg ctc gcc gcc tac gac gac tac agc agg   1012
Gly Gly Ile His Phe Ile Met Leu Ala Ala Tyr Asp Asp Tyr Ser Arg
            320                 325                 330 tca gga gag cag tac cga tgg ctg gag aag gac ctg tcg aag gtg gac   1060
Ser Gly Glu Gln Tyr Arg Trp Leu Glu Lys Asp Leu Ser Lys Val Asp
        335                 340                 345 agg tcg gtg acg ccg tgg ctg gtc gcc ggc tgg cac gcg cca tgg tac   1108
Arg Ser Val Thr Pro Trp Leu Val Ala Gly Trp His Ala Pro Trp Tyr
```

| | | | | | | | | | | | | | | | |
|---|---|---|---|---|---|---|---|---|---|---|---|---|---|---|---|
| | | 350 | | | | 355 | | | | | 360 | | | | |
| acc | acc | tac | aag | gct | cac | tac | agg | gag | gtg | gag | tgc | atg | aga | gtg | tcc | 1156 |
| Thr | Thr | Tyr | Lys | Ala | His | Tyr | Arg | Glu | Val | Glu | Cys | Met | Arg | Val | Ser |
| 365 | | | | 370 | | | | 375 | | | | | 380 | | |
| atg | gag | gag | ctc | ctc | tac | tcc | cac | ggc | ctc | gac | atc | gcc | ttc | acc | ggc | 1204 |
| Met | Glu | Glu | Leu | Leu | Tyr | Ser | His | Gly | Leu | Asp | Ile | Ala | Phe | Thr | Gly |
| | | | 385 | | | | | 390 | | | | | 395 | | |
| cat | gtg | cac | gcg | tac | gag | cgc | tcc | aac | cgg | gtg | ttc | aac | tac | acg | ctg | 1252 |
| His | Val | His | Ala | Tyr | Glu | Arg | Ser | Asn | Arg | Val | Phe | Asn | Tyr | Thr | Leu |
| | | | 400 | | | | 405 | | | | | 410 | | | |
| gac | ccg | tgc | ggt | gcc | gtg | cac | atc | tcg | gtg | ggc | gac | ggc | ggg | aac | cgc | 1300 |
| Asp | Pro | Cys | Gly | Ala | Val | His | Ile | Ser | Val | Gly | Asp | Gly | Gly | Asn | Arg |
| | | 415 | | | | | 420 | | | | | 425 | | | |
| gag | aag | atg | gcc | acc | acc | cac | gcc | gac | gag | ccg | ggg | cac | tgc | ccg | gac | 1348 |
| Glu | Lys | Met | Ala | Thr | Thr | His | Ala | Asp | Glu | Pro | Gly | His | Cys | Pro | Asp |
| 430 | | | | | 435 | | | | | 440 | | | | | |
| ccg | cgg | ccc | aag | ccc | aac | gcc | ttc | atc | ggc | ggc | ttc | tgc | ggc | ttt | aac | 1396 |
| Pro | Arg | Pro | Lys | Pro | Asn | Ala | Phe | Ile | Gly | Gly | Phe | Cys | Gly | Phe | Asn |
| 445 | | | | 450 | | | | | 455 | | | | | 460 | |
| ttc | acg | tcc | ggc | ccg | gcc | gcc | gga | agg | tac | tgc | tgg | gac | cgg | cag | ccg | 1444 |
| Phe | Thr | Ser | Gly | Pro | Ala | Ala | Gly | Arg | Tyr | Cys | Trp | Asp | Arg | Gln | Pro |
| | | | | 465 | | | | | 470 | | | | | 475 | |
| gac | tac | agc | gcc | tac | cgg | gag | agc | agc | ttt | ggc | cac | ggc | atc | ctc | gag | 1492 |
| Asp | Tyr | Ser | Ala | Tyr | Arg | Glu | Ser | Ser | Phe | Gly | His | Gly | Ile | Leu | Glu |
| | | | 480 | | | | | 485 | | | | | 490 | | |
| gtg | aag | aac | gag | acg | cac | gct | ctg | tgg | aga | tgg | cac | agg | aac | cag | gac | 1540 |
| Val | Lys | Asn | Glu | Thr | His | Ala | Leu | Trp | Arg | Trp | His | Arg | Asn | Gln | Asp |
| | | 495 | | | | | 500 | | | | | 505 | | | |
| atg | tac | ggg | agc | gcc | gga | gat | gag | att | tac | att | gtc | cgg | gag | ccg | gag | 1588 |
| Met | Tyr | Gly | Ser | Ala | Gly | Asp | Glu | Ile | Tyr | Ile | Val | Arg | Glu | Pro | Glu |
| | 510 | | | | | 515 | | | | | 520 | | | | |
| agg | tgc | ttg | cac | aag | cac | aag | cac | aac | tcg | acc | agg | ccg | gca | cac | ggc | 1636 |
| Arg | Cys | Leu | His | Lys | His | Lys | His | Asn | Ser | Thr | Arg | Pro | Ala | His | Gly |
| 525 | | | | 530 | | | | | 535 | | | | | 540 | |

| | | | |
|---|---|---|---|
| cga | taaacaccac gcgggaatcg ggaggttaac tgctgtactg ctggagtaga | | 1689 |
| Arg | | | |
| | tcgcgcggtg taatgacaac tatatagacg gttcgccaaa gcgtggaaat aaaaa | | 1744 |

<210> SEQ ID NO 26
<211> LENGTH: 541
<212> TYPE: PRT
<213> ORGANISM: Secale cereale

<400> SEQUENCE: 26

Met Trp Arg Gly Ser Leu Arg Leu Leu Leu Leu Ala Ala Ala Val
1               5                   10                  15

Thr Ala Ala Ala Glu Pro Gly Ser Thr Leu Met Gly Pro Ser Arg Pro
                20                  25                  30

Val Thr Val Ala Leu Arg Glu Asp Arg Gly His Ala Val Asp Leu Pro
            35                  40                  45

Asp Thr Asp Pro Arg Val Gln Arg Arg Ala Asn Gly Trp Ala Pro Glu
        50                  55                  60

Gln Ile Ala Val Ala Leu Ser Ala Pro Thr Ser Ala Trp Val Ser
65                  70                  75                  80

Trp Ile Thr Gly Glu Phe Gln Met Gly Gly Thr Val Lys Pro Leu Asp
                85                  90                  95

Pro Gly Thr Val Gly Ser Val Val Arg Tyr Gly Leu Ala Ala Asp Ser
            100                 105                 110

-continued

```
Leu Val Arg Val Ala Thr Gly Asp Ala Leu Val Tyr Ser Gln Leu Tyr
            115                 120                 125
Pro Phe Glu Gly Leu Gln Asn Tyr Thr Ser Gly Ile Ile His His Val
        130                 135                 140
Arg Leu Gln Gly Leu Glu Pro Gly Thr Lys Tyr Tyr Gln Cys Gly
145                 150                 155                 160
Asp Pro Ala Leu Pro Gly Ala Met Ser Ala Val His Ala Phe Arg Thr
                165                 170                 175
Met Pro Ala Val Gly Pro Arg Ser Tyr Pro Gly Arg Ile Ala Val Val
            180                 185                 190
Gly Asp Leu Gly Leu Thr Tyr Asn Thr Thr Ser Thr Val Asp His Met
        195                 200                 205
Val Ser Asn Arg Pro Asp Leu Val Val Leu Val Gly Asp Val Ser Tyr
    210                 215                 220
Ala Asn Leu Tyr Leu Thr Asn Gly Thr Gly Ala Asp Cys Tyr Ser Cys
225                 230                 235                 240
Ala Phe Gly Lys Ser Thr Pro Ile His Glu Thr Tyr Gln Pro Arg Trp
                245                 250                 255
Asp Tyr Trp Gly Arg Tyr Met Glu Ala Val Thr Ser Gly Thr Pro Met
            260                 265                 270
Met Val Val Glu Gly Asn His Glu Ile Glu Glu Gln Ile Gly Lys Lys
        275                 280                 285
Thr Phe Glu Ala Tyr Arg Ser Arg Phe Ala Phe Pro Ser Ala Glu Ser
    290                 295                 300
Gly Ser Phe Ser Pro Phe Tyr Tyr Ser Phe Asp Ala Gly Gly Ile His
305                 310                 315                 320
Phe Ile Met Leu Ala Ala Tyr Asp Asp Tyr Ser Arg Ser Gly Glu Gln
                325                 330                 335
Tyr Arg Trp Leu Glu Lys Asp Leu Ser Lys Val Asp Arg Ser Val Thr
            340                 345                 350
Pro Trp Leu Val Ala Gly Trp His Ala Pro Trp Tyr Thr Thr Tyr Lys
        355                 360                 365
Ala His Tyr Arg Glu Val Glu Cys Met Arg Val Ser Met Glu Glu Leu
    370                 375                 380
Leu Tyr Ser His Gly Leu Asp Ile Ala Phe Thr Gly His Val His Ala
385                 390                 395                 400
Tyr Glu Arg Ser Asn Arg Val Phe Asn Tyr Thr Leu Asp Pro Cys Gly
                405                 410                 415
Ala Val His Ile Ser Val Gly Asp Gly Gly Asn Arg Glu Lys Met Ala
            420                 425                 430
Thr Thr His Ala Asp Glu Pro Gly His Cys Pro Asp Pro Arg Pro Lys
        435                 440                 445
Pro Asn Ala Phe Ile Gly Gly Phe Cys Gly Phe Asn Phe Thr Ser Gly
    450                 455                 460
Pro Ala Ala Gly Arg Tyr Cys Trp Asp Arg Gln Pro Asp Tyr Ser Ala
465                 470                 475                 480
Tyr Arg Glu Ser Ser Phe Gly His Gly Ile Leu Glu Val Lys Asn Glu
                485                 490                 495
Thr His Ala Leu Trp Arg Trp His Arg Asn Gln Asp Met Tyr Gly Ser
            500                 505                 510
Ala Gly Asp Glu Ile Tyr Ile Val Arg Glu Pro Glu Arg Cys Leu His
        515                 520                 525
```

-continued

```
Lys His Lys His Asn Ser Thr Arg Pro Ala His Gly Arg
        530                 535                 540

<210> SEQ ID NO 27
<211> LENGTH: 1734
<212> TYPE: DNA
<213> ORGANISM: Secale cereale
<220> FEATURE:
<221> NAME/KEY: CDS
<222> LOCATION: (14)..(1630)
<223> OTHER INFORMATION: Phytase coding sequence of ScPAPhy_a2 phytase
      cDNA

<400> SEQUENCE: 27
aatgccaagc aac atg tgg ctg ggg tcg ctg cgg ctg ctg ctg ctc            49
               Met Trp Leu Gly Ser Leu Arg Leu Leu Leu Leu
                 1               5                  10 gcg gcg gcg gtg acg gcg gct gct gag ccg gcg tcc acg ctc atg ggc       97
Ala Ala Ala Val Thr Ala Ala Ala Glu Pro Ala Ser Thr Leu Met Gly
             15                  20                  25 ccg tca cgg ccg gtt acg gtg gcg ctg cgg gaa gac agg ggc cac gcg      145
Pro Ser Arg Pro Val Thr Val Ala Leu Arg Glu Asp Arg Gly His Ala
 30                  35                  40 gtg gac ctg ccg gac acg gac ccg cgg gtg cag cgc cgg gca aat ggc      193
Val Asp Leu Pro Asp Thr Asp Pro Arg Val Gln Arg Arg Ala Asn Gly
 45                  50                  55                  60 tgg gct cct gag cag atc gcc gtc gcg ctc tcc gct gct ccc acc tct      241
Trp Ala Pro Glu Gln Ile Ala Val Ala Leu Ser Ala Ala Pro Thr Ser
                 65                  70                  75 gcc tgg gtc tcc tgg atc acc ggg gaa ttc cag atg ggt ggc acc gtc      289
Ala Trp Val Ser Trp Ile Thr Gly Glu Phe Gln Met Gly Gly Thr Val
             80                  85                  90 aag ccg ctg gac ccc ggc acg gtc ggt agc gtc gtg cgc tac gga ctc      337
Lys Pro Leu Asp Pro Gly Thr Val Gly Ser Val Val Arg Tyr Gly Leu
         95                 100                 105 gcc gcc gat tct ttg gtt cgc gtg gcc acc ggc gac gcg ctc gtg tac      385
Ala Ala Asp Ser Leu Val Arg Val Ala Thr Gly Asp Ala Leu Val Tyr
     110                 115                 120 agc cag ctc tac ccc ttc gag ggc ctc cag aac tac acc tcc ggc atc      433
Ser Gln Leu Tyr Pro Phe Glu Gly Leu Gln Asn Tyr Thr Ser Gly Ile
125                 130                 135                 140 atc cac cac gtc cgc ctc caa ggg ctt gag cct ggg acg aag tac tac      481
Ile His His Val Arg Leu Gln Gly Leu Glu Pro Gly Thr Lys Tyr Tyr
                145                 150                 155 tac cag tgc ggc gac ccg gcc ctc ccg ggg acg atg agc gcc gtc cac      529
Tyr Gln Cys Gly Asp Pro Ala Leu Pro Gly Thr Met Ser Ala Val His
            160                 165                 170 gcg ttc cgg acg atg ccg gcg gtc ggg ccg cgg agc tac ccg ggg agg      577
Ala Phe Arg Thr Met Pro Ala Val Gly Pro Arg Ser Tyr Pro Gly Arg
        175                 180                 185 atc gcc gtg gtg gga gac ctc ggg ctc acg tac aac acc acc tcc acc      625
Ile Ala Val Val Gly Asp Leu Gly Leu Thr Tyr Asn Thr Thr Ser Thr
    190                 195                 200 gtg gac cac atg atg agc aac cgg ccg gat ctg gtc gtc ctc gtc ggc      673
Val Asp His Met Met Ser Asn Arg Pro Asp Leu Val Val Leu Val Gly
205                 210                 215                 220 gac gtg agc tac gcc aac ctg tac ctc acc aac ggc acc gga gcg gac      721
Asp Val Ser Tyr Ala Asn Leu Tyr Leu Thr Asn Gly Thr Gly Ala Asp
                225                 230                 235 tgc tac tcg tgc gcg ttc ggc aag tcg acg ccc atc cac gag acg tac      769
Cys Tyr Ser Cys Ala Phe Gly Lys Ser Thr Pro Ile His Glu Thr Tyr
            240                 245                 250
```

| | | |
|---|---|---|
| cag ccg cgc tgg gac tac tgg gga agg tac atg gag gcg gtg acg tcg<br>Gln Pro Arg Trp Asp Tyr Trp Gly Arg Tyr Met Glu Ala Val Thr Ser<br>255 260 265 | 817 | |
| ggc acg ccg atg atg gtg gtg gag ggg aac cat gag ata gag gag cag<br>Gly Thr Pro Met Met Val Val Glu Gly Asn His Glu Ile Glu Glu Gln<br>270 275 280 | 865 | |
| atc ggc aaa aag acg ttc gag gcg tac cgc tcc cgg ttc gcg ttt ccg<br>Ile Gly Lys Lys Thr Phe Glu Ala Tyr Arg Ser Arg Phe Ala Phe Pro<br>285 290 295 300 | 913 | |
| tcg gcg gag aac ggg tcc ttc tcc ccc ttc tac tac tcc ttc gac gcc<br>Ser Ala Glu Asn Gly Ser Phe Ser Pro Phe Tyr Tyr Ser Phe Asp Ala<br>305 310 315 | 961 | |
| ggc ggg atc cat ttc atc atg ctc gcc gcc tac gcc gac tac agc aag<br>Gly Gly Ile His Phe Ile Met Leu Ala Ala Tyr Ala Asp Tyr Ser Lys<br>320 325 330 | 1009 | |
| tca ggg gag cag tac aga tgg ctg gag aag gac ctg gca aag gtg gac<br>Ser Gly Glu Gln Tyr Arg Trp Leu Glu Lys Asp Leu Ala Lys Val Asp<br>335 340 345 | 1057 | |
| agg tcg gtg acg ccg tgg ctg gtc gcc ggc tgg cac gcg cca tgg tac<br>Arg Ser Val Thr Pro Trp Leu Val Ala Gly Trp His Ala Pro Trp Tyr<br>350 355 360 | 1105 | |
| acc acc tac aag gct cac tac agg gag gtg gag tgc atg aga gtg gcc<br>Thr Thr Tyr Lys Ala His Tyr Arg Glu Val Glu Cys Met Arg Val Ala<br>365 370 375 380 | 1153 | |
| atg gag gag ctg ctc tac tcc cac ggc ctg gac atc gct ttc acc ggc<br>Met Glu Glu Leu Leu Tyr Ser His Gly Leu Asp Ile Ala Phe Thr Gly<br>385 390 395 | 1201 | |
| cat gtg cac gcg tac gag cgc tcc aac cgg gtg ttc aac tac acg ctg<br>His Val His Ala Tyr Glu Arg Ser Asn Arg Val Phe Asn Tyr Thr Leu<br>400 405 410 | 1249 | |
| gat ccg tgc ggc gcc gtg cac atc tcg gtg ggc gac ggc ggg aac cgc<br>Asp Pro Cys Gly Ala Val His Ile Ser Val Gly Asp Gly Gly Asn Arg<br>415 420 425 | 1297 | |
| gag aag atg gcc acc acc cac gcc gac gag ccg ggg cac tgc ccg gac<br>Glu Lys Met Ala Thr Thr His Ala Asp Glu Pro Gly His Cys Pro Asp<br>430 435 440 | 1345 | |
| ccg cgg ccc aag ccc aac gcc ttc atc ggc ggc ttc tgc ggc ttt aac<br>Pro Arg Pro Lys Pro Asn Ala Phe Ile Gly Gly Phe Cys Gly Phe Asn<br>445 450 455 460 | 1393 | |
| ttc acg tcc ggc ccg gcc gcc ggc agg tac tgc tgg gac cgg cag ccg<br>Phe Thr Ser Gly Pro Ala Ala Gly Arg Tyr Cys Trp Asp Arg Gln Pro<br>465 470 475 | 1441 | |
| gac tac agc gcc tac cgg gag agc agc ttc ggc cac ggc atc ctc gag<br>Asp Tyr Ser Ala Tyr Arg Glu Ser Ser Phe Gly His Gly Ile Leu Glu<br>480 485 490 | 1489 | |
| gtg aag aac gag acg cac gct ctg tgg aga tgg cac agg aac cag gac<br>Val Lys Asn Glu Thr His Ala Leu Trp Arg Trp His Arg Asn Gln Asp<br>495 500 505 | 1537 | |
| atg tac ggg agc gcc gga gat gag att tac att gtc cgg gag ccg gag<br>Met Tyr Gly Ser Ala Gly Asp Glu Ile Tyr Ile Val Arg Glu Pro Glu<br>510 515 520 | 1585 | |
| agg tgc ttg cac aag cac aac tcg acc agg ccg gca cac ggc cga<br>Arg Cys Leu His Lys His Asn Ser Thr Arg Pro Ala His Gly Arg<br>525 530 535 | 1630 | |
| taaacaccac gcgggaatcg ggagcttaac tgctgtactg ctggagtaga tcgcgcggtg | 1690 | |
| taatgataac tatatagacg gttcgcccaa gcgtggaaat aaaa | 1734 | |

<210> SEQ ID NO 28

```
<211> LENGTH: 539
<212> TYPE: PRT
<213> ORGANISM: Secale cereale

<400> SEQUENCE: 28
```

Met Trp Leu Gly Ser Leu Arg Leu Leu Leu Leu Ala Ala Val
1               5                   10                  15

Thr Ala Ala Glu Pro Ala Ser Thr Leu Met Gly Pro Ser Arg Pro
            20                  25                  30

Val Thr Val Ala Leu Arg Glu Asp Arg Gly His Ala Val Asp Leu Pro
            35                  40                  45

Asp Thr Asp Pro Arg Val Gln Arg Arg Ala Asn Gly Trp Ala Pro Glu
50                  55                  60

Gln Ile Ala Val Ala Leu Ser Ala Ala Pro Thr Ser Ala Trp Val Ser
65                  70                  75                  80

Trp Ile Thr Gly Glu Phe Gln Met Gly Gly Thr Val Lys Pro Leu Asp
                85                  90                  95

Pro Gly Thr Val Gly Ser Val Val Arg Tyr Gly Leu Ala Ala Asp Ser
            100                 105                 110

Leu Val Arg Val Ala Thr Gly Asp Ala Leu Val Tyr Ser Gln Leu Tyr
            115                 120                 125

Pro Phe Glu Gly Leu Gln Asn Tyr Thr Ser Gly Ile Ile His His Val
130                 135                 140

Arg Leu Gln Gly Leu Glu Pro Gly Thr Lys Tyr Tyr Gln Cys Gly
145                 150                 155                 160

Asp Pro Ala Leu Pro Gly Thr Met Ser Ala Val His Ala Phe Arg Thr
                165                 170                 175

Met Pro Ala Val Gly Pro Arg Ser Tyr Pro Gly Arg Ile Ala Val Val
            180                 185                 190

Gly Asp Leu Gly Leu Thr Tyr Asn Thr Thr Ser Thr Val Asp His Met
            195                 200                 205

Met Ser Asn Arg Pro Asp Leu Val Val Leu Val Gly Asp Val Ser Tyr
210                 215                 220

Ala Asn Leu Tyr Leu Thr Asn Gly Thr Gly Ala Asp Cys Tyr Ser Cys
225                 230                 235                 240

Ala Phe Gly Lys Ser Thr Pro Ile His Glu Thr Tyr Gln Pro Arg Trp
                245                 250                 255

Asp Tyr Trp Gly Arg Tyr Met Glu Ala Val Thr Ser Gly Thr Pro Met
            260                 265                 270

Met Val Val Glu Gly Asn His Glu Ile Glu Glu Gln Ile Gly Lys Lys
            275                 280                 285

Thr Phe Glu Ala Tyr Arg Ser Arg Phe Ala Phe Pro Ser Ala Glu Asn
290                 295                 300

Gly Ser Phe Ser Pro Phe Tyr Ser Phe Asp Ala Gly Ile His
305                 310                 315                 320

Phe Ile Met Leu Ala Ala Tyr Ala Asp Tyr Ser Lys Ser Gly Glu Gln
                325                 330                 335

Tyr Arg Trp Leu Glu Lys Asp Leu Ala Lys Val Asp Arg Ser Val Thr
            340                 345                 350

Pro Trp Leu Val Ala Gly Trp His Ala Pro Trp Tyr Thr Thr Tyr Lys
            355                 360                 365

Ala His Tyr Arg Glu Val Glu Cys Met Arg Val Ala Met Glu Glu Leu
370                 375                 380

Leu Tyr Ser His Gly Leu Asp Ile Ala Phe Thr Gly His Val His Ala

-continued

```
             385                 390                 395                 400
Tyr Glu Arg Ser Asn Arg Val Phe Asn Tyr Thr Leu Asp Pro Cys Gly
                    405                 410                 415

Ala Val His Ile Ser Val Gly Asp Gly Gly Asn Arg Glu Lys Met Ala
                420                 425                 430

Thr Thr His Ala Asp Glu Pro Gly His Cys Pro Asp Pro Arg Pro Lys
            435                 440                 445

Pro Asn Ala Phe Ile Gly Gly Phe Cys Gly Phe Asn Phe Thr Ser Gly
450                 455                 460

Pro Ala Ala Gly Arg Tyr Cys Trp Asp Arg Gln Pro Asp Tyr Ser Ala
465                 470                 475                 480

Tyr Arg Glu Ser Ser Phe Gly His Gly Ile Leu Glu Val Lys Asn Glu
                485                 490                 495

Thr His Ala Leu Trp Arg Trp His Arg Asn Gln Asp Met Tyr Gly Ser
            500                 505                 510

Ala Gly Asp Glu Ile Tyr Ile Val Arg Glu Pro Glu Arg Cys Leu His
        515                 520                 525

Lys His Asn Ser Thr Arg Pro Ala His Gly Arg
        530                 535

<210> SEQ ID NO 29
<211> LENGTH: 1773
<212> TYPE: DNA
<213> ORGANISM: Hordeum vulgare
<220> FEATURE:
<221> NAME/KEY: CDS
<222> LOCATION: (40)..(1650)
<223> OTHER INFORMATION: Phytase coding sequence of HvPAPhy_a1 phytase
      cDNA

<400> SEQUENCE: 29
agcatcccaa tcctctcaat gccaagcaac aacatcaac atg tgg tgg ggg tcg        54
                                             Met Trp Trp Gly Ser
                                             1               5 ctg ctg ctg ctc gcg gcg gcg gtg gcg gtg gct gcc gct gag ccg ccg     102
Leu Leu Leu Leu Ala Ala Ala Val Ala Val Ala Ala Ala Glu Pro Pro
            10                  15                  20 tcg acg ctc gct ggc ccg tcg cgg ccg gtg acg gtg acg ccg cgg gaa     150
Ser Thr Leu Ala Gly Pro Ser Arg Pro Val Thr Val Thr Pro Arg Glu
        25                  30                  35 aac agg ggc cac gcg gtg gac ctg ccg gac acg gac ccc cgg gtg cag     198
Asn Arg Gly His Ala Val Asp Leu Pro Asp Thr Asp Pro Arg Val Gln
    40                  45                  50 cgc cgg gcc acg ggc tgg gct ccc gag cag gtc gcc gtc gcg ctc tcc     246
Arg Arg Ala Thr Gly Trp Ala Pro Glu Gln Val Ala Val Ala Leu Ser
55                  60                  65 gcc gct ccc acc tct gcc tgg gtc tcc tgg atc acc ggg gaa ttc cag     294
Ala Ala Pro Thr Ser Ala Trp Val Ser Trp Ile Thr Gly Glu Phe Gln
70                  75                  80                  85 atg ggc ggc acc gtg aag ccg ctg gac ccc cgc acg gtc ggc agc gtc     342
Met Gly Gly Thr Val Lys Pro Leu Asp Pro Arg Thr Val Gly Ser Val
                90                  95                  100 gtg cgc tac ggg ctc gcc gcc gac tct ttg gtt cgc gag gcc acc ggc     390
Val Arg Tyr Gly Leu Ala Ala Asp Ser Leu Val Arg Glu Ala Thr Gly
            105                 110                 115 gac gcg ctc gtg tac agc cag ctc tac ccc ttc gag ggc ctc cac aac     438
Asp Ala Leu Val Tyr Ser Gln Leu Tyr Pro Phe Glu Gly Leu His Asn
        120                 125                 130 tac acc tcc ggc atc atc cac cac gtc cgc ctc caa ggg ctt gag cct     486
```

|  |  |  |  |  |  |  |  |  |  |  |  |  |  |
|---|---|---|---|---|---|---|---|---|---|---|---|---|---|
| Tyr | Thr | Ser | Gly | Ile | Ile | His | His | Val | Arg | Leu | Gln | Gly | Leu | Glu | Pro |
|  |  |  | 135 |  |  |  | 140 |  |  |  | 145 |  |  |  |  |

```
ggg acc aag tac tac tac cag tgc ggc gac ccg gcc atc ccg ggg gcg    534
Gly Thr Lys Tyr Tyr Tyr Gln Cys Gly Asp Pro Ala Ile Pro Gly Ala
150                 155                 160                 165 atg agc gcc gtc cac gcg ttc cgg acg atg ccg gcg gcg ggg ccg cgg    582
Met Ser Ala Val His Ala Phe Arg Thr Met Pro Ala Ala Gly Pro Arg
                170                 175                 180 agc tac ccg ggg agg atc gcc gtg gtg gga gac ctc ggg ctc acg tac    630
Ser Tyr Pro Gly Arg Ile Ala Val Val Gly Asp Leu Gly Leu Thr Tyr
            185                 190                 195 aac acc acc tcg acc gtg gac cac atg acg agc aac cgg ccg gac ctg    678
Asn Thr Thr Ser Thr Val Asp His Met Thr Ser Asn Arg Pro Asp Leu
        200                 205                 210 gtc gtc ctc gtc ggc gac gtc agc tac gcc aac atg tac ctc acc aac    726
Val Val Leu Val Gly Asp Val Ser Tyr Ala Asn Met Tyr Leu Thr Asn
    215                 220                 225 ggc acc gga acg gac tgc tac tcc tgc tcc ttc ggc aag tca acg ccc    774
Gly Thr Gly Thr Asp Cys Tyr Ser Cys Ser Phe Gly Lys Ser Thr Pro
230                 235                 240                 245 atc cac gaa acc tac cag ccg cgc tgg gac tac tgg gga agg tac atg    822
Ile His Glu Thr Tyr Gln Pro Arg Trp Asp Tyr Trp Gly Arg Tyr Met
                250                 255                 260 gag ccg gtg acg tcg agc acg ccg atg atg gtg gtg gaa ggg aac cac    870
Glu Pro Val Thr Ser Ser Thr Pro Met Met Val Val Glu Gly Asn His
            265                 270                 275 gag ata gag gag cag atc ggc aac aag acg ttc gcg gcc tac cgc tcc    918
Glu Ile Glu Glu Gln Ile Gly Asn Lys Thr Phe Ala Ala Tyr Arg Ser
        280                 285                 290 cgg ttc gcg ttc ccg tcg gcg gag agc ggg tcc ttc tcc ccc ttc tac    966
Arg Phe Ala Phe Pro Ser Ala Glu Ser Gly Ser Phe Ser Pro Phe Tyr
    295                 300                 305 tac tcc ttc gac gcc ggc ggg atc cac ttc atc atg ctc ggc gcc tac   1014
Tyr Ser Phe Asp Ala Gly Gly Ile His Phe Ile Met Leu Gly Ala Tyr
310                 315                 320                 325 gcc gac tac ggc agg tca ggg gag cag tac aga tgg ctg gag aag gac   1062
Ala Asp Tyr Gly Arg Ser Gly Glu Gln Tyr Arg Trp Leu Glu Lys Asp
                330                 335                 340 ctg gcg aag gtg gac agg tcg gtg acc ccc tgg ctg gtg gcc ggc tgg   1110
Leu Ala Lys Val Asp Arg Ser Val Thr Pro Trp Leu Val Ala Gly Trp
            345                 350                 355 cac gcg cca tgg tac acc acg tac aag gct cac tac agg gag gtg gag   1158
His Ala Pro Trp Tyr Thr Thr Tyr Lys Ala His Tyr Arg Glu Val Glu
        360                 365                 370 tgc atg aga gtg gcc atg gag gag ctc ctc tac tcc cac ggc ctc gac   1206
Cys Met Arg Val Ala Met Glu Glu Leu Leu Tyr Ser His Gly Leu Asp
    375                 380                 385 atc gcc ttc acc ggc cat gtg cac gcg tac gag cgc tcc aac cgg gtg   1254
Ile Ala Phe Thr Gly His Val His Ala Tyr Glu Arg Ser Asn Arg Val
390                 395                 400                 405 ttc aac tac acg ctg gac ccg tgc ggc gcc gtg tac atc tcg gtg ggc   1302
Phe Asn Tyr Thr Leu Asp Pro Cys Gly Ala Val Tyr Ile Ser Val Gly
                410                 415                 420 gac ggc ggg aac cgg gag aag atg gcc acc acc cac gcc gac gag ccg   1350
Asp Gly Gly Asn Arg Glu Lys Met Ala Thr Thr His Ala Asp Glu Pro
            425                 430                 435 ggg cac tgc ccg gac ccg cgg cca aag ccc aac gcc ttc att gcc ggc   1398
Gly His Cys Pro Asp Pro Arg Pro Lys Pro Asn Ala Phe Ile Ala Gly
        440                 445                 450
```

```
ttc tgc gcc ttt aac ttc acg tcc ggc ccg gcc gcc ggc agg ttc tgc      1446
Phe Cys Ala Phe Asn Phe Thr Ser Gly Pro Ala Ala Gly Arg Phe Cys
    455                 460                 465 tgg gac cgg cag ccg gac tac agc gcg tac cgg gag agc agc ttc ggc      1494
Trp Asp Arg Gln Pro Asp Tyr Ser Ala Tyr Arg Glu Ser Ser Phe Gly
470                 475                 480                 485 cat ggc atc ctc gag gtg aag aac gag acg cac gct ctg tgg aga tgg      1542
His Gly Ile Leu Glu Val Lys Asn Glu Thr His Ala Leu Trp Arg Trp
                490                 495                 500 cac agg aac cag gac ctg tac ggg agc gcc gga gat gag att tac att      1590
His Arg Asn Gln Asp Leu Tyr Gly Ser Ala Gly Asp Glu Ile Tyr Ile
            505                 510                 515 gtt cgg gag ccg gag agg tgc ttg cac aag cac aac tcg acc agg ccc      1638
Val Arg Glu Pro Glu Arg Cys Leu His Lys His Asn Ser Thr Arg Pro
        520                 525                 530 gca cac ggt ccg taaaaatggc aactacagac ggttcgccca agccggagat          1690
Ala His Gly Pro
            535 taactgttct accactactg gagtatatcg ccccgtgcaa taatggcaac tatagacggt    1750 tcgcccatgc gtggaaataa aaa                                            1773

<210> SEQ ID NO 30
<211> LENGTH: 537
<212> TYPE: PRT
<213> ORGANISM: Hordeum vulgare

<400> SEQUENCE: 30

Met Trp Trp Gly Ser Leu Leu Leu Ala Ala Val Ala Val Ala
1               5                   10                  15

Ala Ala Glu Pro Pro Ser Thr Leu Ala Gly Pro Ser Arg Pro Val Thr
            20                  25                  30

Val Thr Pro Arg Glu Asn Arg Gly His Ala Val Asp Leu Pro Asp Thr
        35                  40                  45

Asp Pro Arg Val Gln Arg Arg Ala Thr Gly Trp Ala Pro Glu Gln Val
    50                  55                  60

Ala Val Ala Leu Ser Ala Ala Pro Thr Ser Ala Trp Val Ser Trp Ile
65                  70                  75                  80

Thr Gly Glu Phe Gln Met Gly Gly Thr Val Lys Pro Leu Asp Pro Arg
                85                  90                  95

Thr Val Gly Ser Val Val Arg Tyr Gly Leu Ala Ala Asp Ser Leu Val
            100                 105                 110

Arg Glu Ala Thr Gly Asp Ala Leu Val Tyr Ser Gln Leu Tyr Pro Phe
        115                 120                 125

Glu Gly Leu His Asn Tyr Thr Ser Gly Ile Ile His His Val Arg Leu
    130                 135                 140

Gln Gly Leu Glu Pro Gly Thr Lys Tyr Tyr Gln Cys Gly Asp Pro
145                 150                 155                 160

Ala Ile Pro Gly Ala Met Ser Ala Val His Ala Phe Arg Thr Met Pro
                165                 170                 175

Ala Ala Gly Pro Arg Ser Tyr Pro Gly Arg Ile Ala Val Val Gly Asp
            180                 185                 190

Leu Gly Leu Thr Tyr Asn Thr Thr Ser Thr Val Asp His Met Thr Ser
        195                 200                 205

Asn Arg Pro Asp Leu Val Val Leu Val Gly Asp Val Ser Tyr Ala Asn
    210                 215                 220

Met Tyr Leu Thr Asn Gly Thr Gly Thr Asp Cys Tyr Ser Cys Ser Phe
```

```
            225                 230                 235                 240
         Gly Lys Ser Thr Pro Ile His Glu Thr Tyr Gln Pro Arg Trp Asp Tyr
                         245                 250                 255
         Trp Gly Arg Tyr Met Glu Pro Val Thr Ser Thr Pro Met Met Val
                         260                 265                 270
         Val Glu Gly Asn His Glu Ile Glu Glu Gln Ile Gly Asn Lys Thr Phe
                         275                 280                 285
         Ala Ala Tyr Arg Ser Arg Phe Ala Phe Pro Ser Ala Glu Ser Gly Ser
                         290                 295                 300
         Phe Ser Pro Phe Tyr Tyr Ser Phe Asp Ala Gly Ile His Phe Ile
         305                 310                 315                 320
         Met Leu Gly Ala Tyr Ala Asp Tyr Gly Arg Ser Gly Glu Gln Tyr Arg
                         325                 330                 335
         Trp Leu Glu Lys Asp Leu Ala Lys Val Asp Arg Ser Val Thr Pro Trp
                         340                 345                 350
         Leu Val Ala Gly Trp His Ala Pro Trp Tyr Thr Thr Tyr Lys Ala His
                         355                 360                 365
         Tyr Arg Glu Val Glu Cys Met Arg Val Ala Met Glu Glu Leu Leu Tyr
                         370                 375                 380
         Ser His Gly Leu Asp Ile Ala Phe Thr Gly His Val His Ala Tyr Glu
         385                 390                 395                 400
         Arg Ser Asn Arg Val Phe Asn Tyr Thr Leu Asp Pro Cys Gly Ala Val
                         405                 410                 415
         Tyr Ile Ser Val Gly Asp Gly Gly Asn Arg Glu Lys Met Ala Thr Thr
                         420                 425                 430
         His Ala Asp Glu Pro Gly His Cys Pro Asp Pro Arg Pro Lys Pro Asn
                         435                 440                 445
         Ala Phe Ile Ala Gly Phe Cys Ala Phe Asn Phe Thr Ser Gly Pro Ala
                         450                 455                 460
         Ala Gly Arg Phe Cys Trp Asp Arg Gln Pro Asp Tyr Ser Ala Tyr Arg
         465                 470                 475                 480
         Glu Ser Ser Phe Gly His Gly Ile Leu Glu Val Lys Asn Glu Thr His
                         485                 490                 495
         Ala Leu Trp Arg Trp His Arg Asn Gln Asp Leu Tyr Gly Ser Ala Gly
                         500                 505                 510
         Asp Glu Ile Tyr Ile Val Arg Glu Pro Glu Arg Cys Leu His Lys His
                         515                 520                 525
         Asn Ser Thr Arg Pro Ala His Gly Pro
                         530                 535

<210> SEQ ID NO 31
<211> LENGTH: 19
<212> TYPE: DNA
<213> ORGANISM: Triticum sp.
<220> FEATURE:
<221> NAME/KEY: primer_bind
<222> LOCATION: (1)..(19)
<223> OTHER INFORMATION: Triticum spp PAPhy gene forward primer:
      PAP ex3 Fw primer

<400> SEQUENCE: 31
cttgagcctg ggacgaagt                                                    19

<210> SEQ ID NO 32
<211> LENGTH: 18
<212> TYPE: DNA
<213> ORGANISM: Triticum sp.
```

```
<220> FEATURE:
<221> NAME/KEY: primer_bind
<222> LOCATION: (1)..(18)
<223> OTHER INFORMATION: Triticum spp PAPhy gene reverse primer:
      PAP ex3 Rv primer

<400> SEQUENCE: 32
gagaaggacc cgctctcc                                                     18

<210> SEQ ID NO 33
<211> LENGTH: 20
<212> TYPE: DNA
<213> ORGANISM: Triticum sp.
<220> FEATURE:
<221> NAME/KEY: primer_bind
<222> LOCATION: (1)..(20)
<223> OTHER INFORMATION: Triticum spp PAPhy promoter forward primer:
      TaPAPhy_a1-pro-ex1 Fw

<400> SEQUENCE: 33
ttatgtgtcc gcgtgaagtg                                                   20

<210> SEQ ID NO 34
<211> LENGTH: 20
<212> TYPE: DNA
<213> ORGANISM: Triticum sp.
<220> FEATURE:
<221> NAME/KEY: primer_bind
<222> LOCATION: (1)..(20)
<223> OTHER INFORMATION: Triticum spp PAPhy promoter reverse primer:
      TaPAPhy_a1-pro-ex1 Rv

<400> SEQUENCE: 34
accaagagtc aatgccatcc                                                   20

<210> SEQ ID NO 35
<211> LENGTH: 23
<212> TYPE: DNA
<213> ORGANISM: Triticum sp.
<220> FEATURE:
<221> NAME/KEY: primer_bind
<222> LOCATION: (1)..(23)
<223> OTHER INFORMATION: Triticum spp PAPhy promoter forward primer
      2: TaPAPhy_a1 -311 cons Fw

<400> SEQUENCE: 35
tttggacgag ccatagctgc ata                                               23

<210> SEQ ID NO 36
<211> LENGTH: 20
<212> TYPE: DNA
<213> ORGANISM: Triticum sp.
<220> FEATURE:
<221> NAME/KEY: primer_bind
<222> LOCATION: (1)..(20)
<223> OTHER INFORMATION: Triticum spp PAPhy promoter reverse primer
      2: TaPAPhy_a1 167 Rv

<400> SEQUENCE: 36
cgctgcaccc gggggtccgt                                                   20

<210> SEQ ID NO 37
<211> LENGTH: 22
<212> TYPE: DNA
<213> ORGANISM: Triticum sp.
<220> FEATURE:
<221> NAME/KEY: primer_bind
<222> LOCATION: (1)..(22)
<223> OTHER INFORMATION: Triticum spp PAPhy enhancer forward primer:
```

AS-PCR enhancer forward primer

<400> SEQUENCE: 37
caagctacac tttgtagaac ac                                              22

<210> SEQ ID NO 38
<211> LENGTH: 20
<212> TYPE: DNA
<213> ORGANISM: Triticum sp.
<220> FEATURE:
<221> NAME/KEY: primer_bind
<222> LOCATION: (1)..(20)
<223> OTHER INFORMATION: Triticum spp PAPhy gene reverse primer:
      AS-PCR enhancer reverse primer

<400> SEQUENCE: 38
cgctgcaccc gggggtccgt                                                 20

<210> SEQ ID NO 39
<211> LENGTH: 25
<212> TYPE: DNA
<213> ORGANISM: Triticum sp.
<220> FEATURE:
<221> NAME/KEY: primer_bind
<222> LOCATION: (1)..(25)
<223> OTHER INFORMATION: HighPhy SNP forward primer

<400> SEQUENCE: 39
tttcaagcta cactttgtag aacac                                           25

<210> SEQ ID NO 40
<211> LENGTH: 20
<212> TYPE: DNA
<213> ORGANISM: Triticum sp.
<220> FEATURE:
<221> NAME/KEY: primer_bind
<222> LOCATION: (1)..(20)
<223> OTHER INFORMATION: HighPhy SNP reverse primer

<400> SEQUENCE: 40
gcactagcca agtttggacg                                                 20

<210> SEQ ID NO 41
<211> LENGTH: 25
<212> TYPE: DNA
<213> ORGANISM: Triticum sp.
<220> FEATURE:
<221> NAME/KEY: primer_bind
<222> LOCATION: (1)..(25)
<223> OTHER INFORMATION: Wildtype Phy SNP forward primer

<400> SEQUENCE: 41
tttcaagcta cactttgtag aacat                                           25

<210> SEQ ID NO 42
<211> LENGTH: 20
<212> TYPE: DNA
<213> ORGANISM: Triticum sp.
<220> FEATURE:
<221> NAME/KEY: primer_bind
<222> LOCATION: (1)..(20)
<223> OTHER INFORMATION: Wildtype Phy SNP reverse primer

<400> SEQUENCE: 42
gcactagcca agtttggacg                                                 20

<210> SEQ ID NO 43

```
<211> LENGTH: 2090
<212> TYPE: DNA
<213> ORGANISM: Triticum aestivum
<220> FEATURE:
<221> NAME/KEY: promoter
<222> LOCATION: (1)..(2090)
<223> OTHER INFORMATION: Wild type TaPAPhy-a1 promoter and 5'
      untranslated region
<220> FEATURE:
<221> NAME/KEY: enhancer
<222> LOCATION: (1845)..(1859)
<223> OTHER INFORMATION: wild type cereal enhancer

<400> SEQUENCE: 43
```

| | | | | | |
|---|---|---|---|---|---|
| aactcatgct | cctaatgtga | agcataaaat | tatgtgtccg | cgtgaagtgc | atgtgtactc | 60 |
| catgaaaaac | ctataaaatg | agaaaaccca | aaaaaactag | aaaaatcttt | gcaaaatcca | 120 |
| aaaacctaaa | aaaaatcccc | caaaaaagat | tcatgtggag | gtgtacgcta | tgtggcgaca | 180 |
| actgaatgca | ccacgtggcg | cggtcgtgtg | ctcacaccgg | ggaaagtgcc | accgtggggt | 240 |
| accccctaat | tatttgctcc | aaaagtttgt | tgctttgtaa | aaaagttata | aatcaaacat | 300 |
| aatgggcctg | atctcattca | gctcgaactc | cacacacaaa | gctagatcga | atgctctaac | 360 |
| tttgcgaagc | tggaatccat | cgtctccaag | aggcctagtg | cgattttttcg | aagctagtat | 420 |
| ttcatgattt | aaaaattcac | tatgtttatg | aacaactctc | gactagagag | tattcttagt | 480 |
| aatgtgataa | gagtaacaca | acgattttt | taatataggt | ttggtttgca | attgtattga | 540 |
| tagagcgaga | cctaatccta | tttgggaagg | cctcaggtag | ttaggacggt | tgtagctcag | 600 |
| tcgaggtcag | tttgagtcgt | aatgcaactc | ttcgcacttg | acttcaaaat | gacttggggc | 660 |
| tattgaaagg | tccaaaagca | acgatgtcgc | cgatgagttt | attcaaagtg | agagtacatg | 720 |
| tccatgaggc | taagagaagg | ggtgccttga | caaattatca | agactgcacc | aaggcgatgg | 780 |
| taggatatga | gaggtatgat | gataagtcta | tatccatgag | tccataaaag | tagtcaaagg | 840 |
| tggatccata | gtccatggta | cattaatcat | tttcatccat | gtgtgaatgg | acctttagct | 900 |
| agttgggcct | catttagatt | tgggctcatt | tccttctata | cttcattctt | gactctcttt | 960 |
| ttttttgcga | aaaggattag | atctcttata | aaaattcatc | ggaggtacaa | agtatctcaa | 1020 |
| acataataaa | aactacatcg | agattccgag | accaacgaac | gaccaccact | gccactagaa | 1080 |
| taagctgctg | acgcgccacc | ggagccgcct | tgaccttgtc | aatgacagcc | gggaagtctt | 1140 |
| cacgcacgta | cccctaagga | ccaacgctct | ggagtcgcag | tcgtcgccat | tgaacgcttg | 1200 |
| catagatctg | aagcatttga | caccaaatct | cgccacatga | cgagaaaacg | ctaaccccac | 1260 |
| cgccccaaga | agacaacaag | aatctatgtc | ggagctccgt | caactaccca | gatgagtgaa | 1320 |
| ctcgaggagg | atcggagccc | ggaagacaaa | ctcgaagaag | aagccttgcc | atccacccga | 1380 |
| aggccgcacc | tatgaggact | aaaaaaacct | aacctaattt | tttttgataa | agaagggtt | 1440 |
| ttccccttcc | gattttcatt | aaagaaaacc | aaaccaaacc | taaactacta | accggagcga | 1500 |
| aggcatcggg | attctcgtcc | gcgccaccgg | ccgccggagc | ggtaggcaga | gtggaggcaa | 1560 |
| atccacggac | tcaccggtga | agtctagagg | ggtctagccg | cctaggatca | ttatgggagg | 1620 |
| taaacaagag | tgatttcaat | gttgactttg | acctttcatt | ttttgccttc | tccttttatt | 1680 |
| tgttgaccat | gcaattttgc | ttggacttct | attaatcttg | ttaatggagt | tggatatatg | 1740 |
| cgttgatcgt | tttagacctt | attcaccggc | ttgaacttt | ttggacgagc | catagctgca | 1800 |
| tattttgttg | cttgcgcttt | agtttcaagc | tacactttgt | agaacatgag | tcatgcatgg | 1860 |
| gacgaaggcg | tccaaacttg | gctagtgcag | ctgcctgcgc | gttcacaagg | caccaaagcg | 1920 |

| | | |
|---|---|---|
| caggcggcaa agtttgctcg tttattatct tggcggtcca agatgggcgg caggttccag | 1980 |
| acgatggacg aagacccacc gagttccact tccggctcca acctcctctg cccgattcat | 2040 |
| ataagtttcc tgccaaaggc attccaattc tgtcaatgcc aagcaacaac | 2090 |

```
<210> SEQ ID NO 44
<211> LENGTH: 2060
<212> TYPE: DNA
<213> ORGANISM: Triticum aestivum
<220> FEATURE:
<221> NAME/KEY: promoter
<222> LOCATION: (1)..(2060)
<223> OTHER INFORMATION: HighPhy mutant TaPAPhy-a1 promoter and 5'
      untranslated region
<220> FEATURE:
<221> NAME/KEY: enhancer
<222> LOCATION: (1816)..(1829)
<223> OTHER INFORMATION: Mutant cereal Enhancer

<400> SEQUENCE: 44
```

| | | |
|---|---|---|
| ttatgtgtcc gcgtgaagtg catctgtact ccatgaaaaa cctataaaat gagaaaccc | 60 |
| aaaaaaaact agaaaatctt ttgcaaaatc caaaaaccta aaaaaaatcc cccaaaaaag | 120 |
| attcatgtgg aggtgtacgc tatgtggcga caactgaatg caccacgtgg cgcggtcgtg | 180 |
| tgctcacacc ggggaaagtg ccaccgtggg gtaccccta attatttgct ccaaaagttt | 240 |
| gttgctttgt aaaaaaaata taaatcaaac ataatgggcc tgatctcatt cagctcgaac | 300 |
| tccacacaca aagctagatc gaatgctcta actttgcgaa gctggaatcc atcgtctcca | 360 |
| agaggcctag tgcgatttt cgaagctagt atttcatgat ttaaaaattc actatgttta | 420 |
| tgaacaactc tcgactagag agtattctta gtaatgtgat aagagtaaca cagcgatttt | 480 |
| tttaatatag gttcggtttg caattgtatt gatagagcga gacctaatcc tatttgggaa | 540 |
| ggcctcaggt agttaggacg gttgtagctc agtcgaggtc agtttgagtc gtaatgcaac | 600 |
| tcttcgcact tgacttcaaa atgacttggg gctattgaaa ggtccaaaag caacgatgtc | 660 |
| gccgatgagt ttattcaaag tgagagtaca tgtccatgag gctaagagaa ggggtgcctt | 720 |
| gacaaattat caagactgca ccaaggcgat ggtaggatat gagaggtatg atgataagtc | 780 |
| tatatccatg agtccataaa agtagtcaag ggtggatcca tagtccatgg tacattaatc | 840 |
| attttcatcc atgtgtgaat ggacctttag ctagttgggc ctcatttaga tttgggctca | 900 |
| tttccttcta gacttcattc ttgactcttt ttttgcgaa aaggattaga tctcttataa | 960 |
| aaattcatcg gaggtacaaa gtatctcaaa cataataaaa actacatcga gattccgagc | 1020 |
| ccaacgaacg accaccactg ccactagaat aagctgctga cgcgccaccg gagccgcctt | 1080 |
| gaccttgtca atgacagccg ggaagtcttc acgcacgtac ccctaaggat cgacgctttg | 1140 |
| gagtcgcagt cattgccatt gaacacttgc atagatctga agcatttgac accaaatctc | 1200 |
| gccacatgac gagaaaccct aaccccaccg ccccaagaag acaacaagaa tctacgtcgg | 1260 |
| agctccgtca actacccaga tgagtgaact cgaggaggat cggagccgg aagacaaact | 1320 |
| cgaagaagaa gccttgccat ccacccgaag gccgcactta cgaggactaa aaaaacctaa | 1380 |
| cctaaattt tttttgataa aagaagggtt ttccccttcc gattttcatt aaagaaaacc | 1440 |
| aaacctaacc taaactacta accggagcga aggcatcggg attctcgtcc gcgccatcgg | 1500 |
| ccgccggagc ggtaggcaga gtggaggcaa atccacggac tcaccggtga agtctggagg | 1560 |
| ggtctagccg tctaggatca ttatgggagg taaacaagag tgattcaat gttgactttg | 1620 |
| acctttcatt ttttgccttc tcctttatt tgttgaccat gcaattttgc ttggacttct | 1680 |

| | |
|---|---|
| attaatcttg ttaatggagt tggatatatg cgttgatcgt tttagacctt attcaccggc | 1740 |
| ttgaactttt ttggacgagc catagctgca tattttgttg cttgcgcttt agtttcaagc | 1800 |
| tacactttgt agaacacgag tcatgcatgg gacgaaggcg tccaaacttg gctagtgcag | 1860 |
| ctgcctgcgc gttcacaagg caccaaagcg caggcggcaa agtttgctcg tttattatct | 1920 |
| tggcggtcca agatgggcgg caggttccag acgatggacg aagacccacc gagttccact | 1980 |
| tccggctcca acctcctctg cccgattcat ataagtttcc tgccaaaggc atcccaattc | 2040 |
| tgtcaatgcc aagcaacaac | 2060 |

```
<210> SEQ ID NO 45
<211> LENGTH: 4814
<212> TYPE: DNA
<213> ORGANISM: Triticum aestivum
<220> FEATURE:
<221> NAME/KEY: promoter
<222> LOCATION: (1)..(2090)
<223> OTHER INFORMATION: Promoter and '5' untranslated region
<220> FEATURE:
<221> NAME/KEY: exon
<222> LOCATION: (2091)..(2342)
<220> FEATURE:
<221> NAME/KEY: Intron
<222> LOCATION: (2343)..(2405)
<220> FEATURE:
<221> NAME/KEY: exon
<222> LOCATION: (2406)..(2597)
<220> FEATURE:
<221> NAME/KEY: Intron
<222> LOCATION: (2598)..(2687)
<220> FEATURE:
<221> NAME/KEY: exon
<222> LOCATION: (2688)..(3827)
<220> FEATURE:
<221> NAME/KEY: Intron
<222> LOCATION: (3828)..(3925)
<220> FEATURE:
<221> NAME/KEY: exon
<222> LOCATION: (3926)..(4090)
<220> FEATURE:
<221> NAME/KEY: 3'UTR
<222> LOCATION: (4091)..(4814)
```

<400> SEQUENCE: 45

| | |
|---|---|
| aactcatgct cctaatgtga agcataaaat tatgtgtccg cgtgaagtgc atgtgtactc | 60 |
| catgaaaaac ctataaaatg agaaaaccca aaaaaactag aaaaatcttt gcaaatcca | 120 |
| aaaacctaaa aaaaatcccc caaaaagat tcatgtggag gtgtacgcta tgtggcgaca | 180 |
| actgaatgca ccacgtggcg cggtcgtgtg ctcacaccgg ggaaagtgcc accgtggggt | 240 |
| acccccctaat tatttgctcc aaaagtttgt tgctttgtaa aaagttata aatcaaacat | 300 |
| aatgggcctg atctcattca gctcgaactc cacacacaaa gctagatcga atgctctaac | 360 |
| tttgcgaagc tggaatccat cgtctccaag aggcctagtg cgattttcg aagctagtat | 420 |
| ttcatgattt aaaaattcac tatgtttatg aacaactctc gactagagag tattcttagt | 480 |
| aatgtgataa gagtaacaca cgatttttt taatataggt ttggtttgca attgtattga | 540 |
| tagagcgaga cctaatccta tttgggaagg cctcaggtag ttaggacggt tgtagctcag | 600 |
| tcgaggtcag tttgagtcgt aatgcaactc ttcgcacttg acttcaaaat gacttggggc | 660 |
| tattgaaagg tccaaaagca acgatgtcgc cgatgagttt attcaaagtg agagtacatg | 720 |
| tccatgaggc taagagaagg ggtgccttga caaattatca agactgcacc aaggcgatgg | 780 |
| taggatatga gaggtatgat gataagtcta tatccatgag tccataaaag tagtcaaagg | 840 |
| tggatccata gtccatggta cattaatcat tttcatccat gtgtgaatgg acctttagct | 900 |

-continued

```
agttgggcct catttagatt tgggctcatt tccttctata cttcattctt gactctcttt    960
ttttttgcga aaaggattag atctcttata aaaattcatc ggaggtacaa agtatctcaa   1020
acataataaa aactacatcg agattccgag accaacgaac gaccaccact gccactagaa   1080
taagctgctg acgcgccacc ggagccgcct tgaccttgtc aatgacagcc gggaagtctt   1140
cacgcacgta ccctaagga ccaacgctct ggagtcgcag tcgtcgccat gaacgcttg    1200 catagatctg aagcatttga caccaaatct cgccacatga cgagaaaacg ctaacccac    1260 cgccccaaga agacaacaag aatctatgtc ggagctccgt caactaccca gatgagtgaa   1320
ctcgaggagg atcggagccc ggaagacaaa ctcgaagaag aagccttgcc atccacccga   1380
aggccgcacc tatgaggact aaaaaaacct aacctaattt tttttgataa agaagggtt    1440 ttccccttcc gatttttcatt aaagaaaacc aaaccaaacc taaactacta accggagcga   1500
aggcatcggg attctcgtcc gcgccaccgg ccgccggagc ggtaggcaga gtggaggcaa   1560
atccacggac tcaccggtga agtctagagg ggtctagccg cctaggatca ttatgggagg   1620
taaacaagag tgatttcaat gttgactttg acctttcatt ttttgccttc tccttttatt   1680
tgttgaccat gcaattttgc ttggacttct attaatcttg ttaatggagt tggatatatg   1740
cgttgatcgt tttagacctt attcaccggc ttgaacttt ttggacgagc catagctgca    1800
tattttgttg cttgcgcttt agtttcaagc tacactttgt agaacatgag tcatgcatgg   1860
gacgaaggcg tccaaacttg gctagtgcag ctgcctgcgc gttcacaagg caccaaagcg   1920
caggcggcaa agtttgctcg tttattatct tggcggtcca agatgggcgg caggttccag   1980
acgatggacg aagacccacc gagttccact tccggctcca acctcctctg cccgattcat   2040
ataagtttcc tgccaaaggc attccaattc tgtcaatgcc aagcaacaac atg tgg      2096
                                                         Met Trp
                                                          1 tgg ggg tcg ctg ctg ctg ctg ctg ctc gcg gcc gcg gtg gcg gcg         2144
Trp Gly Ser Leu Leu Leu Leu Leu Leu Ala Ala Ala Val Ala Ala
        5              10                 15 gct gct gag ccg gcg tcg acg ctc acg ggc ccg tca cgg ccg gtc acg    2192
Ala Ala Glu Pro Ala Ser Thr Leu Thr Gly Pro Ser Arg Pro Val Thr
 20              25                 30 gtg gcg ctg cgg gaa gac agg ggc cac gcg gtg gac ctg ccg gac acg    2240
Val Ala Leu Arg Glu Asp Arg Gly His Ala Val Asp Leu Pro Asp Thr
 35              40                 45              50 gac ccc cgg gtg cag cgc cgg gcc acg ggc tgg gct ccc gag cag atc    2288
Asp Pro Arg Val Gln Arg Arg Ala Thr Gly Trp Ala Pro Glu Gln Ile
             55                 60                 65 gcc gtc gcg ctc tcc gcc gct ccc acc tct gcc tgg gtc tcc tgg atc    2336
Ala Val Ala Leu Ser Ala Ala Pro Thr Ser Ala Trp Val Ser Trp Ile
         70                 75                 80 acc ggt agtaatctgc tcaccggact ctgattcctg ggttggatgg cattgactct      2392
Thr Gly tggttccgca ggg gaa ttc cag atg ggc ggc acc gtc aag ccg ctg gac      2441
            Glu Phe Gln Met Gly Gly Thr Val Lys Pro Leu Asp
                 85                 90                 95 ccc ggc acg gtc ggc agc gtc gtg cgc tac ggg ctc gcc gcc gat tct    2489
Pro Gly Thr Val Gly Ser Val Val Arg Tyr Gly Leu Ala Ala Asp Ser
         100                105                110 ttg gtt cgc cag gcc agc ggc gac gcg ctc gtg tac agc cag ctc tac    2537
Leu Val Arg Gln Ala Ser Gly Asp Ala Leu Val Tyr Ser Gln Leu Tyr
     115                120                125 ccc ttc gag ggt ctc cag aac tac acc tcc ggc atc atc cac cac gtc    2585
```

```
                Pro Phe Glu Gly Leu Gln Asn Tyr Thr Ser Gly Ile Ile His His Val
                130                 135                 140 cgc ctc caa ggt gaccgccgtc gttcgttgat ccctgttcc acaatcaatt                    2637
Arg Leu Gln Gly
145 ttttttttg catattttt gggagtgcaa tgaagtatct gcatgcaggg ctt gag                  2693
                                                      Leu Glu
                                                          150 cct gcg acg aag tac tac tac cag tgc ggc gac ccg gcc ctc ccg ggg               2741
Pro Ala Thr Lys Tyr Tyr Tyr Gln Cys Gly Asp Pro Ala Leu Pro Gly
                155                 160                 165 gcg atg agc gcc gtc cac gcg ttc cgg acg atg ccg gcg gtg ggg ccg               2789
Ala Met Ser Ala Val His Ala Phe Arg Thr Met Pro Ala Val Gly Pro
                170                 175                 180 cgg agc tac ccg ggg agg atc gcc gtg gtg gga gac ctc ggg ctc acg               2837
Arg Ser Tyr Pro Gly Arg Ile Ala Val Val Gly Asp Leu Gly Leu Thr
                185                 190                 195 tac aac acc acc tcc acc gtg gac cac atg gcg agc aac cgg ccg gac               2885
Tyr Asn Thr Thr Ser Thr Val Asp His Met Ala Ser Asn Arg Pro Asp
200                 205                 210 ctg gtc ctc ctc gtc ggc gac gtg tgc tac gcc aac atg tac ctc acc               2933
Leu Val Leu Leu Val Gly Asp Val Cys Tyr Ala Asn Met Tyr Leu Thr
215                 220                 225                 230 aac ggc acc gga gcg gac tgc tac tcg tgc gcg ttc ggc aag tcg acg               2981
Asn Gly Thr Gly Ala Asp Cys Tyr Ser Cys Ala Phe Gly Lys Ser Thr
                235                 240                 245 ccc atc cac gag acg tac cag ccg cgc tgg gac tac tgg gga agg tac               3029
Pro Ile His Glu Thr Tyr Gln Pro Arg Trp Asp Tyr Trp Gly Arg Tyr
                250                 255                 260 atg gag gcg gtg acg tcg ggg acg ccg atg atg gtg gtg gaa ggg aac               3077
Met Glu Ala Val Thr Ser Gly Thr Pro Met Met Val Val Glu Gly Asn
                265                 270                 275 cat gag ata gag gag cag atc ggg aac aag acg ttc gcg gcc tac cgc               3125
His Glu Ile Glu Glu Gln Ile Gly Asn Lys Thr Phe Ala Ala Tyr Arg
                280                 285                 290 tcc cgg ttc gcg ttc ccg tcg acg gag agc ggg tcc ttc tcc ccc ttc               3173
Ser Arg Phe Ala Phe Pro Ser Thr Glu Ser Gly Ser Phe Ser Pro Phe
295                 300                 305                 310 tac tac tcg ttc gac gcc ggc ggg atc cat ttc ctc atg ctc ggc gcc               3221
Tyr Tyr Ser Phe Asp Ala Gly Gly Ile His Phe Leu Met Leu Gly Ala
                315                 320                 325 tac gcc gac tac ggc agg tca ggg gag cag tac aga tgg ctg gag aag               3269
Tyr Ala Asp Tyr Gly Arg Ser Gly Glu Gln Tyr Arg Trp Leu Glu Lys
                330                 335                 340 gac ctg gcg aag gtg gac agg tcg gtg acg ccg tgg ctg gtc gcc ggc               3317
Asp Leu Ala Lys Val Asp Arg Ser Val Thr Pro Trp Leu Val Ala Gly
                345                 350                 355 tgg cac gcg cca tgg tac acc acc tac aag gct cac tac agg gag gtg               3365
Trp His Ala Pro Trp Tyr Thr Thr Tyr Lys Ala His Tyr Arg Glu Val
                360                 365                 370 gag tgc atg aga gtg gcc atg gag gag ctg ctc tac tcc cac ggc ctc               3413
Glu Cys Met Arg Val Ala Met Glu Glu Leu Leu Tyr Ser His Gly Leu
375                 380                 385                 390 gac atc gcc ttc acc ggc cat gta aca cct caa tca cac cct ctg act               3461
Asp Ile Ala Phe Thr Gly His Val Thr Pro Gln Ser His Pro Leu Thr
                395                 400                 405 gac acg gat cga cct acc tcc gtt ctc tgg aca ttg gca agc agc cga               3509
Asp Thr Asp Arg Pro Thr Ser Val Leu Trp Thr Leu Ala Ser Ser Arg
                410                 415                 420
```

```
gag tga tca ctc gct tgc tgt gtg atg cag gtg cac gcg tat gag cgc      3557
Glu     Ser Leu Ala Cys Cys Val Met Gln Val His Ala Tyr Glu Arg
            425                 430                 435 tcc aac cgg gtg ttc aac tac acg ctg gac ccg tgc ggc gcc gtg cac      3605
Ser Asn Arg Val Phe Asn Tyr Thr Leu Asp Pro Cys Gly Ala Val His
        440                 445                 450 atc tcg gtg ggc gac ggc ggg aac cgc gag aag atg gcc acc acc cac      3653
Ile Ser Val Gly Asp Gly Gly Asn Arg Glu Lys Met Ala Thr Thr His
    455                 460                 465 gcc gac gag ccg ggg cac tgc ccg gac ccg cgg ccc aag ccc aac gcc      3701
Ala Asp Glu Pro Gly His Cys Pro Asp Pro Arg Pro Lys Pro Asn Ala
470                 475                 480                 485 ttc atc ggc ggc ttc tgc gcc tcc aac ttc acg tcc ggc ccg gcc gcc      3749
Phe Ile Gly Gly Phe Cys Ala Ser Asn Phe Thr Ser Gly Pro Ala Ala
                490                 495                 500 ggc agg ttc tgc tgg gac cgg cag ccg gac tac agc gcc tac cgg gag      3797
Gly Arg Phe Cys Trp Asp Arg Gln Pro Asp Tyr Ser Ala Tyr Arg Glu
            505                 510                 515 agc agc ttc ggc cac ggc atc ctc gag gta cgtacgtacg aggaaaacaa        3847
Ser Ser Phe Gly His Gly Ile Leu Glu Val
        520                 525 gatcgaagag aattctgacc agctagatat atggttcgtt tgaccgatgt gagacgacgc    3907
aattggttca cgcaggtg aag aac gag acg cac gct ctg tgg aga tgg cac      3958
                    Lys Asn Glu Thr His Ala Leu Trp Arg Trp His
                                    530                 535 agg aac cag gac cac tac ggg agc gcc gga gat gag att tac att gtc      4006
Arg Asn Gln Asp His Tyr Gly Ser Ala Gly Asp Glu Ile Tyr Ile Val
    540                 545                 550 cgg gag ccg cac agg tgc ttg cac aag cac aac tcg agc agg ccg gca      4054
Arg Glu Pro His Arg Cys Leu His Lys His Asn Ser Ser Arg Pro Ala
555                 560                 565                 570 cac ggt cga tca aac acc aca cgg gaa tcg gga ggt taaccgttgt           4100
His Gly Arg Ser Asn Thr Thr Arg Glu Ser Gly Gly
                575                 580 accactggag tagatcgcgt ggtgtaatgg caactgtata gacggttcgc ccaagcgtgg    4160
aaataaaaag ttataccaac taaaacatgg attgggcagt gctaggcgct ggccggccgg    4220
ccggcccaaa tttccaacgg tcgtgctagc cgcccgacac cagtcgcact ggccgttgga    4280
tctagcaaaa aaaaaaaaaa accggttcgc gaagctcccc accccaccca caatctcgcg    4340
cagctaaccc cgttgccgcg ctcaccctcc acctgggcgg cgacaccctc cacctatgcc    4400
cgccggcgct cgtccttggt ttcgtgcgtt tctgctccgg tgctcccctc ctgggctgaa    4460
cgcgaggtgg aaaaacacat cgacggccag gatgaaccaa aaacggttaa taacgagggg    4520
cacgatcgtc tttgttgccc cgcgtatagc cgtcgaggag cccagggagg cccgtacgag    4580
cccggttaga tcgtatgccc ggccgtatac gtatttgtat atggcggcgt tcgtgcacg     4640 cgtggagccg cccgcgcgtg gggcagcacg tgtcacgggt agattccaaa atcgtcccat    4700
catataaatg tggacggcaa ccacctccgg ccgcatcgcc caccattccc cccgccgca     4760 tcgtctccct ctccccactc ccaattcccc actccgtttc ctctccaaca ttct          4814

<210> SEQ ID NO 46
<211> LENGTH: 25
<212> TYPE: DNA
<213> ORGANISM: Hordeum vulgare
<220> FEATURE:
<221> NAME/KEY: primer_bind
<222> LOCATION: (1)..(25)
<223> OTHER INFORMATION: HvPAPhy_a SDmut Fw primer for mutant enhancer
```

-continued

```
<400> SEQUENCE: 46
gtagaacacg agccatgcat gagac                                 25

<210> SEQ ID NO 47
<211> LENGTH: 25
<212> TYPE: DNA
<213> ORGANISM: Hordeum vulgare
<220> FEATURE:
<221> NAME/KEY: primer_bind
<222> LOCATION: (1)..(25)
<223> OTHER INFORMATION: HvPAPhy_a SDmut Rv primer for mutant enhancer

<400> SEQUENCE: 47
tggctcgtgt tctacaaaat gtagc                                 25

<210> SEQ ID NO 48
<211> LENGTH: 20
<212> TYPE: DNA
<213> ORGANISM: Hordeum vulgare
<220> FEATURE:
<221> NAME/KEY: primer_bind
<222> LOCATION: (1)..(20)
<223> OTHER INFORMATION: Cis to GUS Fw primer

<400> SEQUENCE: 48
tcgagtcgac gttccttgac                                       20

<210> SEQ ID NO 49
<211> LENGTH: 23
<212> TYPE: DNA
<213> ORGANISM: Hordeum vulgare
<220> FEATURE:
<221> NAME/KEY: primer_bind
<222> LOCATION: (1)..(23)
<223> OTHER INFORMATION: Cis to GUS Rv primer

<400> SEQUENCE: 49
gttgatgttg ttgcttggca ttg                                   23

<210> SEQ ID NO 50
<211> LENGTH: 36
<212> TYPE: DNA
<213> ORGANISM: Escherichia coli
<220> FEATURE:
<221> NAME/KEY: primer_bind
<222> LOCATION: (1)..(36)
<223> OTHER INFORMATION: GUS Fw m. overhang primer

<400> SEQUENCE: 50
agcaacaaca tcaacatgtt acgtcctgta gaaacc                     36

<210> SEQ ID NO 51
<211> LENGTH: 38
<212> TYPE: DNA
<213> ORGANISM: Escherichia coli
<220> FEATURE:
<221> NAME/KEY: primer_bind
<222> LOCATION: (1)..(38)
<223> OTHER INFORMATION: GUS Rv m. overhang primer

<400> SEQUENCE: 51
ggaacgtcga ctcgactatg accatgatta cgaattcc                   38

<210> SEQ ID NO 52
<211> LENGTH: 8132
<212> TYPE: DNA
```

```
<213> ORGANISM: Hordeum vulgare
<220> FEATURE:
<221> NAME/KEY: gene
<222> LOCATION: (1)..(8132)
<223> OTHER INFORMATION: pCLEAN-G185-wt-proGUS
<220> FEATURE:
<221> NAME/KEY: gene
<222> LOCATION: (1)..(2599)
<223> OTHER INFORMATION: Vector backbone, pCLEAN-G185
<220> FEATURE:
<221> NAME/KEY: promoter
<222> LOCATION: (2600)..(4799)
<223> OTHER INFORMATION: HvPAPhy_a promoter
<220> FEATURE:
<221> NAME/KEY: CDS
<222> LOCATION: (4800)..(6611)
<223> OTHER INFORMATION: UidA gene encoding GUS
<220> FEATURE:
<221> NAME/KEY: terminator
<222> LOCATION: (6612)..(6959)
<223> OTHER INFORMATION: NOS terminator
<220> FEATURE:
<221> NAME/KEY: gene
<222> LOCATION: (6960)..(8132)
<223> OTHER INFORMATION: Vector backbone, pCLEAN-G185

<400> SEQUENCE: 52
```

| | | | | | |
|---|---|---|---|---|---|
| catgtgagca | aaaggccagc | aaaaggccag | gaaccgtaaa | aaggccgcgt | tgctggcgtt    60 |
| tttccatagg | ctccgccccc | ctgacgagca | tcacaaaaat | cgacgctcaa | gtcagaggtg   120 |
| gcgaaacccg | acaggactat | aaagatacca | ggcgtttccc | cctggaagct | ccctcgtgcg   180 |
| ctctcctgtt | ccgaccctgc | cgcttaccgg | atacctgtcc | gcctttctcc | cttcgggaag   240 |
| cgtggcgctt | tctcatagct | cacgctgtag | gtatctcagt | tcggtgtagg | tcgttcgctc   300 |
| caagctgggc | tgtgtgcacg | aaccccccgt | tcagcccgac | cgctgcgcct | tatccggtaa   360 |
| ctatcgtctt | gagtccaacc | cggtaagaca | cgacttatcg | ccactggcag | cagccactgg   420 |
| taacaggatt | agcagagcga | ggtatgtagg | cggtgctaca | gagttcttga | agtggtggcc   480 |
| taactacggc | tacactagaa | gaacagtatt | tggtatctgc | gctctgctga | agccagttac   540 |
| cttcggaaga | agagttggta | gctcttgatc | cggcaaacaa | accaccgctg | gtagcggtgg   600 |
| tttttttgtt | tgcaagcagc | agattacgcg | cagaaaaaaa | ggatctcaag | aagatccttt   660 |
| gatcttttct | acggggtctg | acgctcagtg | gaacgaaaac | tcacgttaag | ggattttggt   720 |
| catgagatta | tcaaaaagga | tcttcaccta | gatcctttta | aattaaaaat | gaagttttaa   780 |
| atcaatctaa | agtatatatg | tgtaacattg | gtctagtgat | tagaaaaact | catcgagcat   840 |
| caaatgaaac | tgcaatttat | tcatatcagg | attatcaata | ccatattttt | gaaaaagccg   900 |
| tttctgtaat | gaaggagaaa | actcaccgag | gcagttccat | aggatggcaa | gatcctggta   960 |
| tcggtctgcg | attccgactc | gtccaacatc | aatacaacct | attaatttcc | cctcgtcaaa  1020 |
| aataaggtta | tcaagtgaga | aatcaccatg | agtgacgact | gaatccggtg | agaatggcaa  1080 |
| aagtttatgc | atttctttcc | agacttgttc | aacaggccag | ccattacgct | cgtcatcaaa  1140 |
| atcactcgca | tcaaccaaac | cgttattcat | tcgtgattgc | gcctgagcga | gacgaaatac  1200 |
| gcgatcgctg | ttaaaaggac | aattacaaac | aggaatcgaa | tgcaaccggc | gcaggaacac  1260 |
| tgccagcgca | tcaacaatat | tttcacctga | atcaggatat | tcttctaata | cctggaatgc  1320 |
| tgttttccct | gggatcgcag | tggtgagtaa | ccatgcatca | tcaggagtac | ggataaaatg  1380 |
| cttgatggtc | ggaagaggca | taaattccgt | cagccagttt | agtctgacca | tctcatctgt  1440 |
| aacaacattg | gcaacgctac | ctttgccatg | tttcagaaac | aactctggcg | catcgggctt  1500 |
| cccatacaat | cggtagattg | tcgcacctga | ttgcccgaca | ttatcgcgag | cccatttata  1560 |

```
cccatataaa tcagcatcca tgttggaatt taatcgcggc cttgagcaag acgtttcccg    1620
ttgaatatgg ctcataacac cccttgtatt actgtttatg taagcagaca gttttattgt    1680
tcatgatgat atattttat  cttgtgcaat gtaacatcag agattttgag acacaacgtg    1740
gctttgttga ataaatcgaa cttttgctga gttgaaggat cagatcacgc atcttcccga    1800
caacgcagac cgttccgtgg caaagcaaaa gttcaaaatc accaactggt ccacctacaa    1860
caaagctctc atcaaccgtg gctccctcac tttctggctg gatgatgggg cgattcaggc    1920
gatccccatc aacagcccg  ccgtcgagcg ggcttttta  tccccggaag cctgtggata    1980
gagggtagtt atccacgtga aaccgctaat gccccgcaaa gccttgattc acggggcttt    2040
ccggcccgct ccaaaaacta tccacgtgaa atcgctaatc agggtacgtg aaatcgctaa    2100
tcggagtacg tgaaatcgct aataaggtca cgtgaaatcg ctaatcaaaa aggcacgtga    2160
gaacgctaat agccctttca gatcaacagc ttgcaaacac ccctcgctcc ggcaagtagt    2220
tacagcaagt agtatgttca attagctttt caattatgaa tatatatatc aattattggt    2280
cgcccttggc ttgtggacaa tgcgctacgc gcaccggctc cgcccgtgga caaccgcaag    2340
cggttgccca ccgtcgagcg cctttgccca caacccggcg gccggccgca acagatcgtt    2400
ttataaattt tttttttga  aaaagaaaaa gcccgaaagg cggcaacctc tcgggcttct    2460
ggatttccga tccccggaat tagatccgtt taaactacgt aagatcttgg caggatatat    2520
tgtggtgtaa acgttcctgc ggcggtcgag atggatcttg gcaggatata ttgtggtgta    2580
aacgttcctg cggccgcatc ttgggcaaca tatcaggggc agcgccattg ccctgcgact    2640
gacggcggcg gtggaggagc ttggggcaga catgagctga aacgacgag  agagaggagt    2700 ggtggcgggc gagacagagg agcgacatga ttgaagaaga gcagcgggat tgaggattag    2760
ggattcctgc gattttacac ttgacctctc cataaaagat tggcctaatc gaagctgaga    2820
acgtggaggt caacaagtgg tcaaacgagc ctgtacgcac cgcatacgag caacagtgat    2880
cggattttca cgtcacatcg tatatagtga tcgtaaaagc catattctaa agttggatga    2940
ccgtattgtg cttccatgtc aactgcaagg accgtgagtg tatttatctc taaaatataa    3000
atcaaatata atggtgggct tcttcagacc tcattcagct caaaatccgc ccatgaagcc    3060
aatttgaatg ctctaacttt tgcgaagctg gaatctattg tatccaagac tagtgttttc    3120
aaagatagtc ttttcggaat ttcaaaatca ctatgtgtgt tcgtcgtatg aacaactctc    3180
gactagagag tattcttaat aatgcgataa gagtataaca taacaatttt tttgaatgta    3240
ggtttagttg gtctccatgg agcgagacct agtcctattt ggggaggcct ctcgtagttt    3300
ggatggacat agttctgtcg gttcaggttg taatgcaact cctcgcactt gactctaaaa    3360
tgacttaggc tattgaaagg cccaaaaaca atagtattct tcccttgagt tcattcaagt    3420
gagagtatat gtccatgggg ctaagagaag gggtcccttg acaaatgatc aaggttgcgc    3480
aaggtgatga taggtatatt ggtaaatctg tatccacgag ttcatgaagt attcaaaggt    3540
gggggtctat agtccatggt acatcaatca tttccaccca tgtatgaatg ggcctttggc    3600
tagttgggct catttagatt tgggctcagt tacttcttgc cttaaatatt gactttgaca    3660
tttcattttg gtttcccttt ttatttgttg accatgataa tttgcttggc cttttattta    3720 atttttatg  gttttgatta ttttttaaac acaatacaga cgaaaacatt catgtacaca    3780
cacatgcatt catcttttatg aacatacaca tccacatcat gtccctatca tcttgaaatt    3840
tatgaagtca tagtagacac ctagtcgtcg agggggaattc tcctcggatt gaatgtgtat    3900
```

-continued

```
cgtcgaaaat tgtgaaataa atgtgagcgc caggacttga atcttgatgg actaggataa    3960
cacagtttct ctaaccatcc aaccgtatgt tggttcgcga tagtttggat tgcttaccac    4020
atgtgtcatg tggttgctag gacttccatt aatctggccg aaccttgtta attgagttgg    4080
atatttcttg accattttag acctattaa gagcatcttc aacaacagtg taaaaaatcc     4140
gcgcccaata aatttttagc gcgccactgt agcacttta aagcgcgggg acggaagcat     4200
cttcaataga cacgcgctaa tgcggcgccc aatccacccc ggtccagcga cccacccaca    4260
acagctcaga gtttgctgcg cgcgcaagcc ggcacaccaa atatgctgtc cgcgatagcg    4320
tttttaagcg cgtgcccaaa atttttagt gcgagcacag ttttgcagcg tctgttggag     4380
ctgttcggcg ccaaaaaacg aatctttaa cgcgcggtgt agttttgagg cgtctgttgg     4440
agatggtcta accggcttga accgtgttga aaaaaaaacc cggcttgaat ttttgttgac    4500
gagccatagt tgcatattac gtacgttact tgctctttaa tttcaagcta cattttgtag    4560
aacatgagcc atgcatgaga cgtaggcgtc caaactttgg ctagcgcagc tgcatgcacg    4620
tccacaaggc accaaaggcg caggcggcaa ctttgctcgt ttattttctt gcgggtccaa    4680
gatgagttcc agaccatgga cgaattccac ttcgggctcc caatctcctc tgccggattc    4740
ctataagttt cctgccaaga agcatcccaa tcccctcaat gccaagcaac aacatcaac    4799
```

| atg tta cgt cct gta gaa acc cca acc cgt gaa atc aaa aaa ctc gac | 4847 |
|---|---|
| Met Leu Arg Pro Val Glu Thr Pro Thr Arg Glu Ile Lys Lys Leu Asp | |
| 1                5                  10                 15        | |

| ggc ctg tgg gca ttc agt ctg gat cgc gaa aac tgt gga att gat cag | 4895 |
|---|---|
| Gly Leu Trp Ala Phe Ser Leu Asp Arg Glu Asn Cys Gly Ile Asp Gln | |
|          20                 25                 30               | |

| cgt tgg tgg gaa agc gcg tta caa gaa agc cgg gca att gct gtg cca | 4943 |
|---|---|
| Arg Trp Trp Glu Ser Ala Leu Gln Glu Ser Arg Ala Ile Ala Val Pro | |
|      35                 40                 45                   | |

| ggc agt ttt aac gat cag ttc gcc gat gca gat att cgt aat tat gcg | 4991 |
|---|---|
| Gly Ser Phe Asn Asp Gln Phe Ala Asp Ala Asp Ile Arg Asn Tyr Ala | |
|  50                 55                 60                       | |

| ggc aac gtc tgg tat cag cgc gaa gtc ttt ata ccg aaa ggt tgg gca | 5039 |
|---|---|
| Gly Asn Val Trp Tyr Gln Arg Glu Val Phe Ile Pro Lys Gly Trp Ala | |
| 65                 70                 75                 80     | |

| ggc cag cgt atc gtg ctg cgt ttc gat gcg gtc act cat tac ggc aaa | 5087 |
|---|---|
| Gly Gln Arg Ile Val Leu Arg Phe Asp Ala Val Thr His Tyr Gly Lys | |
|              85                 90                 95           | |

| gtg tgg gtc aat aat cag gaa gtg atg gag cat cag ggc ggc tat acg | 5135 |
|---|---|
| Val Trp Val Asn Asn Gln Glu Val Met Glu His Gln Gly Gly Tyr Thr | |
|              100                105                110          | |

| cca ttt gaa gcc gat gtc acg ccg tat gtt att gcc ggg aaa agt gta | 5183 |
|---|---|
| Pro Phe Glu Ala Asp Val Thr Pro Tyr Val Ile Ala Gly Lys Ser Val | |
|          115                120                125              | |

| cgt atc acc gtt tgt gtg aac aac gaa ctg aac tgg cag act atc ccg | 5231 |
|---|---|
| Arg Ile Thr Val Cys Val Asn Asn Glu Leu Asn Trp Gln Thr Ile Pro | |
|      130                135                140                  | |

| ccg gga atg gtg att acc gac gaa aac ggc aag aaa aag cag tct tac | 5279 |
|---|---|
| Pro Gly Met Val Ile Thr Asp Glu Asn Gly Lys Lys Lys Gln Ser Tyr | |
| 145                150                155                160   | |

| ttc cat gat ttc ttt aac tat gcc gga atc cat cgc agc gta atg ctc | 5327 |
|---|---|
| Phe His Asp Phe Phe Asn Tyr Ala Gly Ile His Arg Ser Val Met Leu | |
|              165                170                175          | |

| tac acc acg ccg aac acc tgg gtg gac gat atc acc gtg gtg acg cat | 5375 |
|---|---|
| Tyr Thr Thr Pro Asn Thr Trp Val Asp Asp Ile Thr Val Val Thr His | |
|          180                185                190              | |

| gtc gcg caa gac tgt aac cac gcg tct gtt gac tgg cag gtg gtg gcc | 5423 |
|---|---|

```
Val Ala Gln Asp Cys Asn His Ala Ser Val Asp Trp Gln Val Val Ala
        195                 200                 205 aat ggt gat gtc agc gtt gaa ctg cgt gat gcg gat caa cag gtg gtt    5471
Asn Gly Asp Val Ser Val Glu Leu Arg Asp Ala Asp Gln Gln Val Val
210                 215                 220 gca act gga caa ggc act agc ggg act ttg caa gtg gtg aat ccg cac    5519
Ala Thr Gly Gln Gly Thr Ser Gly Thr Leu Gln Val Val Asn Pro His
225                 230                 235                 240 ctc tgg caa ccg ggt gaa ggt tat ctc tat gaa ctg tgc gtc aca gcc    5567
Leu Trp Gln Pro Gly Glu Gly Tyr Leu Tyr Glu Leu Cys Val Thr Ala
                245                 250                 255 aaa agc cag aca gag tgt gat atc tac ccg ctt cgc gtc ggc atc cgg    5615
Lys Ser Gln Thr Glu Cys Asp Ile Tyr Pro Leu Arg Val Gly Ile Arg
            260                 265                 270 tca gtg gca gtg aag ggc gaa cag ttc ctg att aac cac aaa ccg ttc    5663
Ser Val Ala Val Lys Gly Glu Gln Phe Leu Ile Asn His Lys Pro Phe
        275                 280                 285 tac ttt act ggc ttt ggt cgt cat gaa gat gcg gac ttg cgt ggc aaa    5711
Tyr Phe Thr Gly Phe Gly Arg His Glu Asp Ala Asp Leu Arg Gly Lys
    290                 295                 300 gga ttc gat aac gtg ctg atg gtg cac gac cac gca tta atg gac tgg    5759
Gly Phe Asp Asn Val Leu Met Val His Asp His Ala Leu Met Asp Trp
305                 310                 315                 320 att ggg gcc aac tcc tac cgt acc tcg cat tac cct tac gct gaa gag    5807
Ile Gly Ala Asn Ser Tyr Arg Thr Ser His Tyr Pro Tyr Ala Glu Glu
                325                 330                 335 atg ctc gac tgg gca gat gaa cat ggc atc gtg gtg att gat gaa act    5855
Met Leu Asp Trp Ala Asp Glu His Gly Ile Val Val Ile Asp Glu Thr
            340                 345                 350 gct gct gtc ggc ttt aac ctc tct tta ggc att ggt ttc gaa gcg ggc    5903
Ala Ala Val Gly Phe Asn Leu Ser Leu Gly Ile Gly Phe Glu Ala Gly
        355                 360                 365 aac aag ccg aaa gaa ctg tac agc gaa gag gca gtc aac ggg gaa act    5951
Asn Lys Pro Lys Glu Leu Tyr Ser Glu Glu Ala Val Asn Gly Glu Thr
    370                 375                 380 cag caa gcg cac tta cag gcg att aaa gag ctg ata gcg cgt gac aaa    5999
Gln Gln Ala His Leu Gln Ala Ile Lys Glu Leu Ile Ala Arg Asp Lys
385                 390                 395                 400 aac cac cca agc gtg gtg atg tgg agt att gcc aac gaa ccg gat acc    6047
Asn His Pro Ser Val Val Met Trp Ser Ile Ala Asn Glu Pro Asp Thr
                405                 410                 415 cgt ccg caa ggt gca cgg gaa tat ttc gcg cca ctg gcg gaa gca acg    6095
Arg Pro Gln Gly Ala Arg Glu Tyr Phe Ala Pro Leu Ala Glu Ala Thr
            420                 425                 430 cgt aaa ctc gac ccg acg cgt ccg atc acc tgc gtc aat gta atg ttc    6143
Arg Lys Leu Asp Pro Thr Arg Pro Ile Thr Cys Val Asn Val Met Phe
        435                 440                 445 tgc gac gct cac acc gat acc atc agc gat ctc ttt gat gtg ctg tgc    6191
Cys Asp Ala His Thr Asp Thr Ile Ser Asp Leu Phe Asp Val Leu Cys
    450                 455                 460 ctg aac cgt tat tac gga tgg tat gtc caa agc ggc gat ttg gaa acg    6239
Leu Asn Arg Tyr Tyr Gly Trp Tyr Val Gln Ser Gly Asp Leu Glu Thr
465                 470                 475                 480 gca gag aag gta ctg gaa aaa gaa ctt ctg gcc tgg cag gag aaa ctg    6287
Ala Glu Lys Val Leu Glu Lys Glu Leu Leu Ala Trp Gln Glu Lys Leu
                485                 490                 495 cat cag ccg att atc atc acc gaa tac ggc gtg gat acg tta gcc ggg    6335
His Gln Pro Ile Ile Ile Thr Glu Tyr Gly Val Asp Thr Leu Ala Gly
            500                 505                 510
```

| | | | | | | | | | | | | | | | |
|---|---|---|---|---|---|---|---|---|---|---|---|---|---|---|---|
|ctg|cac|tca|atg|tac|acc|gac|atg|tgg|agt|gaa|gag|tat|cag|tgt|gca|
|Leu|His|Ser|Met|Tyr|Thr|Asp|Met|Trp|Ser|Glu|Glu|Tyr|Gln|Cys|Ala|
| |515| | | | |520| | | | |525| | | | |

6383

| | | | | | | | | | | | | | | | |
|---|---|---|---|---|---|---|---|---|---|---|---|---|---|---|---|
|tgg|ctg|gat|atg|tat|cac|cgc|gtc|ttt|gat|cgc|gtc|agc|gcc|gtc|gtc|
|Trp|Leu|Asp|Met|Tyr|His|Arg|Val|Phe|Asp|Arg|Val|Ser|Ala|Val|Val|
|530| | | | |535| | | | |540| | | | | |

6431

| | | | | | | | | | | | | | | | |
|---|---|---|---|---|---|---|---|---|---|---|---|---|---|---|---|
|ggt|gaa|cag|gta|tgg|aat|ttc|gcc|gat|ttt|gcg|acc|tcg|caa|ggc|ata|
|Gly|Glu|Gln|Val|Trp|Asn|Phe|Ala|Asp|Phe|Ala|Thr|Ser|Gln|Gly|Ile|
|545| | | | |550| | | | |555| | | | |560|

6479

| | | | | | | | | | | | | | | | |
|---|---|---|---|---|---|---|---|---|---|---|---|---|---|---|---|
|ttg|cgc|gtt|ggc|ggt|aac|aag|aaa|ggg|atc|ttc|act|cgc|gac|cgc|aaa|
|Leu|Arg|Val|Gly|Gly|Asn|Lys|Lys|Gly|Ile|Phe|Thr|Arg|Asp|Arg|Lys|
| | | | |565| | | | |570| | | | |575| |

6527

| | | | | | | | | | | | | | | | |
|---|---|---|---|---|---|---|---|---|---|---|---|---|---|---|---|
|ccg|aag|tcg|gcg|gct|ttt|ctg|ctg|caa|aaa|cgc|tgg|act|ggc|atg|aac|
|Pro|Lys|Ser|Ala|Ala|Phe|Leu|Leu|Gln|Lys|Arg|Trp|Thr|Gly|Met|Asn|
| | | |580| | | | |585| | | | |590| | |

6575

| | | | | | | | | | |
|---|---|---|---|---|---|---|---|---|---|
|ttc|ggt|gaa|aaa|ccg|cag|cag|gga|ggc|aaa|caa|tga|atcaacaact|
|Phe|Gly|Glu|Lys|Pro|Gln|Gln|Gly|Gly|Lys|Gln| | |
| |595| | | | |600| | | | | | |

6621 ctcctggcgc accatcgtcg gctacagcct cgggaattgc taccgagctc gaatttcccc 6681 gatcgttcaa acatttggca ataaagtttc ttaagattga atcctgttgc cggtcttgcg 6741 atgattatca tataatttct gttgaattac gttaagcatg taataattaa catgtaatgc 6801 atgacgttat ttatgagatg ggtttttatg attagagtcc cgcaattata catttaatac 6861 gcgatagaaa acaaaatata gcgcgcaaac taggataaat tatcgcgcgc ggtgtcatct 6921 atgttactag atcgggaatt cgtaatcatg gtcatagtcg agtcgacgtt ccttgacagg 6981 atatattggc gggtaaacta agtcgctgta tgtgtttgtt tgagatcctc tagggcatgc 7041 aggctcgcgg cggacgcacg acgccggggc gagaccatag gcgatctcct aaatcaatag 7101 tagctgtaac ctcgaagcgt ttcacttgta acaacgattg agaattttg tcataaaatt 7161 gaaatacttg gttcgcattt ttgtcatccg cggtcagccg caattctgac gaactgccca 7221 tttagctgga gatgattgta catccttcac gtgaaaattt ctcaagcgct gtgaacaagg 7281 gttcagattt tagattgaaa ggtgagccgt tgaaacacgt tcttcttgtc gatgacgacg 7341 tcgctatgcg gcatcttatt attgaatacc ttacgatcca cgccttcaaa gtgaccgcgg 7401 tagccgacag cacccagttc acaagagtac tctcttccgc gacggtcgat gtcgtggttg 7461 ttgatctaaa tttaggtcgt gaagatgggc tcgagatcgt tcgtaatctg gcggcaaagt 7521 ctgatattcc aatcataatt atcagtggcg accgccttga ggagacggat aaagttgttg 7581 cactcgagct aggagcaagt gattttatcg ctaagccgtt cagtatcaga gagttttctag 7641 cacgcattcg ggttgccttg cgcgtgcgcc ccaacgttgt ccgctccaaa gaccgacggt 7701 cttttttgttt tactgactgg acacttaatc tcaggcaacg tcgcttgatg tccgaagctg 7761 gcggtgaggt gaaacttacg gcaggtgagt tcaatcttct cctcgcgttt ttagagaaac 7821 cccgcgacgt tctatcgcgc gagcaacttc tcattgccag tcgagtacgc gacgaggagg 7881 tttatgacag gagtatagat gttctcattt tgaggctgcg ccgcaaactt gaggcggatc 7941 cgtcaagccc tcaactgata aaaacagcaa gaggtgccgg ttatttcttt gacgcggacg 8001 tgcaggtttc gcacgggggg acgatggcag cctgagccaa ttgcatttgc ctcttaatta 8061 tctggctcaa agggtgactg aggagtaagc gatgtgccca tcacactgcg catgcaagct 8121 gatctggatc t 8132

<210> SEQ ID NO 53
<211> LENGTH: 603

```
<212> TYPE: PRT
<213> ORGANISM: Hordeum vulgare

<400> SEQUENCE: 53

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
    370                 375                 380

Gln Gln Ala His Leu Gln Ala Ile Lys Glu Leu Ile Ala Arg Asp Lys
385                 390                 395                 400
```

-continued

```
Asn His Pro Ser Val Val Met Trp Ser Ile Ala Asn Glu Pro Asp Thr
            405                 410                 415

Arg Pro Gln Gly Ala Arg Glu Tyr Phe Ala Pro Leu Ala Glu Ala Thr
        420                 425                 430

Arg Lys Leu Asp Pro Thr Arg Pro Ile Thr Cys Val Asn Val Met Phe
            435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
    530                 535                 540

Gly Glu Gln Val Trp Asn Phe Ala Asp Phe Ala Thr Ser Gln Gly Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln
        595                 600

<210> SEQ ID NO 54
<211> LENGTH: 8132
<212> TYPE: DNA
<213> ORGANISM: Hordeum vulgare
<220> FEATURE:
<221> NAME/KEY: gene
<222> LOCATION: (1)..(8132)
<223> OTHER INFORMATION: pCLEAN-G185-HP-proGUS
<220> FEATURE:
<221> NAME/KEY: gene
<222> LOCATION: (1)..(2599)
<223> OTHER INFORMATION: Vector backbone, pCLEAN-G185
<220> FEATURE:
<221> NAME/KEY: promoter
<222> LOCATION: (2600)..(4799)
<223> OTHER INFORMATION: HighPhy HvPAPhy_a promoter
<220> FEATURE:
<221> NAME/KEY: mutation
<222> LOCATION: (4565)..(4565)
<223> OTHER INFORMATION: HighPhy enhancer mutation
<220> FEATURE:
<221> NAME/KEY: CDS
<222> LOCATION: (4800)..(6611)
<223> OTHER INFORMATION: UidA gene (encoding GUS)
<220> FEATURE:
<221> NAME/KEY: terminator
<222> LOCATION: (6612)..(6959)
<223> OTHER INFORMATION: NOS terminator
<220> FEATURE:
<221> NAME/KEY: gene
<222> LOCATION: (6960)..(8132)
<223> OTHER INFORMATION: Vector backbone, pCLEAN-G185

<400> SEQUENCE: 54
catgtgagca aaaggccagc aaaaggccag gaaccgtaaa aaggccgcgt tgctggcgtt       60
tttccatagg ctccgccccc ctgacgagca tcacaaaaat cgacgctcaa gtcagaggtg     120
```

```
gcgaaacccg acaggactat aaagatacca ggcgtttccc cctggaagct ccctcgtgcg    180
ctctcctgtt ccgaccctgc cgcttaccgg atacctgtcc gcctttctcc cttcgggaag    240
cgtggcgctt tctcatagct cacgctgtag gtatctcagt tcggtgtagg tcgttcgctc    300
caagctgggc tgtgtgcacg aacccccgt tcagcccgac cgctgcgcct tatccggtaa     360
ctatcgtctt gagtccaacc cggtaagaca cgacttatcg ccactggcag cagccactgg    420
taacaggatt agcagagcga ggtatgtagg cggtgctaca gagttcttga agtggtggcc    480
taactacggc tacactagaa gaacagtatt tggtatctgc gctctgctga agccagttac    540
cttcggaaga gagttggta gctcttgatc cggcaaacaa accaccgctg gtagcggtgg    600
tttttttgtt tgcaagcagc agattacgcg cagaaaaaaa ggatctcaag aagatccttt    660
gatcttttct acggggtctg acgctcagtg gaacgaaaac tcacgttaag ggattttggt    720
catgagatta tcaaaaagga tcttcaccta gatccttta aattaaaaat gaagttttaa     780
atcaatctaa agtatatatg tgtaacattg gtctagtgat tagaaaaact catcgagcat    840
caaatgaaac tgcaatttat tcatatcagg attatcaata ccatattttt gaaaaagccg    900
tttctgtaat gaaggagaaa actcaccgag gcagttccat aggatggcaa gatcctggta    960
tcggtctgcg attccgactc gtccaacatc aatacaacct attaatttcc cctcgtcaaa    1020
aataaggtta tcaagtgaga atcaccatg agtgacgact gaatccggtg agaatggcaa    1080
aagtttatgc atttctttcc agacttgttc aacaggccag ccattacgct cgtcatcaaa    1140
atcactcgca tcaaccaaac cgttattcat tcgtgattgc gcctgagcga gacgaaatac    1200
gcgatcgctg ttaaaaggac aattacaaac aggaatcgaa tgcaaccggc gcaggaacac    1260
tgccagcgca tcaacaatat tttcacctga atcaggatat tcttctaata cctggaatgc    1320
tgttttccct gggatcgcag tggtgagtaa ccatgcatca tcaggagtac ggataaaatg    1380
cttgatggtc ggaagaggca taaattccgt cagccagttt agtctgacca tctcatctgt    1440
aacaacattg gcaacgctac ctttgccatg tttcagaaac aactctggcg catcgggctt    1500
cccatacaat cggtagattg tcgcacctga ttgcccgaca ttatcgcgag cccatttata    1560
cccatataaa tcagcatcca tgttggaatt taatcgcggc cttgagcaag acgtttcccg    1620
ttgaatatgg ctcataacac cccttgtatt actgtttatg taagcagaca gttttattgt    1680
tcatgatgat atatttttat cttgtgcaat gtaacatcag agattttgag acacaacgtg    1740
gctttgttga ataaatcgaa cttttgctga gttgaaggat cagatcacgc atcttcccga    1800
caacgcagac cgttccgtgg caaagcaaaa gttcaaaatc accaactggt ccacctacaa    1860
caaagctctc atcaaccgtg gctccctcac tttctggctg gatgatgggg cgattcaggc    1920
gatccccatc aacagcccg ccgtcgagcg ggcttttta tccccggaag cctgtggata     1980
gagggtagtt atccacgtga aaccgctaat gccccgcaaa gccttgattc acgggctttt    2040
ccggcccgct ccaaaaacta tccacgtgaa atcgctaatc agggtacgtg aaatcgctaa    2100
tcggagtacg tgaaatcgct aataaggtca cgtgaaatcg ctaatcaaaa aggcacgtga    2160
gaacgctaat agcccttca gatcaacagc ttgcaaacac ccctcgctcc ggcaagtagt    2220
tacagcaagt agtatgttca attagctttt caattatgaa tatatatatc aattattggt    2280
cgcccttggc ttgtggacaa tgcgctacgc gcaccggctc cgcccgtgga caaccgcaag    2340
cggttgccca ccgtcgagcg cctttgccca caacccggcg gccggccgca acagatcgtt    2400
ttataaattt ttttttttga aaagaaaaa gcccgaaagg cggcaacctc tcgggcttct    2460
```

| | |
|---|---|
| ggatttccga tcccccggaat tagatccgtt taaactacgt aagatcttgg caggatatat | 2520 |
| tgtggtgtaa acgttcctgc ggcggtcgag atggatcttg gcaggatata ttgtggtgta | 2580 |
| aacgttcctg cggccgcatc ttgggcaaca tatcaggggc agcgccattg ccctgcgact | 2640 |
| gacggcggcg gtggaggagc ttggggcaga catgagctga gaacgacgag agagaggagt | 2700 |
| ggtggcgggc gagacagagg agcgacatga ttgaagaaga gcagcgggat tgaggattag | 2760 |
| ggattcctgc gattttacac ttgacctctc cataaaagat tggcctaatc gaagctgaga | 2820 |
| acgtggaggt caacaagtgg tcaaacgagc ctgtacgcac cgcatacgag caacagtgat | 2880 |
| cggattttca cgtcacatcg tatatagtga tcgtaaaagc catattctaa agttggatga | 2940 |
| ccgtattgtg cttccatgtc aactgcaagg accgtgagtg tatttatctc taaaatataa | 3000 |
| atcaaatata atggtgggct tcttcagacc tcattcagct caaaatccgc ccatgaagcc | 3060 |
| aatttgaatg ctctaacttt tgcgaagctg gaatctattg tatccaagac tagtgttttc | 3120 |
| aaagatagtc ttttcggaat ttcaaaatca ctatgtgtgt tcgtcgtatg aacaactctc | 3180 |
| gactagagag tattcttaat aatgcgataa gagtataaca taacaatttt tttgaatgta | 3240 |
| ggtttagttg gtctccatgg agcgagacct agtcctattt ggggaggcct ctcgtagttt | 3300 |
| ggatggacat agttctgtcg gttcaggttg taatgcaact cctcgcactt gactctaaaa | 3360 |
| tgacttaggc tattgaaagg cccaaaaaca atagtattct tcccttgagt tcattcaagt | 3420 |
| gagagtatat gtccatgggg ctaagagaag gggtcccttg acaaatgatc aaggttgcgc | 3480 |
| aaggtgatga taggtatatt ggtaaatctg tatccacgag ttcatgaagt attcaaaggt | 3540 |
| gggggtctat agtccatggt acatcaatca tttccaccca tgtatgaatg ggcctttggc | 3600 |
| tagttgggct catttagatt tgggctcagt tacttcttgc cttaaatatt gactttgaca | 3660 |
| tttcattttg gtttcccttt ttatttgttg accatgataa tttgcttggc cttttattta | 3720 |
| atttttatg gttttgatta ttttttaaac acaatacaga cgaaaacatt catgtacaca | 3780 |
| cacatgcatt catctttatg aacatacaca tccacatcat gtccctatca tcttgaaatt | 3840 |
| tatgaagtca tagtagacac ctagtcgtcg aggggaattc tcctcggatt gaatgtgtat | 3900 |
| cgtcgaaaat tgtgaaataa atgtgagcgc caggacttga atcttgatgg actaggataa | 3960 |
| cacagtttct ctaaccatcc aaccgtatgt tggttcgcga tagtttggat tgcttaccac | 4020 |
| atgtgtcatg tggttgctag gacttccatt aatctggccg aaccttgtta attgagttgg | 4080 |
| atatttcttg accattttag accttattaa gagcatcttc aacaacagtg taaaaaatcc | 4140 |
| gcgcccaata aattttttagc gcgccactgt agcacttttta aagcgcgggg acggaagcat | 4200 |
| cttcaataga cacgcgctaa tgcggcgccc aatccacccc ggtccagcga cccacccaca | 4260 |
| acagctcaga gtttgctgcg cgcgcaagcc ggcacaccaa atatgctgtc cgcgatagcg | 4320 |
| ttttaagcg cgtgcccaaa atttttttagt gcgagcacag ttttgcagcg tctgttggag | 4380 |
| ctgttcggcg ccaaaaaacg aatcttttaa cgcgcggtgt agtttgaggg cgtctgttgg | 4440 |
| agatggtcta accggcttga accgtgttga aaaaaaaacc cggcttgaat ttttgttgac | 4500 |
| gagccatagt tgcatattac gtacgttact tgctctttaa tttcaagcta cattttgtag | 4560 |
| aacacgagcc atgcatgaga cgtaggcgtc caaactttgg ctagcgcagc tgcatgcacg | 4620 |
| tccacaaggc accaaaggcg caggcggcaa ctttgctcgt ttattttctt gcgggtccaa | 4680 |
| gatgagttcc agaccatgga cgaattccac ttcgggctcc caatctcctc tgccggattc | 4740 |
| ctataagttt cctgccaaga agcatcccaa tcccctcaat gccaagcaac aacatcaac | 4799 |
| atg tta cgt cct gta gaa acc cca acc cgt gaa atc aaa aaa ctc gac | 4847 |

```
Met Leu Arg Pro Val Glu Thr Pro Thr Arg Glu Ile Lys Lys Leu Asp
1               5                   10                  15 ggc ctg tgg gca ttc agt ctg gat cgc gaa aac tgt gga att gat cag        4895
Gly Leu Trp Ala Phe Ser Leu Asp Arg Glu Asn Cys Gly Ile Asp Gln
            20                  25                  30 cgt tgg tgg gaa agc gcg tta caa gaa agc cgg gca att gct gtg cca        4943
Arg Trp Trp Glu Ser Ala Leu Gln Glu Ser Arg Ala Ile Ala Val Pro
                35                  40                  45 ggc agt ttt aac gat cag ttc gcc gat gca gat att cgt aat tat gcg        4991
Gly Ser Phe Asn Asp Gln Phe Ala Asp Ala Asp Ile Arg Asn Tyr Ala
        50                  55                  60 ggc aac gtc tgg tat cag cgc gaa gtc ttt ata ccg aaa ggt tgg gca        5039
Gly Asn Val Trp Tyr Gln Arg Glu Val Phe Ile Pro Lys Gly Trp Ala
65                  70                  75                  80 ggc cag cgt atc gtg ctg cgt ttc gat gcg gtc act cat tac ggc aaa        5087
Gly Gln Arg Ile Val Leu Arg Phe Asp Ala Val Thr His Tyr Gly Lys
                85                  90                  95 gtg tgg gtc aat aat cag gaa gtg atg gag cat cag ggc ggc tat acg        5135
Val Trp Val Asn Asn Gln Glu Val Met Glu His Gln Gly Gly Tyr Thr
            100                 105                 110 cca ttt gaa gcc gat gtc acg ccg tat gtt att gcc ggg aaa agt gta        5183
Pro Phe Glu Ala Asp Val Thr Pro Tyr Val Ile Ala Gly Lys Ser Val
        115                 120                 125 cgt atc acc gtt tgt gtg aac aac gaa ctg aac tgg cag act atc ccg        5231
Arg Ile Thr Val Cys Val Asn Asn Glu Leu Asn Trp Gln Thr Ile Pro
130                 135                 140 ccg gga atg gtg att acc gac gaa aac ggc aag aaa aag cag tct tac        5279
Pro Gly Met Val Ile Thr Asp Glu Asn Gly Lys Lys Lys Gln Ser Tyr
145                 150                 155                 160 ttc cat gat ttc ttt aac tat gcc gga atc cat cgc agc gta atg ctc        5327
Phe His Asp Phe Phe Asn Tyr Ala Gly Ile His Arg Ser Val Met Leu
                165                 170                 175 tac acc acg ccg aac acc tgg gtg gac gat atc acc gtg gtg acg cat        5375
Tyr Thr Thr Pro Asn Thr Trp Val Asp Asp Ile Thr Val Val Thr His
            180                 185                 190 gtc gcg caa gac tgt aac cac gcg tct gtt gac tgg cag gtg gtg gcc        5423
Val Ala Gln Asp Cys Asn His Ala Ser Val Asp Trp Gln Val Val Ala
        195                 200                 205 aat ggt gat gtc agc gtt gaa ctg cgt gat gcg gat caa cag gtg gtt        5471
Asn Gly Asp Val Ser Val Glu Leu Arg Asp Ala Asp Gln Gln Val Val
210                 215                 220 gca act gga caa ggc act agc ggg act ttg caa gtg gtg aat ccg cac        5519
Ala Thr Gly Gln Gly Thr Ser Gly Thr Leu Gln Val Val Asn Pro His
225                 230                 235                 240 ctc tgg caa ccg ggt gaa ggt tat ctc tat gaa ctg tgc gtc aca gcc        5567
Leu Trp Gln Pro Gly Glu Gly Tyr Leu Tyr Glu Leu Cys Val Thr Ala
                245                 250                 255 aaa agc cag aca gag tgt gat atc tac ccg ctt cgc gtc ggc atc cgg        5615
Lys Ser Gln Thr Glu Cys Asp Ile Tyr Pro Leu Arg Val Gly Ile Arg
            260                 265                 270 tca gtg gca gtg aag ggc gaa cag ttc ctg att aac cac aaa ccg ttc        5663
Ser Val Ala Val Lys Gly Glu Gln Phe Leu Ile Asn His Lys Pro Phe
        275                 280                 285 tac ttt act ggc ttt ggt cgt cat gaa gat gcg gac ttg cgt ggc aaa        5711
Tyr Phe Thr Gly Phe Gly Arg His Glu Asp Ala Asp Leu Arg Gly Lys
290                 295                 300 gga ttc gat aac gtg ctg atg gtg cac gac cac gca tta atg gac tgg        5759
Gly Phe Asp Asn Val Leu Met Val His Asp His Ala Leu Met Asp Trp
305                 310                 315                 320
```

```
att ggg gcc aac tcc tac cgt acc tcg cat tac cct tac gct gaa gag      5807
Ile Gly Ala Asn Ser Tyr Arg Thr Ser His Tyr Pro Tyr Ala Glu Glu
                325                 330                 335 atg ctc gac tgg gca gat gaa cat ggc atc gtg gtg att gat gaa act      5855
Met Leu Asp Trp Ala Asp Glu His Gly Ile Val Val Ile Asp Glu Thr
            340                 345                 350 gct gct gtc ggc ttt aac ctc tct tta ggc att ggt ttc gaa gcg ggc      5903
Ala Ala Val Gly Phe Asn Leu Ser Leu Gly Ile Gly Phe Glu Ala Gly
                355                 360                 365 aac aag ccg aaa gaa ctg tac agc gaa gag gca gtc aac ggg gaa act      5951
Asn Lys Pro Lys Glu Leu Tyr Ser Glu Glu Ala Val Asn Gly Glu Thr
        370                 375                 380 cag caa gcg cac tta cag gcg att aaa gag ctg ata gcg cgt gac aaa      5999
Gln Gln Ala His Leu Gln Ala Ile Lys Glu Leu Ile Ala Arg Asp Lys
385                 390                 395                 400 aac cac cca agc gtg gtg atg tgg agt att gcc aac gaa ccg gat acc      6047
Asn His Pro Ser Val Val Met Trp Ser Ile Ala Asn Glu Pro Asp Thr
                405                 410                 415 cgt ccg caa ggt gca cgg gaa tat ttc gcg cca ctg gcg gaa gca acg      6095
Arg Pro Gln Gly Ala Arg Glu Tyr Phe Ala Pro Leu Ala Glu Ala Thr
            420                 425                 430 cgt aaa ctc gac ccg acg cgt ccg atc acc tgc gtc aat gta atg ttc      6143
Arg Lys Leu Asp Pro Thr Arg Pro Ile Thr Cys Val Asn Val Met Phe
                435                 440                 445 tgc gac gct cac acc gat acc atc agc gat ctc ttt gat gtg ctg tgc      6191
Cys Asp Ala His Thr Asp Thr Ile Ser Asp Leu Phe Asp Val Leu Cys
        450                 455                 460 ctg aac cgt tat tac gga tgg tat gtc caa agc ggc gat ttg gaa acg      6239
Leu Asn Arg Tyr Tyr Gly Trp Tyr Val Gln Ser Gly Asp Leu Glu Thr
465                 470                 475                 480 gca gag aag gta ctg gaa aaa gaa ctt ctg gcc tgg cag gag aaa ctg      6287
Ala Glu Lys Val Leu Glu Lys Glu Leu Leu Ala Trp Gln Glu Lys Leu
                485                 490                 495 cat cag ccg att atc atc acc gaa tac ggc gtg gat acg tta gcc ggg      6335
His Gln Pro Ile Ile Ile Thr Glu Tyr Gly Val Asp Thr Leu Ala Gly
            500                 505                 510 ctg cac tca atg tac acc gac atg tgg agt gaa gag tat cag tgt gca      6383
Leu His Ser Met Tyr Thr Asp Met Trp Ser Glu Glu Tyr Gln Cys Ala
                515                 520                 525 tgg ctg gat atg tat cac cgc gtc ttt gat cgc gtc agc gcc gtc gtc      6431
Trp Leu Asp Met Tyr His Arg Val Phe Asp Arg Val Ser Ala Val Val
        530                 535                 540 ggt gaa cag gta tgg aat ttc gcc gat ttt gcg acc tcg caa ggc ata      6479
Gly Glu Gln Val Trp Asn Phe Ala Asp Phe Ala Thr Ser Gln Gly Ile
545                 550                 555                 560 ttg cgt gtt ggc ggt aac aag aaa ggg atc ttc act cgc gac cgc aaa      6527
Leu Arg Val Gly Gly Asn Lys Lys Gly Ile Phe Thr Arg Asp Arg Lys
                565                 570                 575 ccg aag tcg gcg gct ttt ctg ctg caa aaa cgc tgg act ggc atg aac      6575
Pro Lys Ser Ala Ala Phe Leu Leu Gln Lys Arg Trp Thr Gly Met Asn
            580                 585                 590 ttc ggt gaa aaa ccg cag cag gga ggc aaa caa tga atcaacaact           6621
Phe Gly Glu Lys Pro Gln Gln Gly Gly Lys Gln
                595                 600 ctcctggcgc accatcgtcg gctacagcct cgggaattgc taccgagctc gaatttcccc    6681
gatcgttcaa acatttggca ataaagtttt ttaagattga atcctgttgc cggtcttgcg    6741
atgattatca tataatttct gttgaattac gttaagcatg taataattaa catgtaatgc    6801
atgacgttat ttatgagatg ggtttttatg attagagtcc cgcaattata catttaatac    6861
```

-continued

```
gcgatagaaa acaaaatata gcgcgcaaac taggataaat tatcgcgcgc ggtgtcatct   6921
atgttactag atcgggaatt cgtaatcatg gtcatagtcg agtcgacgtt ccttgacagg   6981
atatattggc gggtaaacta agtcgctgta tgtgtttgtt tgagatcctc tagggcatgc   7041
aggctcgcgg cggacgcacg acgccggggc gagaccatag gcgatctcct aaatcaatag   7101
tagctgtaac ctcgaagcgt ttcacttgta acaacgattg agaattttg tcataaaatt    7161 gaaatacttg gttcgcattt ttgtcatccg cggtcagccg caattctgac gaactgccca   7221
tttagctgga gatgattgta catccttcac gtgaaaattt ctcaagcgct gtgaacaagg   7281
gttcagattt tagattgaaa ggtgagccgt tgaaacacgt tcttcttgtc gatgacgacg   7341
tcgctatgcg gcatcttatt attgaatacc ttacgatcca cgccttcaaa gtgaccgcgg   7401
tagccgacag cacccagttc acaagagtac tctcttccgc gacggtcgat gtcgtggttg   7461
ttgatctaaa tttaggtcgt gaagatgggc tcgagatcgt tcgtaatctg gcggcaaagt   7521
ctgatattcc aatcataatt atcagtggcg accgccttga ggagacggat aaagttgttg   7581
cactcgagct aggagcaagt gattttatcg ctaagccgtt cagtatcaga gagtttctag   7641
cacgcattcg ggttgccttg cgcgtgcgcc ccaacgttgt ccgctccaaa gaccgacggt   7701 cttttgttt tactgactgg acacttaatc tcaggcaacg tcgcttgatg tccgaagctg     7761
gcggtgaggt gaaacttacg gcaggtgagt tcaatcttct cctcgcgttt ttagagaaac   7821
cccgcgacgt tctatcgcgc gagcaacttc tcattgccag tcgagtacgc gacgaggagg   7881
tttatgacag gagtatagat gttctcattt tgaggctgcg ccgcaaactt gaggcggatc   7941
cgtcaagccc tcaactgata aaaacagcaa gaggtgccgg ttatttcttt gacgcggacg   8001
tgcaggtttc gcacgggggg acgatggcag cctgagccaa ttgcatttgc ctcttaatta   8061
tctggctcaa agggtgactg aggagtaagc gatgtgccca tcacactgcg catgcaagct   8121
gatctggatc t                                                         8132
```

<210> SEQ ID NO 55
<211> LENGTH: 603
<212> TYPE: PRT
<213> ORGANISM: Hordeum vulgare

<400> SEQUENCE: 55

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

-continued

```
Pro Gly Met Val Ile Thr Asp Glu Asn Gly Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Thr His
            180                 185                 190

Val Ala Gln Asp Cys Asn His Ala Ser Val Asp Trp Gln Val Val Ala
            195                 200                 205

Asn Gly Asp Val Ser Val Glu Leu Arg Asp Ala Asp Gln Gln Val Val
        210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Ile Asp Glu Thr
            340                 345                 350

Ala Ala Val Gly Phe Asn Leu Ser Leu Gly Ile Gly Phe Glu Ala Gly
            355                 360                 365

Asn Lys Pro Lys Glu Leu Tyr Ser Glu Glu Ala Val Asn Gly Glu Thr
        370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
        450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
        530                 535                 540

Gly Glu Gln Val Trp Asn Phe Ala Asp Phe Ala Thr Ser Gln Gly Ile
545                 550                 555                 560
```

-continued

```
Leu Arg Val Gly Gly Asn Lys Lys Gly Ile Phe Thr Arg Asp Arg Lys
            565                 570                 575

Pro Lys Ser Ala Ala Phe Leu Leu Gln Lys Arg Trp Thr Gly Met Asn
        580                 585                 590

Phe Gly Glu Lys Pro Gln Gln Gly Gly Lys Gln
    595                 600
```

```
<210> SEQ ID NO 56
<211> LENGTH: 39
<212> TYPE: DNA
<213> ORGANISM: Hordeum vulgare
<220> FEATURE:
<221> NAME/KEY: primer_bind
<222> LOCATION: (1)..(39)
<223> OTHER INFORMATION: Kill triad Fw primer to randomise
      mutant enhancer

<400> SEQUENCE: 56
gcatacgaag catagtacga cgtaggcgtc caaactttg                         39

<210> SEQ ID NO 57
<211> LENGTH: 48
<212> TYPE: DNA
<213> ORGANISM: Hordeum vulgare
<220> FEATURE:
<221> NAME/KEY: primer_bind
<222> LOCATION: (1)..(48)
<223> OTHER INFORMATION: Kill triad Rv primer to randomise
      mutant enhancer

<400> SEQUENCE: 57
tcgtactatg cttcgtatgc ctacaaaatg tagcttgaaa ttaaagag               48

<210> SEQ ID NO 58
<211> LENGTH: 8132
<212> TYPE: DNA
<213> ORGANISM: Hordeum vulgare
<220> FEATURE:
<221> NAME/KEY: gene
<222> LOCATION: (1)..(8132)
<223> OTHER INFORMATION: pCLEAN-G185-KOtriad-ProGUS
<220> FEATURE:
<221> NAME/KEY: gene
<222> LOCATION: (1)..(2599)
<223> OTHER INFORMATION: Vector backbone, pCLEAN-G185
<220> FEATURE:
<221> NAME/KEY: promoter
<222> LOCATION: (2600)..(4799)
<223> OTHER INFORMATION: KOtriad HvPAPhy_a promoter
<220> FEATURE:
<221> NAME/KEY: enhancer
<222> LOCATION: (4561)..(4580)
<223> OTHER INFORMATION: Randomized sequence replacing the enhancer
      triad (GCN4, skn1, RY-element)
<220> FEATURE:
<221> NAME/KEY: CDS
<222> LOCATION: (4800)..(6611)
<223> OTHER INFORMATION: UidA gene (encoding GUS)
<220> FEATURE:
<221> NAME/KEY: terminator
<222> LOCATION: (6612)..(6959)
<223> OTHER INFORMATION: NOS terminator
<220> FEATURE:
<221> NAME/KEY: gene
<222> LOCATION: (6960)..(8132)
<223> OTHER INFORMATION: Vector backbone, pCLEAN-G185

<400> SEQUENCE: 58
catgtgagca aaaggccagc aaaaggccag gaaccgtaaa aaggccgcgt tgctggcgtt    60
tttccatagg ctccgccccc ctgacgagca tcacaaaaat cgacgctcaa gtcagaggtg   120
```

```
gcgaaacccg acaggactat aaagatacca ggcgtttccc cctggaagct ccctcgtgcg    180
ctctcctgtt ccgaccctgc cgcttaccgg atacctgtcc gcctttctcc cttcgggaag    240
cgtggcgctt tctcatagct cacgctgtag gtatctcagt tcggtgtagg tcgttcgctc    300
caagctgggc tgtgtgcacg aacccccgt tcagcccgac cgctgcgcct tatccggtaa     360
ctatcgtctt gagtccaacc cggtaagaca cgacttatcg ccactggcag cagccactgg    420
taacaggatt agcagagcga ggtatgtagg cggtgctaca gagttcttga agtggtggcc    480
taactacggc tacactagaa gaacagtatt tggtatctgc gctctgctga agccagttac    540
cttcggaaga gagttggta gctcttgatc cggcaaacaa accaccgctg gtagcggtgg     600 ttttttgtt tgcaagcagc agattacgcg cagaaaaaaa ggatctcaag aagatccttt     660
gatcttttct acggggtctg acgctcagtg gaacgaaaac tcacgttaag ggattttggt    720
catgagatta tcaaaaagga tcttcaccta gatccttta aattaaaaat gaagttttaa     780
atcaatctaa agtatatatg tgtaacattg gtctagtgat tagaaaaact catcgagcat    840
caaatgaaac tgcaatttat tcatatcagg attatcaata ccatattttt gaaaaagccg    900
tttctgtaat gaaggagaaa actcaccgag gcagttccat aggatggcaa gatcctggta    960
tcggtctgcg attccgactc gtccaacatc aatacaacct attaatttcc cctcgtcaaa   1020
aataaggtta tcaagtgaga atcaccatg agtgacgact gaatccggtg agaatggcaa    1080
aagtttatgc atttctttcc agacttgttc aacaggccag ccattacgct cgtcatcaaa   1140
atcactcgca tcaaccaaac cgttattcat tcgtgattgc gcctgagcga gacgaaatac   1200
gcgatcgctg ttaaaaggac aattacaaac aggaatcgaa tgcaaccggc gcaggaacac   1260
tgccagcgca tcaacaatat tttcacctga atcaggatat tcttctaata cctggaatgc   1320
tgttttccct gggatcgcag tggtgagtaa ccatgcatca tcaggagtac ggataaaatg   1380
cttgatggtc ggaagaggca taaattccgt cagccagttt agtctgacca tctcatctgt   1440
aacaacattg gcaacgctac ctttgccatg tttcagaaac aactctggcg catcgggctt   1500
cccatacaat cggtagattg tcgcacctga ttgcccgaca ttatcgcgag cccatttata   1560
cccatataaa tcagcatcca tgttggaatt taatcgcggc cttgagcaag acgtttcccg   1620
ttgaatatgg ctcataacac cccttgtatt actgtttatg taagcagaca gttttattgt   1680
tcatgatgat atatttttat cttgtgcaat gtaaatcag agattttgag acacaacgtg    1740
gctttgttga ataaatcgaa cttttgctga gttgaaggat cagatcacgc atcttcccga   1800
caacgcagac cgttccgtgg caaagcaaaa gttcaaaatc accaactggt ccacctacaa   1860
caaagctctc atcaaccgtg gctccctcac tttctggctg gatgatgggg cgattcaggc   1920
gatccccatc aacagcccg ccgtcgagcg ggcttttta tccccggaag cctgtggata    1980
gagggtagtt atccacgtga aaccgctaat gccccgcaaa gccttgattc acggggcttt   2040
ccggcccgct ccaaaaacta tccacgtgaa atcgctaatc agggtacgtg aaatcgctaa   2100
tcggagtacg tgaaatcgct aataaggtca cgtgaaatcg ctaatcaaaa aggcacgtga   2160
gaacgctaat agccctttca gatcaacagc ttgcaaacac ccctcgctcc ggcaagtagt   2220
tacagcaagt agtatgttca attagctttt caattatgaa tatatatatc aattattggt   2280
cgcccttggc ttgtggacaa tgcgctacgc gcaccggctc cgcccgtgga caaccgcaag   2340
cggttgccca ccgtcgagcg cctttgccca caacccggcg gccggccgca acagatcgtt   2400
ttataaattt ttttttttga aaagaaaaa gcccgaaagg cggcaacctc tcgggcttct   2460
```

-continued

```
ggatttccga tccccggaat tagatccgtt taaactacgt aagatcttgg caggatatat      2520
tgtggtgtaa acgttcctgc ggcggtcgag atggatcttg gcaggatata ttgtggtgta      2580
aacgttcctg cggccgcatc ttgggcaaca tatcaggggc agcgccattg ccctgcgact      2640
gacggcggcg gtggaggagc ttggggcaga catgagctga gaacgacgag agagaggagt      2700
ggtggcgggc gagacagagg agcgacatga ttgaagaaga gcagcgggat tgaggattag      2760
ggattcctgc gattttacac ttgacctctc cataaaagat tggcctaatc gaagctgaga      2820
acgtggaggt caacaagtgg tcaaacgagc ctgtacgcac cgcatacgag caacagtgat      2880
cggattttca cgtcacatcg tatatagtga tcgtaaaagc catattctaa agttggatga      2940
ccgtattgtg cttccatgtc aactgcaagg accgtgagtg tatttatctc taaaatataa      3000
atcaaatata atggtgggct tcttcagacc tcattcagct caaaatccgc ccatgaagcc      3060
aatttgaatg ctctaacttt tgcgaagctg gaatctattg tatccaagac tagtgttttc      3120
aaagatagtc ttttcggaat ttcaaaatca ctatgtgtgt tcgtcgtatg aacaactctc      3180
gactagagag tattcttaat aatgcgataa gagtataaca taacaatttt tttgaatgta      3240
ggtttagttg gtctccatgg agcgagacct agtcctattt ggggaggcct ctcgtagttt      3300
ggatggacat agttctgtcg gttcaggttg taatgcaact cctcgcactt gactctaaaa      3360
tgacttaggc tattgaaagg cccaaaaaca atagtattct tcccttgagt tcattcaagt      3420
gagagtatat gtccatgggg ctaagagaag gggtcccttg acaaatgatc aaggttgcgc      3480
aaggtgatga taggtatatt ggtaaatctg tatccacgag ttcatgaagt attcaaaggt      3540
gggggtctat agtccatggt acatcaatca tttccaccca tgtatgaatg ggcctttggc      3600
tagttgggct catttagatt tgggctcagt tacttcttgc cttaaatatt gactttgaca      3660
tttcattttg gtttcccttt ttatttgttg accatgataa tttgcttggc cttttattta      3720
atttttatg gttttgatta ttttttaaac acaatacaga cgaaaacatt catgtacaca      3780
cacatgcatt catctttatg aacatacaca tccacatcat gtccctatca tcttgaaatt      3840
tatgaagtca tagtagacac ctagtcgtcg aggggaattc tcctcggatt gaatgtgtat      3900
cgtcgaaaat tgtgaaataa atgtgagcgc caggacttga atcttgatgg actaggataa      3960
cacagtttct ctaaccatcc aaccgtatgt tggttcgcga tagtttggat tgcttaccac      4020
atgtgtcatg tggttgctag gacttccatt aatctggccg aaccttgtta attgagttgg      4080
atatttcttg accattttag accttattaa gagcatcttc aacaacagtg taaaaaatcc      4140
gcgcccaata aattttttagc gcgccactgt agcacttttta aagcgcgggg acggaagcat      4200
cttcaataga cacgcgctaa tgcggcgccc aatccacccc ggtccagcga cccacccaca      4260
acagctcaga gtttgctgcg cgcgcaagcc ggcacaccaa atatgctgtc cgcgatagcg      4320
ttttttaagcg cgtgcccaaa attttttagt gcgagcacag ttttgcagcg tctgttggag      4380
ctgttcggcg ccaaaaaacg aatcttttaa cgcgcggtgt agtttgagg cgtctgttgg       4440
agatggtcta accggcttga accgtgttga aaaaaaaacc cggcttgaat ttttgttgac      4500
gagccatagt tgcatattac gtacgttact tgctctttaa tttcaagcta cattttgtag      4560
gcatacgaag catagtacga cgtaggcgtc caaactttgg ctagcgcagc tgcatgcacg      4620
tccacaaggc accaaaggcg caggcggcaa ctttgctcgt ttattttctt gcgggtccaa      4680
gatgagttcc agaccatgga cgaattccac ttcgggctcc caatctcctc tgccggattc      4740
ctataagttt cctgccaaga agcatcccaa tcccctcaat gccaagcaac aacatcaac       4799
atg tta cgt cct gta gaa acc cca acc cgt gaa atc aaa aaa ctc gac       4847
```

```
Met Leu Arg Pro Val Glu Thr Pro Thr Arg Glu Ile Lys Lys Leu Asp
1               5                   10                  15 ggc ctg tgg gca ttc agt ctg gat cgc gaa aac tgt gga att gat cag       4895
Gly Leu Trp Ala Phe Ser Leu Asp Arg Glu Asn Cys Gly Ile Asp Gln
            20                  25                  30 cgt tgg tgg gaa agc gcg tta caa gaa agc cgg gca att gct gtg cca       4943
Arg Trp Trp Glu Ser Ala Leu Gln Glu Ser Arg Ala Ile Ala Val Pro
        35                  40                  45 ggc agt ttt aac gat cag ttc gcc gat gca gat att cgt aat tat gcg       4991
Gly Ser Phe Asn Asp Gln Phe Ala Asp Ala Asp Ile Arg Asn Tyr Ala
    50                  55                  60 ggc aac gtc tgg tat cag cgc gaa gtc ttt ata ccg aaa ggt tgg gca       5039
Gly Asn Val Trp Tyr Gln Arg Glu Val Phe Ile Pro Lys Gly Trp Ala
65                  70                  75                  80 ggc cag cgt atc gtg ctg cgt ttc gat gcg gtc act cat tac ggc aaa       5087
Gly Gln Arg Ile Val Leu Arg Phe Asp Ala Val Thr His Tyr Gly Lys
                85                  90                  95 gtg tgg gtc aat aat cag gaa gtg atg gag cat cag ggc ggc tat acg       5135
Val Trp Val Asn Asn Gln Glu Val Met Glu His Gln Gly Gly Tyr Thr
            100                 105                 110 cca ttt gaa gcc gat gtc acg ccg tat gtt att gcc ggg aaa agt gta       5183
Pro Phe Glu Ala Asp Val Thr Pro Tyr Val Ile Ala Gly Lys Ser Val
        115                 120                 125 cgt atc acc gtt tgt gtg aac aac gaa ctg aac tgg cag act atc ccg       5231
Arg Ile Thr Val Cys Val Asn Asn Glu Leu Asn Trp Gln Thr Ile Pro
130                 135                 140 ccg gga atg gtg att acc gac gaa aac ggc aag aaa aag cag tct tac       5279
Pro Gly Met Val Ile Thr Asp Glu Asn Gly Lys Lys Lys Gln Ser Tyr
145                 150                 155                 160 ttc cat gat ttc ttt aac tat gcc gga atc cat cgc agc gta atg ctc       5327
Phe His Asp Phe Phe Asn Tyr Ala Gly Ile His Arg Ser Val Met Leu
                165                 170                 175 tac acc acg ccg aac acc tgg gtg gac gat atc acc gtg gtg acg cat       5375
Tyr Thr Thr Pro Asn Thr Trp Val Asp Asp Ile Thr Val Val Thr His
            180                 185                 190 gtc gcg caa gac tgt aac cac gcg tct gtt gac tgg cag gtg gtg gcc       5423
Val Ala Gln Asp Cys Asn His Ala Ser Val Asp Trp Gln Val Val Ala
        195                 200                 205 aat ggt gat gtc agc gtt gaa ctg cgt gat gcg gat caa cag gtg gtt       5471
Asn Gly Asp Val Ser Val Glu Leu Arg Asp Ala Asp Gln Gln Val Val
210                 215                 220 gca act gga caa ggc act agc ggg act ttg caa gtg gtg aat ccg cac       5519
Ala Thr Gly Gln Gly Thr Ser Gly Thr Leu Gln Val Val Asn Pro His
225                 230                 235                 240 ctc tgg caa ccg ggt gaa ggt tat ctc tat gaa ctg tgc gtc aca gcc       5567
Leu Trp Gln Pro Gly Glu Gly Tyr Leu Tyr Glu Leu Cys Val Thr Ala
                245                 250                 255 aaa agc cag aca gag tgt gat atc tac ccg ctt cgc gtc ggc atc cgg       5615
Lys Ser Gln Thr Glu Cys Asp Ile Tyr Pro Leu Arg Val Gly Ile Arg
            260                 265                 270 tca gtg gca gtg aag ggc gaa cag ttc ctg att aac cac aaa ccg ttc       5663
Ser Val Ala Val Lys Gly Glu Gln Phe Leu Ile Asn His Lys Pro Phe
        275                 280                 285 tac ttt act ggc ttt ggt cgt cat gaa gat gcg gac ttg cgt ggc aaa       5711
Tyr Phe Thr Gly Phe Gly Arg His Glu Asp Ala Asp Leu Arg Gly Lys
        290                 295                 300 gga ttc gat aac gtg ctg atg gtg cac gac cac gca tta atg gac tgg       5759
Gly Phe Asp Asn Val Leu Met Val His Asp His Ala Leu Met Asp Trp
305                 310                 315                 320
```

```
att ggg gcc aac tcc tac cgt acc tcg cat tac cct tac gct gaa gag    5807
Ile Gly Ala Asn Ser Tyr Arg Thr Ser His Tyr Pro Tyr Ala Glu Glu
                325                 330                 335 atg ctc gac tgg gca gat gaa cat ggc atc gtg gtg att gat gaa act    5855
Met Leu Asp Trp Ala Asp Glu His Gly Ile Val Val Ile Asp Glu Thr
            340                 345                 350 gct gct gtc ggc ttt aac ctc tct tta ggc att ggt ttc gaa gcg ggc    5903
Ala Ala Val Gly Phe Asn Leu Ser Leu Gly Ile Gly Phe Glu Ala Gly
                355                 360                 365 aac aag ccg aaa gaa ctg tac agc gaa gag gca gtc aac ggg gaa act    5951
Asn Lys Pro Lys Glu Leu Tyr Ser Glu Glu Ala Val Asn Gly Glu Thr
        370                 375                 380 cag caa gcg cac tta cag gcg att aaa gag ctg ata gcg cgt gac aaa    5999
Gln Gln Ala His Leu Gln Ala Ile Lys Glu Leu Ile Ala Arg Asp Lys
385                 390                 395                 400 aac cac cca agc gtg gtg atg tgg agt att gcc aac gaa ccg gat acc    6047
Asn His Pro Ser Val Val Met Trp Ser Ile Ala Asn Glu Pro Asp Thr
                405                 410                 415 cgt ccg caa ggt gca cgg gaa tat ttc gcg cca ctg gcg gaa gca acg    6095
Arg Pro Gln Gly Ala Arg Glu Tyr Phe Ala Pro Leu Ala Glu Ala Thr
                420                 425                 430 cgt aaa ctc gac ccg acg cgt ccg atc acc tgc gtc aat gta atg ttc    6143
Arg Lys Leu Asp Pro Thr Arg Pro Ile Thr Cys Val Asn Val Met Phe
            435                 440                 445 tgc gac gct cac acc gat acc atc agc gat ctc ttt gat gtg ctg tgc    6191
Cys Asp Ala His Thr Asp Thr Ile Ser Asp Leu Phe Asp Val Leu Cys
        450                 455                 460 ctg aac cgt tat tac gga tgg tat gtc caa agc ggc gat ttg gaa acg    6239
Leu Asn Arg Tyr Tyr Gly Trp Tyr Val Gln Ser Gly Asp Leu Glu Thr
465                 470                 475                 480 gca gag aag gta ctg gaa aaa gaa ctt ctg gcc tgg cag gag aaa ctg    6287
Ala Glu Lys Val Leu Glu Lys Glu Leu Leu Ala Trp Gln Glu Lys Leu
                485                 490                 495 cat cag ccg att atc atc acc gaa tac ggc gtg gat acg tta gcc ggg    6335
His Gln Pro Ile Ile Ile Thr Glu Tyr Gly Val Asp Thr Leu Ala Gly
                500                 505                 510 ctg cac tca atg tac acc gac atg tgg agt gaa gag tat cag tgt gca    6383
Leu His Ser Met Tyr Thr Asp Met Trp Ser Glu Glu Tyr Gln Cys Ala
            515                 520                 525 tgg ctg gat atg tat cac cgc gtc ttt gat cgc gtc agc gcc gtc gtc    6431
Trp Leu Asp Met Tyr His Arg Val Phe Asp Arg Val Ser Ala Val Val
        530                 535                 540 ggt gaa cag gta tgg aat ttc gcc gat ttt gcg acc tcg caa ggc ata    6479
Gly Glu Gln Val Trp Asn Phe Ala Asp Phe Ala Thr Ser Gln Gly Ile
545                 550                 555                 560 ttg cgc gtt ggc ggt aac aag aaa ggg atc ttc act cgc gac cgc aaa    6527
Leu Arg Val Gly Gly Asn Lys Lys Gly Ile Phe Thr Arg Asp Arg Lys
                565                 570                 575 ccg aag tcg gcg gct ttt ctg ctg caa aaa cgc tgg act ggc atg aac    6575
Pro Lys Ser Ala Ala Phe Leu Leu Gln Lys Arg Trp Thr Gly Met Asn
                580                 585                 590 ttc ggt gaa aaa ccg cag cag gga ggc aaa caa tga atcaacaact         6621
Phe Gly Glu Lys Pro Gln Gln Gly Gly Lys Gln
        595                 600 ctcctggcgc accatcgtcg gctacagcct cgggaattgc taccgagctc gaatttcccc  6681
gatcgttcaa acatttggca ataaagtttc ttaagattga atcctgttgc cggtcttgcg  6741
atgattatca tataatttct gttgaattac gttaagcatg taataattaa catgtaatgc  6801
atgacgttat ttatgagatg ggtttttatg attagagtcc cgcaattata catttaatac  6861
```

-continued

```
gcgatagaaa acaaaatata gcgcgcaaac taggataaat tatcgcgcgc ggtgtcatct   6921
atgttactag atcgggaatt cgtaatcatg gtcatagtcg agtcgacgtt ccttgacagg   6981
atatattggc gggtaaacta agtcgctgta tgtgtttgtt tgagatcctc tagggcatgc   7041
aggctcgcgg cggacgcacg acgccggggc gagaccatag gcgatctcct aaatcaatag   7101
tagctgtaac ctcgaagcgt ttcacttgta acaacgattg agaattttg tcataaaatt    7161
gaaatacttg gttcgcattt ttgtcatccg cggtcagccg caattctgac gaactgccca   7221
tttagctgga gatgattgta catccttcac gtgaaatt ctcaagcgct gtgaacaagg     7281
gttcagattt tagattgaaa ggtgagccgt tgaaacacgt tcttcttgtc gatgacgacg   7341
tcgctatgcg gcatcttatt attgaatacc ttacgatcca cgccttcaaa gtgaccgcgg   7401
tagccgacag cacccagttc acaagagtac tctcttccgc gacggtcgat gtcgtggttg   7461
ttgatctaaa tttaggtcgt gaagatgggc tcgagatcgt tcgtaatctg gcggcaaagt   7521
ctgatattcc aatcataatt atcagtggcg accgccttga ggagacggat aaagttgttg   7581
cactcgagct aggagcaagt gattttatcg ctaagccgtt cagtatcaga gagtttctag   7641
cacgcattcg ggttgccttg cgcgtgcgcc ccaacgttgt ccgctccaaa gaccgacggt   7701
cttttgttt tactgactgg acacttaatc tcaggcaacg tcgcttgatg tccgaagctg    7761
gcggtgaggt gaaacttacg gcaggtgagt tcaatcttct cctcgcgttt ttagagaaac   7821
cccgcgacgt tctatcgcgc gagcaacttc tcattgccag tcgagtacgc gacgaggagg   7881
tttatgacag gagtatagat gttctcattt tgaggctgcg ccgcaaactt gaggcggatc   7941
cgtcaagccc tcaactgata aaaacagcaa gaggtgccgg ttatttcttt gacgcggacg   8001
tgcaggtttc gcacgggggg acgatggcag cctgagccaa ttgcatttgc ctcttaatta   8061
tctggctcaa agggtgactg aggagtaagc gatgtgccca tcacactgcg catgcaagct   8121
gatctggatc t                                                        8132
```

```
<210> SEQ ID NO 59
<211> LENGTH: 603
<212> TYPE: PRT
<213> ORGANISM: Hordeum vulgare

<400> SEQUENCE: 59

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140
```

```
Pro Gly Met Val Ile Thr Asp Glu Asn Gly Lys Lys Gln Ser Tyr
145                 150                 155                 160

Phe His Asp Phe Phe Asn Tyr Ala Gly Ile His Arg Ser Val Met Leu
            165                 170                 175

Tyr Thr Thr Pro Asn Thr Trp Val Asp Asp Ile Thr Val Thr His
        180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
        210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
                260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
        290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
            355                 360                 365

Asn Lys Pro Lys Glu Leu Tyr Ser Glu Glu Ala Val Asn Gly Glu Thr
        370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
            435                 440                 445

Cys Asp Ala His Thr Asp Thr Ile Ser Asp Leu Phe Asp Val Leu Cys
        450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
            485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
        530                 535                 540

Gly Glu Gln Val Trp Asn Phe Ala Asp Phe Ala Thr Ser Gln Gly Ile
545                 550                 555                 560
```

```
Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln
        595                 600

<210> SEQ ID NO 60
<211> LENGTH: 20
<212> TYPE: DNA
<213> ORGANISM: Triticum aestivum
<220> FEATURE:
<221> NAME/KEY: primer_bind
<222> LOCATION: (1)..(20)
<223> OTHER INFORMATION: TaPAPhy_a1 gene forward primer

<400> SEQUENCE: 60
gagattccga gaccaacgaa                                              20

<210> SEQ ID NO 61
<211> LENGTH: 20
<212> TYPE: DNA
<213> ORGANISM: Triticum aestivum
<220> FEATURE:
<221> NAME/KEY: primer_bind
<222> LOCATION: (1)..(20)
<223> OTHER INFORMATION: TaPAPhy_a1 gene reverse primer

<400> SEQUENCE: 61
tttgcctcca ctctgcctac                                              20

<210> SEQ ID NO 62
<211> LENGTH: 16
<212> TYPE: DNA
<213> ORGANISM: Triticum aestivum

<400> SEQUENCE: 62
acavgagtca tgcatg                                                  16

<210> SEQ ID NO 63
<211> LENGTH: 20
<212> TYPE: DNA
<213> ORGANISM: Triticum aestivum

<400> SEQUENCE: 63
aacacgagtc atgcatggga                                              20

<210> SEQ ID NO 64
<211> LENGTH: 16
<212> TYPE: DNA
<213> ORGANISM: Triticum aestivum

<400> SEQUENCE: 64
cgagtcatgc atggga                                                  16

<210> SEQ ID NO 65
<211> LENGTH: 13
<212> TYPE: DNA
<213> ORGANISM: Triticum sp.

<400> SEQUENCE: 65
tgagtcatgc atg                                                     13

<210> SEQ ID NO 66
```

```
<211> LENGTH: 13
<212> TYPE: DNA
<213> ORGANISM: Triticum sp.

<400> SEQUENCE: 66
cgagtcatgc atg                                                          13
```

HIGH EXPRESSION CEREAL PHYTASE GENE

CROSS-REFERENCE TO RELATED APPLICATIONS

This is a U.S. national stage entry of International Patent Application No. PCT/EP2012/057515, filed on Apr. 25, 2012, which claims priority to European Patent Application No. 11163875.5, filed on Apr. 27, 2011, and U.S. Patent Application No. 61/479,689, filed on Apr. 27, 2011, the contents of all of which are fully incorporated herein by reference.

SEQUENCE LISTING

The instant application contains a Sequence Listing which has been submitted in ASCII format via EFS-Web and is hereby incorporated by reference in its entirety. Said ASCII copy, created on Mar. 26, 2014, is named P1275US01-030547-9022-US00SEQ-LIST-03-26-14.txt, and is 194,104 bytes in size.

TECHNICAL FIELD OF THE INVENTION

The present invention relates to mutant cereal plants and mature grain thereof, characterised by an enhancer polynucleotide capable of directed enhanced expression of a operably-linked gene, in particular a operably-linked gene encoding the enzyme phytase, causing enhanced levels of phytase in the grain. The invention further relates to animal feed comprising said cereal grain having enhanced amounts of phytase.

BACKGROUND DESCRIPTION OF THE INVENTION

Phytases (myo-inositol hexakisphosphate phosphohydrolase) [EC 3.1.3.26 and EC 3.1.3.8] are phosphatases that initiate the sequential liberation of orthophosphate groups from phytate (InsP$_6$, myo-inositol 1,2,3,4,5,6-hexakisphosphate), providing phosphate, inositol phosphates and inositol required for a range of cellular activities (Brinch-Pedersen et al., 2002). A number of enzymes with phytase activity are known from plants, animals and microorganisms (Dvorakova, 1998).

Phytases are of particular importance during seed germination where they mobilize phosphate from phytate, the major reserve of phosphorus (P) in plant seeds accounting for ~70% of the total P (Lott, 1984). Different plant species have developed various strategies for phytase mediated degradation of phytate during germination. Among cereals, barley (*Hordeum vulgare* L.), wheat (*Triticum aestivum* and durum L.) and rye (*Secale cereale* L.) synthesize and accumulate phytase during grain development and the mature seed has a significant level of preformed phytase activity. Levels of phytase activity of 582, 1193 and 5130 U kg$^{-1}$ have been detected in mature grain of barley, wheat and rye respectively (Eeckhout and de Paepe, 1994). Preformed phytase catalyses the first wave of phytate hydrolysis during early germination. Other cereals possess little (maize (*Zea mays* L.) ~41 U kg$^{-1}$) or close to no (rice (*Oryza sativa* L.)) preformed phytase activity in the mature seed and depend entirely on de novo synthesis during germination (Eeckhout and de Paepe, 1994).

The spatial and temporal regulation of phytase biosynthesis in plant seeds has profound effects on phosphate bioavailability when dry grains are used as food and feed. Monogastric animals such as pigs, poultry and humans have little or no phytase activity in their digestive tracts and thus depend on either a phosphate supplement or on the presence of the enzyme phytase in their diet, in order to meet their nutritional phosphate requirements. In most cases the amount of preformed phytase activity in mature cereal grain is not sufficient to ensure sufficient phytate degradation when included in animal feed. As a consequence, most of the cereal grain phytate consumed by an animal is excreted, thereby adding to the phosphate load on the environment which can be massive in areas with intense livestock production. One current solution to this problem has been to supplement animal feed, on a large scale, with inorganic phosphate, in order to meet an animal's need for phosphate. However, this solution can only continue in the short term since phosphate is a non-renewable resource, which will be depleted within a few decades. An alternative solution relies on the addition of phytase enzyme, in particular microbial-derived phytase, to feed intended for intense pig and poultry production. It has become common practise to include the enzyme phytase in pre-mixes for addition to animal fodder, and animal fodder, which is an additional cost factor. Thus there exists a need for alternative cheaper methods for enhancing the bioavailability of phosphate in cereals used for animal feed.

A DNA sequence comprising a coding sequence for wheat phytase has been deposited in GenBank (AX298209). Patent application (WO2001/083763A2) describes said wheat phytase as a 66 kDa PAPhy with the same temperature and pH optima as PHYI (Rasmussen et al., 2004), and describes the production of transgenic wheat plants comprising said coding sequence.

SUMMARY OF THE INVENTION

According to a first embodiment, the present invention provides a mutant cereal plant comprising a polynucleotide selected from any one of:
  a. ACA VGA GTC ATG CAT [SEQ ID NO: 1] or T AGA ACA VGA GTC ATG CAT [SEQ ID NO: 2] wherein V is any nucleotide other than T, more preferably where V is C or G,
  b. polynucleotide comprising a nucleotide sequence selected from SEQ ID NO: 5, 6, 14, 15 and 44,
  c. polynucleotide comprising a nucleotide sequence selected from SEQ ID NO: 1, 5, 6, 14, 15 and 44, wherein said polynucleotide is operably linked to a second polynucleotide encoding a polypeptide,
wherein said polynucleotide is capable of enhancing gene expression in a grain of said plant, and, and wherein said cereal is selected from *Avena* L species, *Hordeum* L species; *Oryza* L species; *Secale* L species; *Sorghum* L species; *Triticum aestivum, Triticum durum; Triticum* spelta and *Zea* species.

In a further embodiment, the polypeptide of the mutant cereal plant is phytase [EC 3.1.3.26 and EC 3.1.3.8] and has myo-inositol hexakisphosphate phosphohydrolase activity.

Further to the first embodiment according to (a), the genomic DNA of the mutant cereal plant comprises a first polynucleotide located 5' upstream of a second polynucleotide, and operably-linked to the second polynucleotide, wherein said first polynucleotide comprises the nucleotide sequence ACA VGA GTC ATG CAT [SEQ ID NO: 1] or T AGA ACA VGA GTC ATG CAT [SEQ ID NO: 2], and wherein said second polynucleotide encodes a phytase polypeptide having myo-inositol hexakisphosphate phosphohydrolase activity.

Further to the above embodiments, the mutant cereal plant is selected from *Avena sativa*, (Oats); *Hordeum vulgare* (Barley); *Oryza sativa* (rice); *Secale cereale* (Rye); *Sorghum bicolor; Triticum aestivum, Triticum durum; Triticum spelta* (wheat species); *Zea mays* (maize).

Further to the above embodiments, the mutant cereal plant is a *Triticum* spp., and the phytase polypeptide has an amino acid sequence having at least 70% sequence identity to a sequence selected from SEQ ID NO: 18, 20, and 22.

Further to the above embodiments, the mutant cereal plant is a *Secale* spp., and the phytase polypeptide has an amino acid sequence having at least 70% sequence identity to a sequence selected from SEQ ID NO: 26 or 28.

Further to the above embodiments, the mutant cereal plant is a *Hordeum* spp., and the phytase polypeptide has an amino acid sequence having at least 70% sequence identity to a sequence selected from SEQ ID NO: 30.

Further to the above embodiments, the mutant cereal plant is selected from a mutant of *Triticum aestivum* having Deposit No: PTA-11732 [TaHighPhy 01], and PTA-11731 [TaHighPhy 02]; and a mutant of *Secale cereale* having Deposit No PTA-11730 [ScHighPhy 01], said plants being deposited with ATCC Patent Depositary, 10801 University Blvd., Manassas, Va. 20110, Further to the above embodiments, the mutant cereal plant is a grain.

According to a second embodiment, the invention provides a plant part (e.g. grain or caryopsis) derived from a mutant cereal plant of the first embodiment or further embodiments of the invention.

According to a third embodiment, the invention teaches the use of grain derived from a mutant cereal plant according to the first or further embodiments of the invention, for the manufacture of a composition, wherein said composition is any one of: a milled grain composition; animal fodder; and steam-pelleted animal fodder.

According to a fourth embodiment, the invention provides a composition comprising a mutant cereal plant according to the first or further embodiments of the invention, wherein said composition is any one of: a milled grain composition; animal fodder and steam-pelleted animal fodder.

According to a fifth embodiment, the invention teaches a use of a composition, comprising a mutant cereal plant, according to the fourth embodiment as animal fodder.

According to a sixth embodiment, the invention teaches a method for detecting a mutant cereal plant, said plant comprising a polynucleotide selected from one of:

a) ACA VGA GTC ATG CAT; [SEQ ID NO: 1]

b) a polynucleotide comprising a nucleotide sequence selected from SEQ ID NO: 5, 6, 12, 14 and 15, and c) polynucleotide comprising a nucleotide sequence selected from SEQ ID NO: 1, 5, 6, 12, 14 and 15, wherein said polynucleotide is operably linked to a second polynucleotide encoding a polypeptide, and wherein said polynucleotide is capable of enhancing gene expression in a grain of said plant, comprising the steps of: (i) isolating genomic DNA from said plant, and (ii) detecting the presence of the nucleotide V at the 5' end of a polynucleotide having the nucleotide sequence ACA VGA GTC ATG CAT [SEQ ID NO: 1] or T AGA ACA VGA GTC ATG CAT [SEQ ID NO: 2], wherein said polynucleotide is comprised in said genomic DNA.

According to a seventh embodiment, the invention teaches a method for inducing and selecting a mutant cereal plant, said plant comprising a polynucleotide selected from one of:

a) ACA VGA GTC ATG CAT; [SEQ ID NO: 1]

b) a polynucleotide comprising a nucleotide sequence selected from SEQ ID NO: 5, 6, 12, 14 and 15, and c) polynucleotide comprising a nucleotide sequence selected from SEQ ID NO: 1, 5, 6, 12, 14 and 15, wherein said polynucleotide is operably linked to a second polynucleotide encoding a polypeptide, and wherein said polynucleotide is capable of enhancing gene expression in a grain of said plant, comprising the steps of: (i) treating a cereal plant, or plant part thereof, with a chemical mutagen; (ii) growing and/or multiplying the treated plant, or plant part; (iii) isolating genomic DNA from said plant or progeny thereof, and (d) detecting the presence of a polynucleotide having the nucleotide sequence ACA VGA GTC ATG CAT [SEQ ID NO: 1] or T AGA ACA VGA GTC ATG CAT [SEQ ID NO: 2], wherein said polynucleotide is comprised in said genomic DNA.

Further to the sixth or seventh embodiments, the genomic DNA comprises a first polynucleotide located 5' upstream of and operably-linked to a second polynucleotide, wherein the first polynucleotide comprises the nucleotide sequence ACA VGA GTC ATG CAT [SEQ ID NO: 1] or T AGA ACA VGA GTC ATG CAT [SEQ ID NO: 2], and wherein the second polynucleotide encodes a phytase polypeptide having myo-inositol hexakisphosphate phosphohydrolase activity.

Further to the sixth or seventh embodiments, the cereal is selected from *Avena* L spp, *Hordeum* L spp; *Oryza* L spp; *Secale* L spp; *Sorghum* L spp; *Triticum aestivum, Triticum durum; Triticum monococcum*; and *Zea* spp.

Further to the sixth or seventh embodiments, the cereal is selected from *Avena* L spp, *Hordeum* L spp; *Oryza* L spp; *Secale* L spp; *Sorghum* L spp; *Triticum aestivum, Triticum durum; Triticum monococcum*; and *Zea* spp, and the amino acid sequence of the phytase polypeptide has at least 70% sequence identity to a sequence selected from SEQ ID NO: 18, 20, 22, 24, 26, 28, and 30.

Further to the sixth or seventh embodiments, the cereal is selected from *Avena* L spp, *Hordeum* L spp; *Oryza* L spp; *Secale* L spp; *Sorghum* L spp; *Triticum aestivum, Triticum durum; Triticum monococcum*; and *Zea* spp, and the amino acid sequence of the phytase polypeptide has at least 70% sequence identity to a sequence selected from SEQ ID NO: 18, 20, 22, 24, 26, 28, and 30, wherein said polypeptide is encoded by a polynucleotide having a nucleotide sequence having at least 70% sequence identity to a sequence selected from SEQ ID NO: 17, 19, 21, 23, 25, 27, 29, and nucleotides 2091-4090 of 45, respectively.

DETAILED DESCRIPTION OF THE INVENTION

Listing of the Figures:

FIG. 1. Phytase activity in mature whole grain derived from 52 individual lines of wheat (*Triticum aestivum*).

Figure 2:
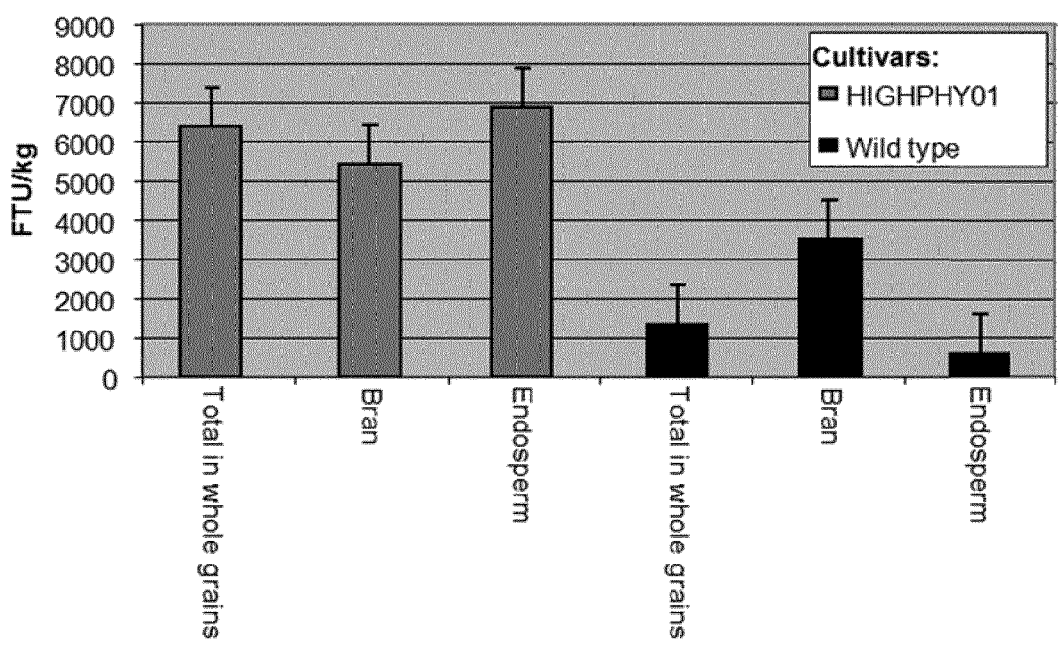

FIG. 2. Phytase activity in mature whole grain, bran and endosperm fractions of grain derived from 52 individual lines of wheat (*Triticum aestivum*).

Figure 3:
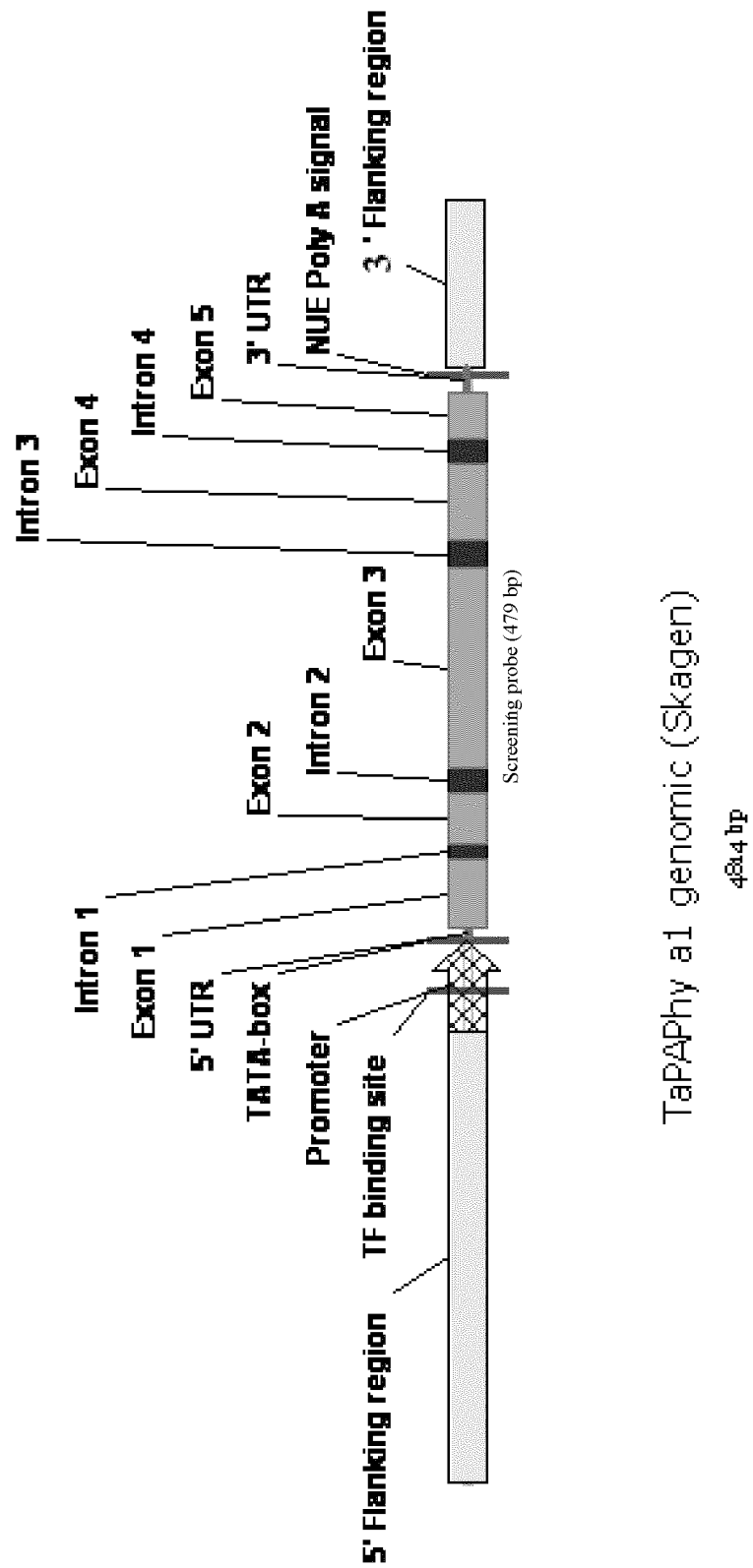

FIG. 3. Cartoon showing the exon-intron structure of a TaPAPhy a1 gene isolated from *Triticum aestivum* cv Skagen (TaG2) corresponding to SEQ ID NO: 45.

FIG. 4. Pair wise comparison of the nucleotide sequence of the 1000 bp 5' flanking promoter region of phytase genes amplified from 9 *T. aestivum* cultivars and the corresponding promoter region from two HighPhy *T. aestivum* cultivars. The upper comparison counts differences, whereas the lower comparison shows the identity in percent.

FIG. 5. Pair wise comparison of the nucleotide sequence of the 288 bp 5' flanking promoter region of phytase genes amplified from eight *T. aestivum* cultivars, two *T. tauschii* accession lines (NGB90403; NGB9855), and the corresponding promoter regions from two HighPhy *T. aestivum* cultivars. The upper comparison counts differences, whereas the lower comparison shows the identity in percent.

FIG. 6. Multiple alignment of the start codon and 288 bp 5' flanking promoter region 7 *T. aestivum* cultivars (cv Skagen; cv Bob White; cv Pentium; cv Flair; cv landrace 01; cv Landrace 02; cv Spelt, which share SEQ ID NO: 7), two *T. tauschii* accession lines (NGB90403; NGB9855, which share SEQ ID NO: 8), and the corresponding promoter regions from two HighPhy *T. aestivum* lines (HighPhy 01; HighPhy 02 which share SEQ ID NO: 5). The 5' flanking promoter region of the *T. aestivum* cv Skagen is represented by both the lambda clone TaG2 and a PCR amplicon, with SEQ ID NO: 7. The enhancer sequence [ACA CGA GTC ATG CAT] in the HighPhy 01 and 02 cultivars is located a position: −247 to −237 in the 5' flanking region. Note that SEQ ID NO: 5, 7 and 8 are identical to the corresponding sequences in FIG. 6, but with the exception that the last 3 nucleotides (ATG) of each corresponding sequence in FIG. 6 are excluded from the sequence given in the SEQ ID NO listing.

Figure 7:
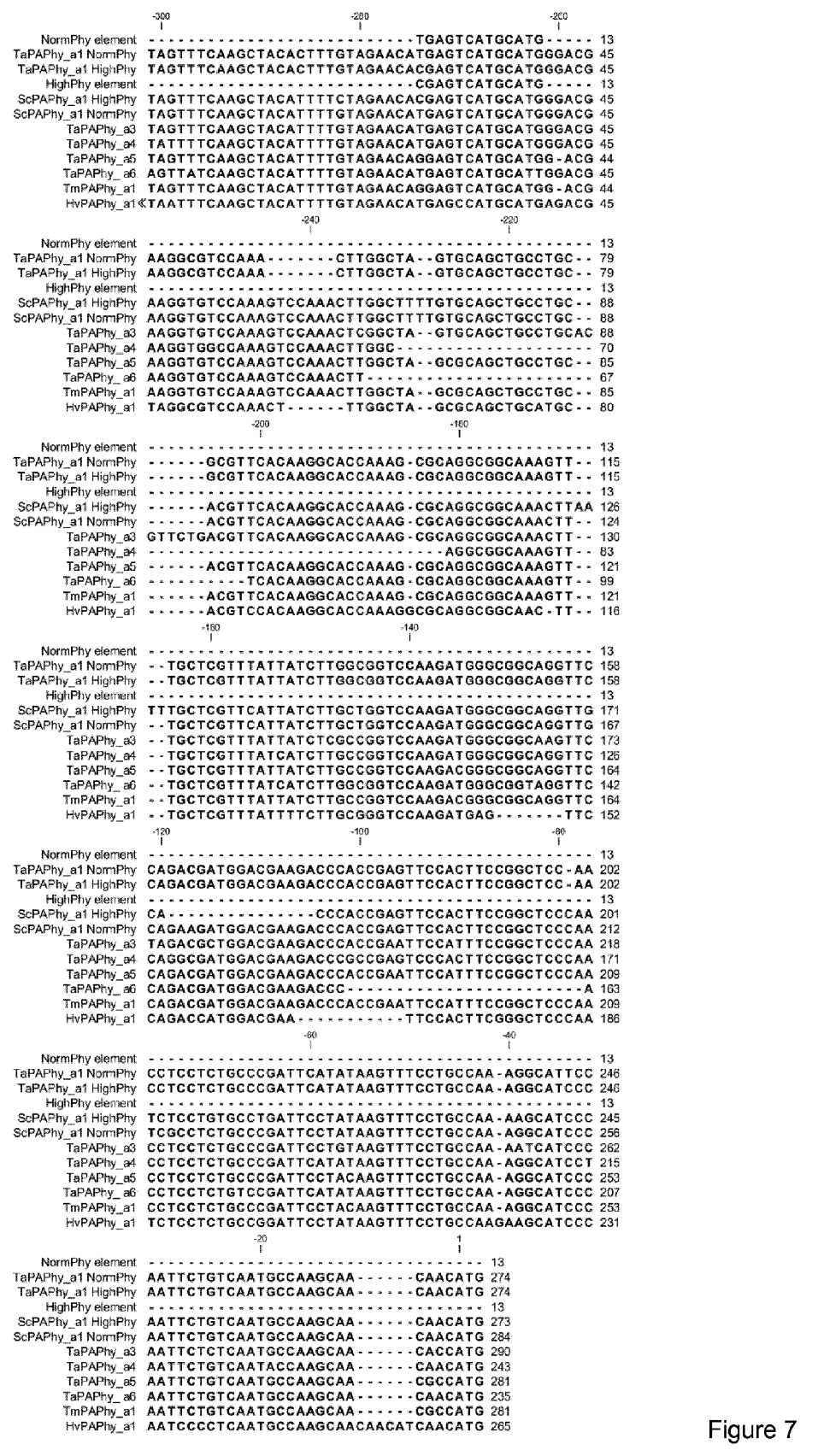

FIG. 7. Multiple alignment of the start codon and 5' flanking promoter region 5 wild type *T. aestivum* cultivars (TaPAPhy_a1: NormPhy [SEQ ID NO: 9]; TaPAPhy_a3 [SEQ ID NO: 10], TaPAPhy_a4 [SEQ ID NO: 11]; TaPAPhy_a5; TaPAPhy_a6) and the corresponding promoter region from a High Phytase *T. aestivum* line (TaPaPhy_a1: HighPhy [SEQ ID NO: 6]). The 5' flanking promoter region of the *T. monococcum* (TmPAPhy_a1 [SEQ ID NO: 12]); *Hordeum vulgare* (HvPAPhy_a1 [SEQ ID NO: 13]) and high and normal phytase *Secale cereale* (ScPAPhy_a1 HighPhy [SEQ ID NO: 15]) and (ScPAPhy_a1 NormPhy [SEQ ID NO: 16]). Note that SEQ ID NO: 6, 9, 10, 11, 13, 13, 15 and 16 are identical to the corresponding sequences in FIG. 7, but with the exception that that the last 3 nucleotides (ATG) of each corresponding sequence in FIG. 6 excluded from the sequence given in the SEQ ID NO listing. The nucleotide sequence of the polynucleotides comprised within the NormalPhy element and the HighPhy enhancer element are included in the alignment.

Figure 8:
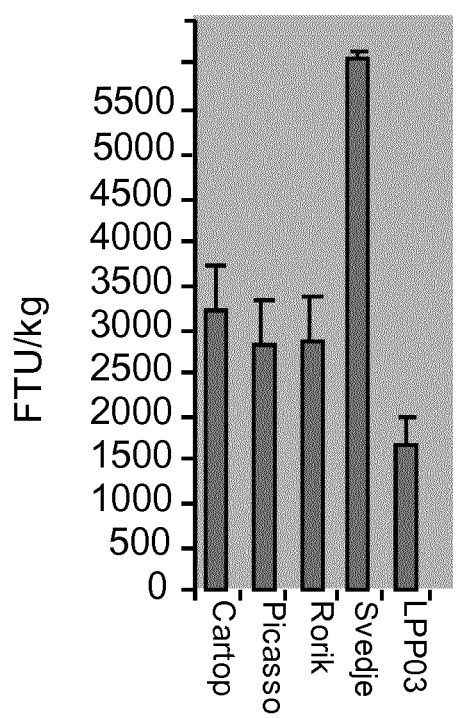

FIG. 8. Phytase activity in mature whole grain derived from 5 individual lines of rye (*Secale cereale*). One line (LPP03) has low phytase activity and 4 lines have medium to high phytase activity.

Figure 9:
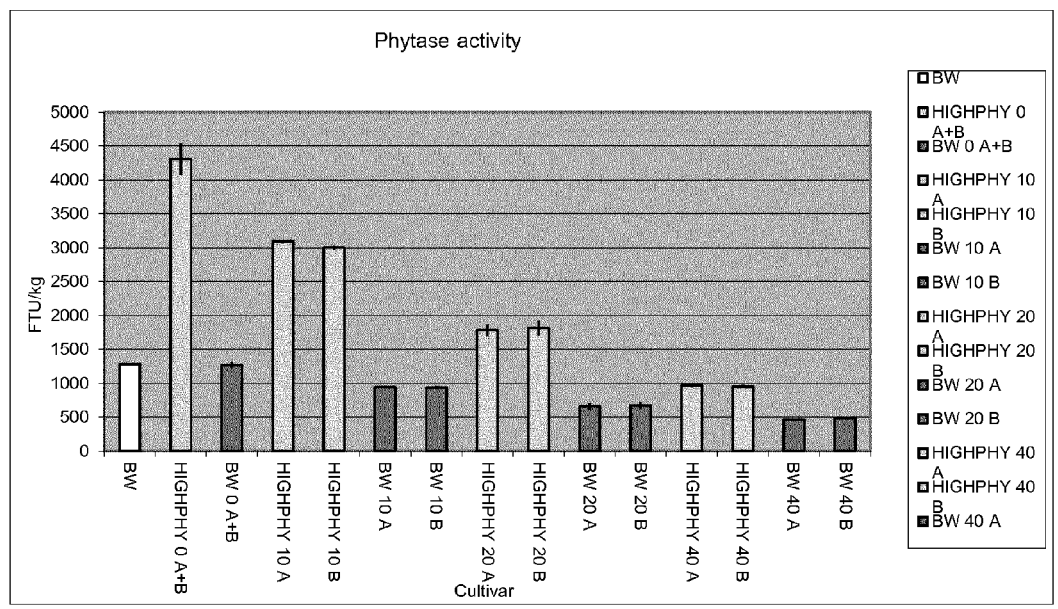

FIG. 9. Phytase activities in Bob White wild type (BW) and HighPhy *T. aestivum* (HIGHPHY) wheat flour after 0, 10, 20 and 40 min of incubation at 80° C. in 100% relative humidity.

Figure 10:
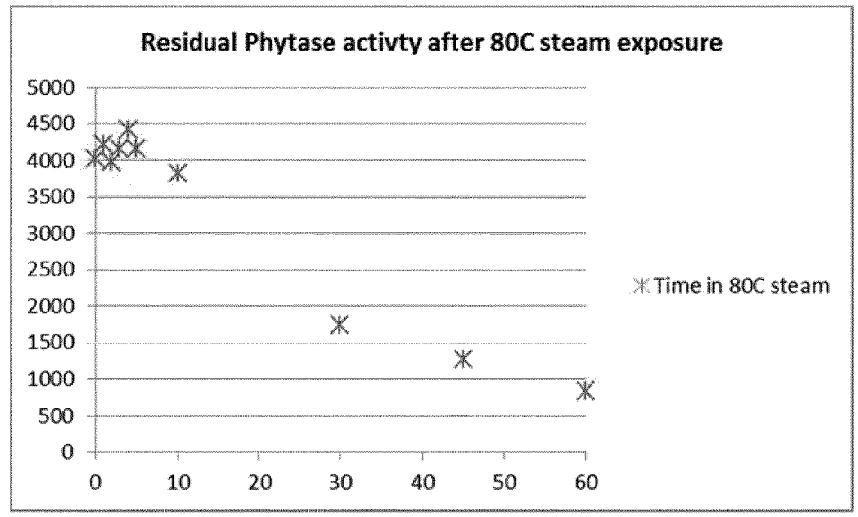

FIG. 10. Phytase activities in HighPhy *Secale cereale* (rye) flour after 0, 1, 2, 3, 4, 5, 10, 30, 45 and 60 min of incubation at 80° C. in 100% relative humidity.

Figure 11:
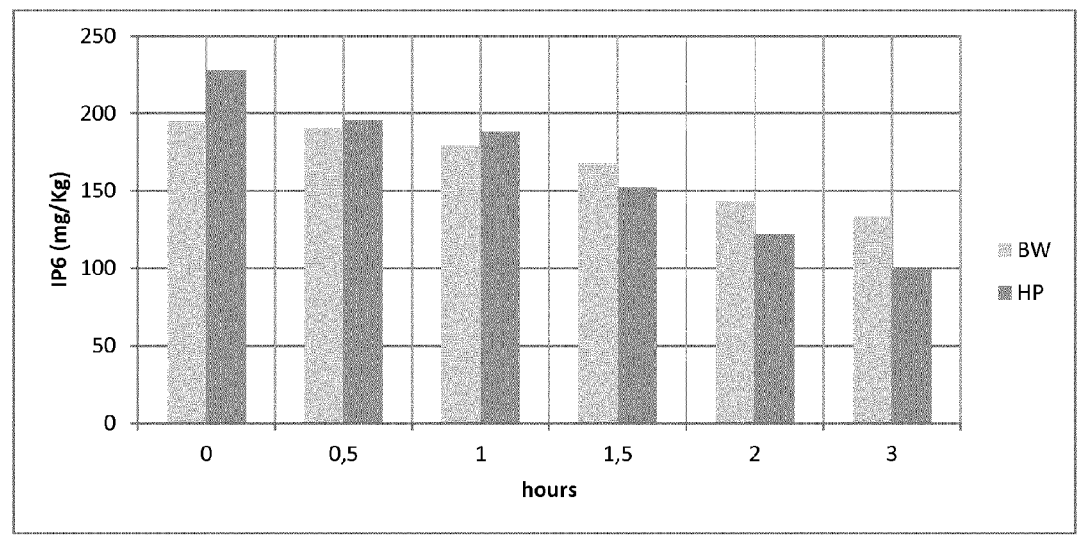

FIG. 11. Phytate content in Bob White wild type (BW) and HighPhy *T. aestivum* (HIGHPHY) wheat dough during the fermentation FIG. 12. Percentage residual phytate in flour of Bob White wild type and HighPhy *T. aestivum* (HIGHPHY) wheat after 0.5, 1, 1.5, 2 and 3 hrs of fermentation.

Figure 13:
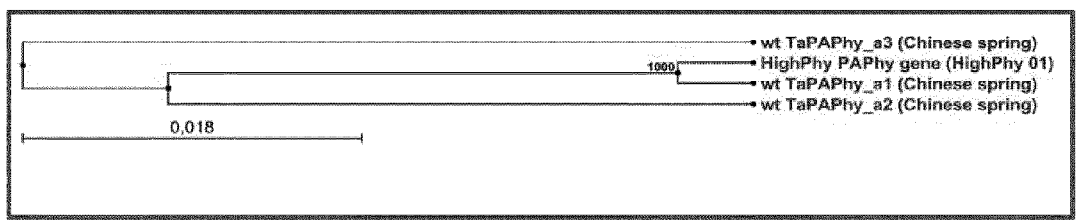

FIG. 13. UPGMA tree of the HIGHPHY and TaPAPhy_a1, _a2 and a_3 genes.

ABBREVIATIONS

AS-PCR: Allele specific-polymerase chain reaction;
CTP: cytosine 5'-triphosphate;
dNTP: Deoxynucleotide Triphosphate;
PAPhy: Purple acid phosphates (PAP) with phytase activity; also called PAP phytases (PAPhy);
Pfu: plaque forming units;
SNP: single-nucleotide polymorphism is a DNA sequence variation occurring when a single nucleotide (A, T, C, or G) in the genome differs between members of a species or paired chromosomes in an individual
1×SSPE buffer: 150 mM Sodium Chloride, 10 mM Sodium Hydrogen
Phosphate, 1 mM EDTA, pH 7.4);
SPP: species;
V: is the nucleotide A or C or G (not T), where B is the nucleotide in the complementary sequence.

DEFINITIONS

Cereal: A plant belonging to the Poaceae family, in particular a plant belonging to the Genus and species thereof: *Avena* L (e.g. *Avena sativa*, Oats); *Hordeum* L e.g. *Hordeum vulgare*, Barley); *Oryza* L (e.g. *Oryza sativa*, rice); *Secale* L (e.g. *Secale cereale*, Rye); *Sorghum* L (e.g. *Sorghum bicolor*); *Triticum* (e.g. *Triticum aestivum, Triticum durum; Triticum monococcum, Triticum spelta*, wheat); *Zea* (e.g. *Zea mays*, maize).

Promoter operably-linked to a gene: a promoter is a DNA molecule that is located on the same DNA strand and upstream (towards the 5' region of the sense strand) of the transcriptional start site of a down-stream gene, where the operational function of the promoter is to regulate the expression of the down-stream gene to which it is operably-linked. DNA molecules, whose function is to regulate expression of a down-stream gene, typically comprise a smaller DNA molecule that acts as an "enhancer", the enhancer serving to modulate expression levels of the down-stream gene. An "Enhancer" is characterised by a conserved nucleotide sequence, often comprising various conserved sequence motifs whose function is to modulate gene expression levels. A gene is defined to include a polynucleotide molecule comprising coding and optionally non-coding sequence(s), the coding sequence(s) encoding a polypeptide, e.g. phytase.

*Triticum aestivum*: line of *T. aestivum*, cultivar of *T. aestivum* is a cultivated variety of *T. aestivum* that has been created or selected intentionally for specific desirable characteristics and maintained through cultivation.

Sequence identity: Identity can be measured as percent identity. The term "percent sequence identity" indicates a quantitative measure of the degree of homology between two nucleotide sequences of equal length. When the two sequences to be compared are not of equal length, they are aligned to give the best possible fit, by allowing the insertion of gaps or, alternatively, truncation at the ends of the nucleotide sequences. The (Nref−Ndlf)l00 can be calculated as <Nref>, wherein Nd[iota]f is the total number of non-identical residues in the two sequences when aligned and wherein Nref is the number of residues in one of the sequences. The percent sequence identity between one or more sequence may also be based on alignments using the clustalW software world wide web at ebi.ac.uk/clustalW/index.Html.

DETAILED DESCRIPTION OF EMBODIMENTS OF THE INVENTION

It is recognised that, in most cases, the amount of preformed phytase activity in mature cereal grain is not sufficient to ensure sufficient phytate degradation when included in animal feed. It is further recognised that bread dough having a low phytate content has superior mixing properties, and the resulting bread has a higher nutritional value, due to an enhanced availability of minerals, including inorganic phosphate. One solution to this problem has been to produce genetically modified cereal plants having higher levels of phytase in the grain, for example by expressing a transgene encoding a heterologous or homologous gene encoding phytase. Current agricultural policy in many parts of the world, in particular Europe, has restricted the growth of transgenic crop plants. Furthermore, organic farming, based on methods that are internationally regulated and legally enforced by many nations, are not certified to use genetically modified plants or feed enzymes derived from microbial phytases. Accordingly, there remains a need for non-transgenic plants producing grain having a high phytase phenotype. The present invention addresses this need.

I. A Polynucleotide Acting as an Enhancer of Grain-Specific Gene Expression in Mutant Cereal Plant One embodiment of the invention provides a mutant cereal plant whose genome comprises an enhancer polynucleotide having the nucleotide sequence:

ACA VGA GTC ATG CAT,    [SEQ ID NO: 1]
or

T AGA ACA VGA GTC ATG CAT,    [SEQ ID NO: 2]

wherein said polynucleotide is capable of enhancing grain-specific gene expression. The enhancer polynucleotide comprises a mutation whereby the nucleotide V is any nucleotide other than T (i.e. C or G or A), as compared to the corresponding polynucleotide in a wild type cereal plant having normal wild type levels of phytase (e.g. the enhancer in the wild type normal phytase polynucleotide ACA TGA GTC ATG CAT [SEQ ID NO: 3] from wheat). In a preferred embodiment, the enhancer polynucleotide has SEQ ID NO: 1, wherein the nucleotide residue designated as V, is either G or C.

A series of four overlapping motifs have been identified in the polynucleotide having the sequence:

AACATGAGTCATGCATGGGA    [SEQ ID NO: 4]

which comprises the enhancer of the wild type wheat phytase gene. These motifs include an "odd base palindrome sequence" and a "GCN4 motif", a "skn-1 motif" and a "palindomic RY-repeat". The odd base palindrome and GCN4 motif have been shown to interact with Opaque2, a maize basic leucine zipper (bZIP) transcription factor that is involved in the regulation of seed storage protein expression [3,4], whereas the RY-repeat has been shown to interact with transcription factors containing the B3 domain.

Cereal plants comprising the mutant enhancer polynucleotide, show enhanced grain-specific expression of an operably-linked gene located down-stream of the enhancer polynucleotide, indicating that the mutant polynucleotide acts to regulate enhanced gene expression in a tissue-specific manner. Proteins encoded by the operably-linked gene, whose expression in cereal plants is regulated by a structurally- and operably-linked upstream promoter polynucleotide molecule comprising the enhancer polynucleotide having SEQ ID NO: 1 or 2, accumulate enhanced levels of the encoded protein in the grain when compared to wild-type cereal plants having the wild-type enhancer sequence (see Example 1 and 7).

The enhancer polynucleotide according to the invention is further characterised by an altered expression pattern of its operably-linked gene in the grain. The enhancer causes both increased gene expression throughout the grain, but also preferential expression in the endosperm tissue of the grain, which constitutes the majority of the grain as measured by weight (Example 1 and 13). The enhanced gene expression leads to enhanced levels of the gene-encoded proteins in the endosperm of the grain, having the advantage that downstream grain processing steps, such a dehusking/milling does not lead to a loss the protein as is the case for proteins expressed in the aleurone tissue, and outer layers/coat of the grain.

II. A Mutant Cereal Plant, Whose Genome has a Promoter Polynucleotide Comprising an Enhancer of Grain-specific Gene Expression A further embodiment of the invention provides a mutant cereal plant, whose genome comprises a promoter polynucleotide molecule, said molecule comprising the enhancer polynucleotide having SEQ ID NO: 1 or 2. The mutant cereal plant of the invention is a member of the Poaceae family, preferably belonging to the Genus L, and Species (spp) thereof of the following: *Avena* L (e.g. *Avena sativa*); *Hordeum* L (e.g. *Hordeum vulgare*); *Oryza* L (e.g. *Oryza sativa*); *Secale* L (e.g. *Secale cereale*); *Sorghum* L (e.g. *sorghum bicolor*); *Triticum* spp selected from *Triticum aestivum, Triticum Durum*; and *Triticum spelta*; and *Zea* (e.g. *Zea mays*).

In one example, the mutant cereal plant is a mutant *Triticum aestivum*, whose genome comprises the enhancer polynucleotide having SEQ ID NO: 1 or 2. The genome of the mutant *Triticum aestivum* may comprise a promoter polynucleotide having SEQ ID NO: 5 or 6 or 44, this promoter itself comprising the enhancer polynucleotide having SEQ ID NO: 2. Wheat plants comprising a promoter having SEQ ID NO: 5 or 6 show enhanced endosperm-specific expression of a operably-linked gene located downstream of this promoter, indicating that the promoter acts to regulate enhanced gene expression in a tissue-specific manner. The corresponding promoter polynucleotide in wild-type *Triticum aestivum* cv's and *Triticum tauschii* that lack the enhancing properties of the mutant are provided as SEQ ID NO: 7, 10 and 11 and in 8 respectively.

In one example, the mutant cereal plant is a mutant *Secale cereale* whose genome comprises the enhancer polynucleotide having SEQ ID NO: 1 or 2. The genome of the mutant *Secale cereale* may comprise a promoter polynucleotide having SEQ ID NO: 15, this promoter itself comprising the enhancer polynucleotide having SEQ ID NO: 2. The corresponding promoter polynucleotide in wild-type *Secale cereale* that lacks the enhancing properties of the mutant is provided as SEQ ID NO: 16.

In one example, the mutant cereal plant is a mutant *Hordeum vulgare* whose genome comprises the enhancer polynucleotide having SEQ ID NO: 1 or 2. The genome of the mutant *Hordeum vulgare* may comprise a promoter polynucleotide having SEQ ID NO: 14, this promoter itself comprising the enhancer polynucleotide having SEQ ID NO: 1. The corresponding promoter polynucleotide in wild-type *Hordeum vulgare* that lacks the enhancing properties of the mutant is provided as SEQ ID NO: 13.

III A Mutant Wheat Plant with High Phytase Grain

A further embodiment of the invention provides a mutant cereal plant comprising a promoter polynucleotide, said promoter comprising the enhancer polynucleotide having SEQ ID NO: 1 or 2, wherein said promoter polynucleotide lies upstream and is operably linked to a cognate phytase gene encoding a polypeptide having myo-inositol hexakisphosphate phosphohydrolase activity (phytase [EC 3.1.3.26 and EC 3.1.3.8]).

In one example, the cereal plant is a mutant *Triticum aestivum* plant comprising the enhancer polynucleotide having SEQ ID NO: 1 or 2, where the promoter polynucleotide preferably has SEQ ID NO: 5 or 6, or 44, and the cognate phytase gene encodes a polypeptide having both myo-inositol hexakisphosphate phosphohydrolase activity and an amino acid sequence having at least 70, 75, 80, 85, 90, 95 or 98% sequence identity to a sequence selected from SEQ ID NO: 18, 20, and 22. In a further embodiment, said phytase polypeptide having an amino acid sequence selected from SEQ ID NO: 18, 20, and 22 is encoded by a polynucleotide having a nucleotide sequence that has at least 70, 75, 80, 85, 90, 95 or 98% sequence identity to a sequence selected from SEQ ID NO: 17, 19, 21, and 45 (nucleotides 2091-4090), respectively.

In one example, the cereal plant is a mutant *Secale cereale* plant comprising the enhancer polynucleotide having SEQ ID NO: 1 or 2, where the promoter polynucleotide preferably has SEQ ID NO: 15, and the cognate phytase gene encodes a phytase polypeptide having both myo-inositol hexakisphosphate phosphohydrolase activity and an amino acid sequence having at least 70, 75, 80, 85, 90 or 95% sequence identity to a SEQ ID NO: 26 or 28. In a further embodiment, said phytase polypeptide having an amino acid sequence of SEQ ID NO: 26 or 28 is encoded by a polynucleotide having nucleotide sequence that has at least 70, 75, 80, 85, 90 or 95% sequence identity to SEQ ID NO: 25 or 27, respectively.

In one example, the cereal plant is a mutant *Hordeum vulgare* plant comprising the enhancer polynucleotide having SEQ ID NO: 1 or 2, where the promoter polynucleotide preferably has SEQ ID NO: 14, and the cognate phytase gene encodes a phytase polypeptide having both myo-inositol hexakisphosphate phosphohydrolase activity and an amino acid sequence having at least 70, 75, 80, 85, 90 or 95% sequence identity to a SEQ ID NO: 30. In a further embodiment, said phytase polypeptide having an amino acid sequence of SEQ ID NO: 30 is encoded by a polynucleotide having nucleotide sequence that has at least 70, 75, 80, 85, 90 or 95% sequence identity to SEQ ID NO: 29.

III Methods for Detecting a Cereal Germplasm Comprising the HighPhy SNP

The polynucleotide: "ACA$^V$GAGTCATGCATG" (SEQ ID NO: 62) in the genomic DNA of a cereal plant e.g. *Triticum* spp, characteristic of the HighPhy SNP, can be detected using standard DNA analysis protocols (see Example 5). For example, amplification of genomic DNA comprising the HighPhy SNP with the forward TTTCAAGCTACACTTTGTAGAACAC [SEQ ID NO: 39] and reverse GCACTAGCCAAGTTTGGACG [SEQ ID NO: 40] primers will generate a 66 bp PCR product when using Taq polymerase, whereas amplification of genomic DNA comprising a "wildtype cereal" with wild-type levels of normal phytase will give a similar product with forward TTTCAAGCTACACTTTGTAGAACAT [SEQ ID NO: 41] and reverse GCACTAGCCAAGTTTGGACG [SEQ ID NO: 42] primers (where the second primer [SEQ ID NO: 42] is universal).

IV Methods for Inducing and Selecting Cereal Germplasm Comprising the HighPhy SNP HighPhy cereals (e.g. *Triticum* spp) can be generated by mutagenesis and subsequent screening for individuals where the polynucleotide:

ACA TGA GTC ATG CAT (SEQ ID NO: 3), corresponding to the wild type (NormPhy) enhancer, in the cereal genome has been converted into the mutant (HighPhy) enhancer:

ACA VGA GTC ATG CAT (SEQ ID NO: 1), where V can be A or C or G.

In one embodiment the mutagenesis is carried out with sodium azide which preferentially generates A:T to G:C substitutions in the cereal, barley (8). Screening mutagenized populations for the desired mutation could be done by allele specific polymerase chain reaction (AS-PCR), as described in Example 6.

In an alternative embodiment, mutagenesis is carried out on cereal grain using methylene Methyl Sulphonate (MMS) to generate a population of M1 plants with random point mutations in their genome. MMS treatment leads to errors during DNA replication and thus introduces mutations. Typically this means T/A nucleotides within a sequence are converted to G/C by transversion. The M1 plants are self-fertilised and the M2 seed harvested and sown. The M2 germplasm will allow recessive and lethal alleles to be recovered as heterozygotes. DNA is individually extracted from M2 plants into 96 well plates and their seed stored for further propagation. To increase throughput of analysis, the M2 DNA samples are 8× pooled and amplified, using gene specific primers, located up- and down-stream of the mutant (HighPhy) enhancer: ACA VGA GTC ATG CAT (SEQ ID NO: 1)that is to be detected. Preferably each primer carries a different fluorescent label. For example, the forward strand may be labelled with FAM [5-Carboxyfluorescein; 3',6'-Dihydroxy-3-oxospiro[2-benzofuran-1,9'-xanthene]-5-carboxylic acid, CAS #: 76823-03-5] and the reverse strand with HEX [HEX being a hexa-chloro derivative of FAM]. In the presence of a mutant, the amplification products when heated and cooled will form mismatched heteroduplexes between the wild type and mutated DNA. To enable identification of the point mutations induced by EMS, the amplification products are incubated with a plant endonuclease called CEL I which preferentially cleaves at sites of heteroduplex mismatches that occur between wild-type and mutant DNA. The cleavage products are size-separated on a DNA sequencing instrument, for example a capillary DNA sequencer and the fluorescently labelled traces are analysed. The differential end-labelling of the amplification products permits the two cleavage fragments to be observed and to identify the position of the mismatch. When a mutation is detected in the pooled DNA, the DNA samples in the pool are individually sequenced to identify the specific plant carrying the mutation.

The amount of phytase enzyme in the grain of plants having the mutant (HighPhy) enhancer: ACA VGA GTC ATG CAT (SEQ ID NO: 1) in their genome, is then determined to confirm that the selected mutant has the high phytase phenotype, for example by employing the phytase assay described in Example 1.

V Use of High-phytase Cereal Grain for Producing a Composition

Processing of cereal grain (for example wheat of rye grain) having phytase activity in accordance with the present invention, is carried out using traditional processing steps including one or more of the following steps:

i. Cleaning/conditioning cereal grain: First the grain is cleaned. For example the grain may be passed through magnets and/or metal detectors to remove any metal contamination. Machines can be used to separate any other seeds, stones or dust that may have got mixed with the wheat.

ii. Gristing grain: The cleaned and conditioned grain is blended with other types of grain in different proportions to make different kinds of flour. The gristed grain passes through special rollers called break rolls. They break each grain into its three parts: cereal grain germ, bran and endosperm. Sieves sift the three separated parts into different streams.

iii Mixing: The bran, germ and endosperm fractions, having been separated out, can optionally be blended, and can be milled to make different types of milled cereal grain composition, such as Wholemeal flour using all parts of the grain; Brown flour contains about 85% of the original grain, but with some bran and germ removed; and White flour is made from the endosperm only. A flour mix comprising flour prepared from high-phytase cereal grains of the invention has particular value for bread making, due to the rapid degradation of phytate during dough fermentation (see Example 12) that confers both improved dough mixing properties and enhances the nutritional value (by increasing mineral uptake from the diet, in particular zinc, iron, calcium and inorganic phosphate ions) of the bread produced with the dough.

iv. Steam pelleting: Milled cereal grain composition may be combined with other fodder ingredients in a steam-pelleting machine, where the components are exposed to steam at a temperature of about 80° C.-90° C. for a period of time sufficient to reduce the microbial population to levels safe for animal consumption, and the product is converted to dried pellets. Steam pelleted animal feed prepared from HighPhy cereal grain of the invention retain sufficiently high levels of phytase activity following steam-treatment, that addition of supplementary phytase granules can be avoided.

VI A Composition Comprising High-phytase Cereal Grain

In a further embodiment, the present invention provides animal fodder comprising grain derived from the mutant cereal plant of the present invention (for example a wheat, rye or barley high-phytase mutant), where the grain are characterized by enhanced levels of phytase. Animal fodder comprising grain from the mutant wheat plant have the advantage, that the need to supplement the fodder with phytase is considerably reduced and preferably avoided, and at the same time the added high phytase cereal grain has the advantage that it is not classified as genetically modified material.

VII a Wild-type *Triticum aestivum* Gene TaPAPhy_a1

In a further embodiment, the present invention provides an isolated full-length *Triticum aestivum* gene TaPAPhy_a1 (SEQ ID NO: 45), comprising a promoter sequence (SEQ ID NO: 7) and down-stream coding sequence comprising 5 exons and 4 introns (FIG. 3). Part, or all, of the isolated TaPAPhy_a1 gene can be used for the construction of gene constructs for transformation into wheat.

EXAMPLE 1

Phytase Activity of Different *Triticum aestivum* Cultivars 1.1 Comparative Levels of Total Phytase Enzymatic Activity in Mature Wheat Grain The phytase activity was measured in mature seeds of 52 individual cultivars or lines of wheat (*Triticum aestivum*). Mature seeds were milled and protein was extracted from 0.250 g of flour by adding 2.5 ml 220 mM Na-acatete buffer (pH 5.5) including 68 mM $CaCl_2$ and Tween 20 (100 mg/l). The suspension was vortexed for 1 hour at room temperature and subsequently centrifuged at 3000×g for 10 min. The supernatant was collected and assayed for phytase activity as described by Engelen et al., 1994 [1]. One phytase unit (U) is defined as 1 μmol of Pi released upon phytate hydrolysis at 37° C. at the enzymes pH optimum.

Phytase activity ranged from ~650 to ~1900 FTU/kg in grain from 50 of the wheat lines (FIG. 1). Similar levels of phytase activity have previously been reported [2], in 13 individual wheat lines. However in two lines, HIGHGPHY01 and HIGHPHY02, the level of phytase activity was ~6000 FTU/kg and ~4300 FTU/kg respectively, exceeding all other wheat lines analysed.

2.2 Distribution of Phytase Enzymatic Activity in Mature Wheat Grain

The distribution of phytase activity between outer layers and endosperm tissues of wheat grain derived from HIGHPHY wheat lines and wild type wheat lines was determined. The wheat grain samples were milled and divided into outer bran and inner endosperm fractions. The phytase activities were measured in each fraction (FIG. 2). In wild-type wheat grains with a total activity on ~1200 FTU/kg, phytase activity was mainly localised in the bran fraction with ~3500 FTU/kg, while phytase activity in endosperm tissue was about ~600 FTU/kg. A significantly different distribution was seen in HIGHPHY01 grain, where the activity in the endosperm was 6900 FTU/kg, exceeding the level of phytase activity in both bran (5300 FTU/kg) and whole grains (6300 FTU/kg).

EXAMPLE 2

Isolation of a Wheat Phytase Gene 2.1 Construction of a Genomic Library from Genomic DNA from *Triticum aestivum*, cv Skagen:

A genomic library of DNA extracted from *Triticum aestivum*, cultivar Skagen, was generated using the Lambda Fix II/Xho I Partial Fill-In Vector Kit (Agilent Technologies-Stratagene Products) according to the manufacturer's instructions. The initial library was titered and the size found to be $5 \times 10^6$ pfu. Given the constraints of the vector, which will accommodate inserts of 9-23 kb, this corresponds to 45000-115000 Mb or 2.8-7.2 times the size of the wheat genome. The library was amplified on 150 120×120 mm NZY agar plates according to the manufacturer's instructions to achieve a final titer of $3 \times 10^6$ pfu/μL.

2.2 Screening a *Triticum aestivum*, cv Skagen Genomic Library for a Phytase Gene:

The amplified library was plated out on 240×240 mm NZY agar plates at a density of 600 pfu/cm². Plaque lifts were performed with Hybond N+ membranes (GE Healthcare), and the DNA was fixed on the membrane by alkaline denaturation and UV cross linking. The membranes were prehybridized in 0.25 M sodium phosphate buffer, pH 7.2, with 7% SDS and 0.17 mg/mL salmon sperm DNA at 65° C. for two hours in rolling tubes. The membranes were then hybridised in a solution comprising the radiolabelled Triticeae PAPhy specific Probe (20 microcuries), 0.25 M sodium phosphate buffer, pH 7.2, with 7% SDS at 65° C. overnight. Preparation of the probe is set out below. Ten membranes were washed at a time for 15 min in the hybridization tubes at 65° C. with 1×SSPE buffer followed by one wash for one hour at 65° C. in 1 L 1×SSPE buffer and 10 seconds in room temperature 1×SSPE. Finally the membranes were blot dried on filter paper for 10 min and sealed in plastic envelopes.

X-ray films were exposed with the membranes at −80° C., and the developed films subsequently analysed radiolabel signals. Positive clones were cut from the original plate and isolated by successive rounds of plaque screenings.

2.3 A Triticeae PAPhy Phytase Gene Specific Probe:

A 20 μCi $^{32}$P labelled probe was generated by PCR using [αP32]dCTP and the primers:

```
PAP ex3 Fw:   CTTGAGCCTGGGACGAAGT (SEQ ID NO: 31)
and

PAP ex3 Rv:   GAGAAGGACCCGCTCTCC, (SEQ ID NO: 32)
``` and a template consisting of a plasmid comprising a cDNA molecule whose nucleotide sequence encoded the wheat Purple Acid Phosphatase Phytase b (TaPAPhy_b). The primers amplified a portion of the cDNA molecule whose nucleotide sequence corresponds to the highly conserved third exon of the Triticeae PAPhy_b gene. The amplified sequence generated a DNA probe of 479 nucleotides in length. Remaining unincorporated dNTPs were removed with an Illustra MicroSpin G-50 Column (GE Healthcare). The probe was denatured by boiling followed by shock cooling in 500 μL of 10 μg/μL sonicated salmon sperm DNA.

2.4 Isolation and Characterisation of Triticeae PAPhy Phytase Gene:

Isolated lambda (λ) clones, selected by the Triticeae PAPhy specific probe, were amplified on five to twenty 82 mm diameter NZY agar plates and A DNA was isolated from the phage harvested from the plates using the Lambda midi kit (Qiagen) according to the manufacturer's instructions.

One isolated λ clone, comprising the genomic DNA molecule designated TaG2, was sequenced (SEQ ID NO: 45) and found to comprise a polynucleotide comprising a ~2000 bp promoter region having the sequence (SEQ ID NO: 43).

EXAMPLE 3

Amplification and Characterization of Phytase Gene Promotors from Different *Triticum aestivum* and *Triticum tauschii* Cultivars 3.1 Isolation of Phytase Gene Promoters by PCR Genomic DNA was isolated from 10 cultivars of *T. aestivum* and 2 accessions of *T. tauschii* (also known as *Ae. Tauschii*), as shown in table 1.

TABLE 1

Cultivars and accessions from which the TaPAPhy_a1 promoter was amplified.

| Cultivar/accession | Notes |
|---|---|
| Bob White | *T. aestivum* model cultivar |
| Skagen | *T. aestivum* commercial cultivar |

TABLE 1-continued

Cultivars and accessions from which the TaPAPhy_a1 promoter was amplified.

| Cultivar/accession | Notes |
|---|---|
| Flair | *T. aestivum* commercial cultivar |
| Spelt | *T. aestivum* spp *spelta* commercial sample |
| Pentium | *T. aestivum* commercial cultivar |
| Landrace 01 | *T. aestivum* Landrace |
| Landrace 02 | *T. aestivum* Landrace |
| HighPhy 01 | Novel high phytase *T. aestivum* cultivar |
| HighPhy 02 | Novel high phytase *T. aestivum* cultivar |
| NGB90403 | *T. tauschii* |
| NGB9855 | *T. tauschii* |

TaPAPhy_a1 promoter region was amplified from genomic DNA isolated from each of the above cultivars using primer pairs based on the sequence of the high phytase gene, designated, λ clone: TaG2. The first primer pair was designed for amplifying the first exon and 2041 bp 5' upstream flanking region (promoter) of the TaPAPhy_a1 gene:

```
                                   (SEQ ID NO: 33)
TaPAPhy_a1-pro-ex1 Fw:   TTATGTGTCCGCGTGAAGTG
and (SEQ ID NO: 34)
TaPAPhy_a1-pro-ex1 Rv:   ACCAAGAGTCAATGCCATCC
```

An additional primer pair was designed to amplify a shorter sequence which includes 288 bp of the 5' flanking region (promoter) and 147 bp of the first exon of the TaPAPhy_a1 gene:.

```
                                   (SEQ ID NO: 35)
TaPAPhy_a1 -311 cons Fw:  TTTGGACGAGCCATAGCTGCATA
and (SEQ ID NO: 36)
TaPAPhy_a1 167 Rv:        CGCTGCACCCGGGGGTCCGT
```

The latter primer pair was used with cultivars where the first primer pair failed to yield an amplification product.

PCR was performed with Herculase II (Agilent Technologies-Stratagene Products) according to the manufacturer's instructions, but with the modification that 6% DMSO was used in the reaction mixture.

Amplicons of the expected size were isolated from agarose gels and cloned in the pCR4Blunt TOPO vector (Invitrogen) and sequenced.

3.2 Characterization of the Promoter Region of Isolated *T. Aestivum* and *T. tauschii* Phytase Genes—Alignment of 1000 bp The long PCR amplicon, (corresponding to 2041 bp 5' upstream flanking promoter region the first exon and of the TaPAPhy_a1 gene) was obtained from 10 cultivars of *T. aestivum*, whereas only the short amplicon (corresponding to 147 bp of the first exon and 288 bp of the 5' flanking promoter region of the TaPAPhy_a1 gene) was obtained from two accessions of *T. tauschii*. The 1000 bp 5' flanking region and start codon of each of the *T. aestivum* genes were aligned, and used for a pair wise comparison (see FIG. 4).

The *T. aestivum* PAPhy phytase gene (in λ clone TaG2) and the PCR amplicon obtained from amplifying genomic DNA from the same cultivar, Skagen, had the same nucleotide sequence, and are included in FIG. 4. The nucleotide sequence of the 1000 bp 5' flanking promoter region of each of the *T. aestivum* genes share at least 99.7% identity, whereas the nucleotide sequence of the corresponding promoter regions from two HighPhy cultivars only share 97.7-98.1% sequence identity to the other *T. aestivum* genes. The nucleotide sequence of the promoter regions of the two HighPhy cultivars [SEQ ID NO: 5 and 6], however, share 99.8% sequence identity with each other, differing in nucleotide sequence by only two base pairs. A polynucleotide comprising a ~2000 bp promoter region from the HighPhy cultivars, corresponding to the promoter region of the wild type *T. aestivum* PAPhy phytase gene, has the nucleotide sequence (SEQ ID NO: 44).

3.3 Characterization of the Promoter Region of Isolated *T. Aestivum* and *T. tauschii* Phytase Genes—Alignment of 288 bp The 288 bp 5' flanking region and start codon of each of the *T. aestivum* genes together with the corresponding sequence from *T. tauschii* were aligned, and used for a pair wise comparison (FIG. 5).

The amplified 288 bp 5' flanking promoter region from each of: wild-type *T. aestivum* cultivars; HighPhy *T. aestivum* cultivars; and *T. tauschii* cultivars shared nucleotide sequence identity within each of the three groups. However, the nucleotide sequence of the promoter regions of the two HighPhy *T. aestivum* cultivars differs from the wild-type 9 *T. aestivum* cultivars in two nucleotides, and differs from the two *T. tauschii* cultivars in 3 nucleotides. In turn the nucleotide sequence of the promoter regions from the two *T. tauschii* cultivars differs from wild-type *T. aestivum* cultivars in 3 nucleotides.

It can be seen from the alignment in FIG. 6, that the 5' flanking promoter region of the two HighPhy *T. aestivum* cultivars [SEQ ID NO: 5] comprises a single nucleotide polymorphism (SNP) (−244 T→C), that is unique to these HighPhy cultivars, when compared to the wild type cultivars [SEQ ID NO: 7 and 8].

EXAMPLE 4

Genomic Context of the SNP in HighPhy *T. aestivum* Cultivars

Sequence analyses of the immediate surroundings of the HighPhy SNP reveals sequence motifs known to be involved in gene regulation. Consider first the sequence found in wild type *T. aestivum* (wheat) cultivars (wt):

AACATGA*GTCAT*GCATGGGA        [SEQ ID NO: 4]

It consists of four overlapping motifs:
  In bold font, the odd base palindrome sequence reported by [3];
  In enlarged font, GCN4 motif, involved in endosperm specific gene expression [4];
  In italic font, the skn-1 motif reported by [5];
  In underlined font, the palindomic RY-repeat identical to that reported by [6].
Note that the skn-1 and GCN4 motifs are contained within the odd base palindrome. The odd base palindrome and GCN4 motif have been shown to interact with Opaque2, a maize basic leucine zipper (bZIP) transcription factor involved in the regulation of seed storage proteins [3,4], whereas the RY-repeat has been shown to interact with transcription factors containing the B3 domain. It is known to be an enhancer of seed-specific expression and a repressor of vegetative expression in *A. thaliana* [7].

Consider now the Sequence from the Highphy *T. Aestivum* Cultivars:

A<u>ACA</u>^C<u>GAGT</u>CATGCATGGGA        (SEQ ID NO: 63)

The mutation, identified by the elevated "C", abolishes the odd base palindrome and the GCN4 motif, but leaves the skn-1 motif and the RY-repeat unchanged. A new motif, boxed, is thereby introduced. This motif shows similarity to the G-box CACGTG (1) but lacks the highly conserved palindromic nature of the G-box, and represents a completely novel motif, acting as a cis-acting regulatory element. This mutation, found in HighPhy *T. aestivum* cultivars, is either the result of the abolition of the odd base palindrome or the result of the introduction of the novel motif.

EXAMPLE 5

Method for Detecting the HighPhy SNP in the Genome of Cereal Plants

The SNP in the genome of a cereal plant that is located in a polynucleotide comprising the enhancer element having the nucleotide sequence "CGAGTCATGCATGGGA" (SEQ ID NO: 64) was detected using the technique of "High Resolution Amplicon Melting Analysis" [10]. PCR was performed in 10 μL volumes in a LightCycler (Roche Applied Systems) with programmed transitions of 20° C./s unless otherwise indicated. The amplification mixture included 50 ng genomic DNA as template, 200 μM each deoxynucleotide triphosphate (dNTP), 0.4 U KlenTaq1 polymerase (ABPeptides), 88 ng TaqStart antibody (ClonTech), 3 mM MgCl2, 50 mM Tris (pH 8.3), 500 ng/μL bovine serum albumin, 0.5 μM primers located upstream and downstream of the SNP and 1-10 μM LCGreen, in order to amplify an polynucleotide of around 40-300 nucleotides in length. Melting analysis was performed on the LightCycler. After amplification, the samples are heated momentarily in the LightCycler to 94° C. and cooled to 40° C. The LightCycler capillary is then transferred to the high-resolution melting instrument and heated at 0.3° C./s. Sample temperature and fluorescence signals are converted to 16-bit digital signals, which are then analysed to detect the SNP.

EXAMPLE 6

Method for Inducing and Selecting Wheat Germplasm Comprising the HighPhy SNP and Grain with High Levels of the Enzyme Phytase HighPhy wheat can be generated by mutagenesis and subsequent screening for individuals where the polynucleotide TGAGTCATGCATG (SEQ ID NO: 65), corresponding to the wild type (NormPhy) element, in the wheat genome has been converted into the mutant (HighPhy) element CGAGTCATGCATG (SEQ ID NO: 66). The mutagenesis is carried out with sodium azide which preferentially generates A:T to G:C substitutions in barley (8). Screening mutagenized populations for the desired mutation could be done by allele specific polymerase chain reaction (AS-PCR).

Procedure: Wheat grains are presoaked for 15 hours in demineralised water at 5° C. and then treated with an oxygenated solution of 1 mM sodium azide at pH 3 for 2 hours. The grains are washed and sown out, and grown to mature plants. Genomic DNA is isolated from leaves of each individual plant before the plant begins to senesce, using a standard DNA extraction procedure [9], whereas grains are harvested at maturity. Grains from individual plants are kept apart and labelled so they can be matched with the corresponding DNA isolates. The DNA isolates are screened by AS-PCR using the following primer pair:

```
                        [SEQ ID NO: 37]
HighPhy Fw:    5'CAAGCTACACTTTGTAGAACAC 3'

[SEQ ID NO: 38]
PAPhy Rv:      5'CGCTGCACCCGGGGGTCCGT 3'
```

The first 21 nucleotides of the HighPhy Fw primer anneal 5' to the HighPhy enhancer polynucleotide, whereas the 3'C nucleotide anneals to the actual SNP, this SNP being the distinguishing nucleotide between the HighPhy and NormPhy element polynucleotides. The PAPhy Rv primer anneals to a highly conserved part of the coding sequence of the PAPhy phytase gene, and can thus be expected to anneal to all known loci in the genome containing the wheat PAPhy phytase gene. The AS-PCR is performed using a non-proofreading polymerase to ensure specificity, and detection of the SNP. A series of replicate AS-PCR, using the HighPhy Fw primer and PAPhy Rv primer pair, are performed under conditions of increasing stringency (e.g. increasing PCR annealing temperature), on control genomic DNA samples isolated from HIGHPHY01 wheat grain of the invention and a wildtype NormPhy wheat plant. Under selected conditions of stringency, AS-PCR is then performed on DNA isolated from HighPhy mutation positive plants to amplify an amplicon of 300 to 700 bp in length, which can be identified by agarose gel electrophoresis, whereas plants lacking the HighPhy mutation will not produce an amplicon. The amplified product is then cloned and sequenced to confirm that the presence of the mutant (HighPhy) element CGAGTCATGCATG (SEQ ID NO: 66) in the genomic DNA isolate. AS-PCR conditions that are sufficiently stringent to selectively amplify HighPhy mutation positive plants, are then employed to screen genomic DNA isolated from each individual mutagenized plant. Grain from HighPhy mutation positive plants can then be cultivated further to generate sufficient grain for subsequence breeding and crop production.

EXAMPLE 7

Phytase Activity of Different *Secale cereale* Cultivars 7.1 Comparative Levels of Total Phytase Enzymatic Activity in Mature *Secale cereale* (Rye) Grain The phytase activity was measured in mature seeds of 5 individual cultivars rye, as described for seeds of *Triticum aestivum*, detailed in Example 1.1. Phytase activity ranged from ~1600 to ~6000 FTU/kg in grain from the 5 rye line (FIG. 8). In one line, LPPO3, the level of phytase activity was ~1600 FTU/kg, which was lower than levels measured in the other 4 lines, of which one line had ~6000 FTU/kg.

EXAMPLE 8

Amplification and Characterization of Phytase Gene Promotors from Different *Secale cereale* and *Hordeum vulgare* Cultivars 8.1 Isolation of Phytase Gene Promoters by PCR Genomic DNA was isolated from *Secale cereale* and *Hordeum vulgare* cultivars and the phytase gene promoter was amplified by PCR as described in Example 3.1.

EXAMPLE 9

Structural Characterisation of Cereal Phytase Enzymes and the Coding Sequence of their Cognate Genes The promoter of the invention comprising an enhancer polynucleotide having SEQ ID NO: 1 or 2, is structurally and operably linked to a polynucleotide molecule comprising a coding sequence encoding a phytase enzyme. The polynucleotide molecule in the genome of a cereal plant encoding a phytase enzyme comprises a coding sequence (comprising one or more exon) and a non-coding sequence (comprising one or more intron). The amino sequence and the nucleotide sequence of the coding sequence encoding a phytase enzyme derived from the *Triticum aestivum* cv., (Ta); *Secale cereale* cv., (Sc); and *Hordeum vulgare* cv., (Hv) are as follows:

TaPAPhy_a1 phytase (SEQ ID NO: 18) encoded by TaPAPhy_a1 cDNA (SEQ ID NO: 17);
TaPAPhy_a2 phytase (SEQ ID NO: 20) encoded by TaPAPhy_a2 cDNA (SEQ ID NO: 19);
TaPAPhy_a3 phytase (SEQ ID NO: 22) encoded by TaPAPhy_a3 cDNA (SEQ ID NO: 21);
TmPAPhy_a4 phytase (SEQ ID NO: 24) encoded by TmPAPhy_a4 cDNA (SEQ ID NO: 23);
ScPAPhy_a1 phytase (SEQ ID NO: 26) encoded by ScPAPhy_a1 cDNA (SEQ ID NO: 25);
ScPAPhy_a2 phytase (SEQ ID NO: 28) encoded by ScPAPhy_a1 cDNA (SEQ ID NO: 26);
HvPAPhy_a1 phytase (SEQ ID NO: 30) encoded by HvPAPhy_a1 cDNA (SEQ ID NO: 29);

The phytase enzyme in mutant HighPhy *Triticum aestivum* has an amino acid sequence similar to the phytase enzyme in wild type *Triticum aestivum* cv's Bobwhite and Skagen. Their amino acid sequences differ by the deletion of three amino acid residues and the substitution of three residues in the HighPhy cultivar when compared to cv's Bobwhite and Skagen, these differences being located within the 120 residue long signal peptide region at the amino-terminus. The substitutions are conservative, G→A and S→T.

EXAMPLE 10

Stability of Phytase Activity in Wheat Flour Subjected to Steam Treatment

Animal feed comprising milled cereal grain, is commonly subjected to steam pelleting, which is a two-step process of conditioning followed by pelleting. During conditioning the milled feed is mixed and simultaneously heated to about 80° C. and its moisture content is increased by exposure to steam. The experimental set up used in this example simulates the combination of heat and moisture used during conditioning.

The experimental setup consisted of a GFL 1083 water bath with a plastic tray floating on the surface of the water and occupying approximately half of the surface area of the water. A thermometer, placed inside the tray, was used to monitor the headspace temperature before and after incubation. The water bath was equipped with a thermostat and a lid so a constant temperature and steam-filled headspace with 100% relative humidity could be maintained. The water bath was set to 80° C., and once this temperature was reached, it was allowed to equilibrate for one hour. The headspace temperature was found to be 80° C. at this point.

Eight to nine grams of sample wheat grains were milled on a Retsch RM100 mortar grinder mill, and the resulting flour was distributed in weighing boats, 500 mg in each. The steam treatment consisted of incubating the weighing boats with samples on the plastic tray for various periods of time. The lid of the water bath remained closed for the duration of the incubation and the temperature of 80° C. in the headspace was verified before and after each incubation. Following steam treatment, the wheat flour samples were dessicated overnight in an exicator with silica gel.

Once dried, the phytase activity of the wheat flour samples was assayed using the assay described by (Engelen, Vanderheeft, Randerheeft & Smidt, 1994 [1])

Two measurements, (A) and (B), of phytase activities of wild type wheat (*T. aestivum* cv. Bobwhite (BW)) and HighPhy (HIGHPHY) wheat, after 0, 10, 20 and 40 min of incubation at 80° C. at 100% relative humidity, are shown in FIG. 9. At t=0, the phytase activities of BW and HIGHPHY were 1286 and 4311 FTU/kg, respectively. After 10 min of incubation, HIGHPHY still exhibited a very substantial phytase activity of 3046 FTU/kg, while BW only exhibited 940 FTU/kg. After 20 min of incubation, HIGHPHY had 1801 FTU/kg residual phytase activity, still higher than the starting level in BW, while in BW the activity was only 667 FTU/kg. The most extreme incubation of 40 min reduced phytase activity in the HIGHPHY to 962 FTU/kg, while levels in BW were reduced to 476 FTU/kg.

The experimental conditions used to test phytate stability were more extreme than those of commercial steam-pelleting, where the duration of steam treatment of normally around 1 minute. It is thus expected that the residual phytase activity in pelleted feed made from HighPhy cereal grains of the invention will lie above the level at which supplementary phytase is required (circa 2500 FTU/kg).

EXAMPLE 11

Stability of Phytase Activity in HighPhy *Secale cereale* (Rye) Subjected to Steam Treatment Grain of HighPhy rye were milled and the resulting flour was subjected to simulated conditioning, using the same experimental set up as used for wheat flour in example 10.

A single measurement of phytase activity of HighPhy rye, after 0, 1, 2, 3, 4, 5, 10, 30, 45 and 60 min of incubation at 80° C. at 100% relative humidity, are shown in FIG. 10. At t=0, the phytase activities of HighPhy rye was 4013 FTU/kg, and after 10 min still exhibited a very substantial phytase activity of 3818 FTU/kg. After 30 min of incubation phytase activities in the flour dropped to 1746 FTU/kg.

EXAMPLE 12

Enhanced Phytate Degradation in High-Phy Wheat Flour

Phytase degradation during fermentation of dough improves its nutritional and bread-making quality, since phytase degradation enhances inorganic phosphate levels and mineral content in bread, and is known to improve dough mixing quality. Dough made from HighPhy wheat is shown to provide these advantages.

Wild type wheat (*T. aestivum* cv Bobwhite (BW)) and HighPhy wheat (HP) grains were milled on a Retsch RM100 mortar grinder mill. The phytate content in the resulting flour was determined using the procedure described by (Vaintraub & Lapteva, 1988). Flour (250 mg) was mixed with 0.1 ml of bakers yeast water stock (dry yeast in 3 mg/ml water). An additional 0.2 ml of water was added to form a dough. The dough was fermented at 25° C. for 0.5, 1, 3 and 3 hrs. After fermentation, the phytate content was determined again, using the same procedure (Vaintraub and Lapteva, 1988).

Figure 12:
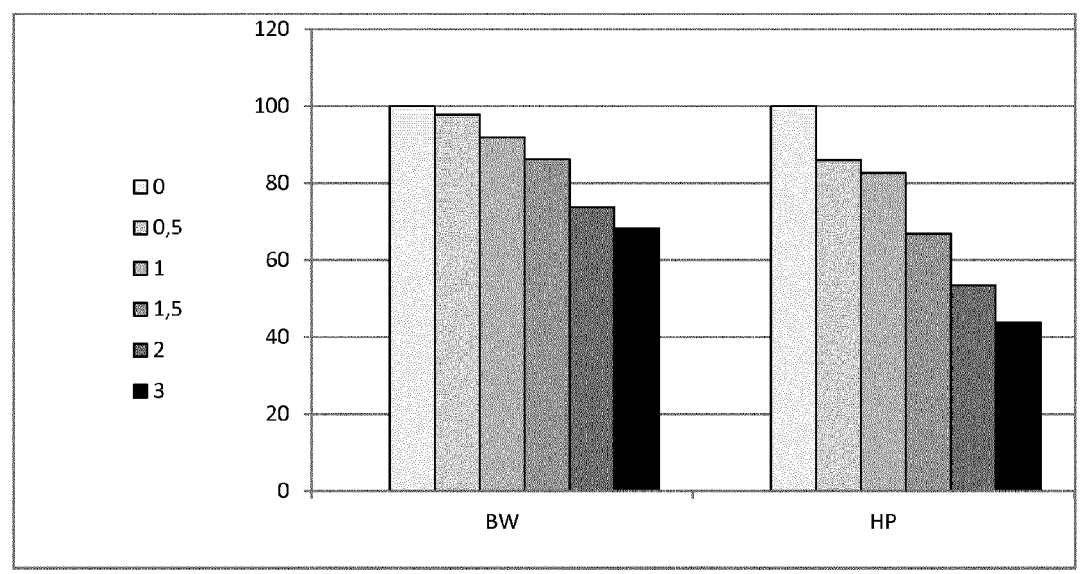

The initial phytate content of HP wheat flour was a little higher than that of BW wheat (FIG. 11). However during fermentation, phytate levels were decreased to a lower level in flour from HP than BW wheat. Thus, phytate levels were reduced significantly more during fermentation in wheat dough from HP in comparison to dough from BW, both in terms of percentage and in the final phytate levels. Already after 0.5 hr, phytate was reduced more in HP than in BW wheat (FIG. 12 and table 2). After 3 hrs, only ~44% of the initial phytate was left in the HP wheat, whereas ~68% was left in the wild type BW wheat.

TABLE 2

Percent residual phytate (IP6) in dough of wild-type (BW) and HighPhy (HP) wheat flour

| Time | BW residual IP6 (%) | HP residual IP6 (%) |
|---|---|---|
| 0 | 100 | 100 |
| 0.5 | 97.8 | 85.9 |
| 1.0 | 91.9 | 82.7 |
| 1.5 | 86.2 | 66.9 |
| 2.0 | 73.8 | 53.6 |
| 3.0 | 68.3 | 43.8 |

EXAMPLE 13

The HighPhy Enhancer in the Barley Phytase Gene Confers Both Aleurone and Endosperm-specific Expression in Developing Barley Grain 13.1 Cloning of Promoter-GUS Constructs for Examination of the HighPhy Mutation:

The HighPhy Mutation was Introduced in the pCLEAN-G185-PAPhy_a Construct with the Mutagenic Primers:

```
                                    (SEQ ID No. 46)
HvPAPhy_a SDmut Fw    5'GTAGAACACGAGCCATGCATGAGAC3'

(SEQ ID No. 47)
HvPAPhy_a SDmut Rv    5'TGGCTCGTGTTCTACAAAATGTAGC3'
```

This yielded the pCLEAN-G185-HP-PAPhy_a construct.

The two constructs pCLEAN-G185-PAPhy_a and pCLEAN-G185-HP-PAPhy_a were further modified to serve as promoter-reporter gene constructs. To achieve this, the PAPhy_a coding open reading frame and terminator was replaced by the UidA open reading frame followed by the NOS terminator. The cloning was performed with the "In-Fusion" technology as described in (Zhu, Cai, Hall and Freeman, 2007). This approach ensured seamless joining of the promoter and reporter gene so the start codon context was preserved.

The vector backbone and promoter of both constructs were amplified using the primers:

```
                                        (SEQ ID No. 48)
Cis to GUS Fw    5' TCGAGTCGACGTTCCTTGAC3'

(SEQ ID No. 49)
Cis to GUS Rv    5' GTTGATGTTGTTGCTTGGCATTG3'
```

The UidA and NOS terminator were amplified from pGUSN which is a pUC18 plasmid comprising an UidA gene and a downstream NOS terminator, using the primers:

```
GUS Fw m. overhang
                                        (SEQ ID No. 50)
5' AGCAACAACATCAACATGTTACGTCCTGTAGAAACC3'

GUS Rv m. overhang
                                        (SEQ ID No. 52)
5' GGAACGTCGACTCGACTATGACCATGATTACGAATTCC3'
```

Performing the In-Fusion with the resulting amplicons gave the two GUS reporter constructs, pCLEAN-G185-wt-proGUS (SEQ ID No. 52) and pCLEAN-G185-HP-proGUS (SEQ ID No. 54).

13.2: Constructing Randomized Phytase Gene Enhancer Element Sequences to Confirm the Criticality of the Promoter Enhancer Element Comprising the HighPhy Mutation.

The enhancer element motifs surrounding the HighPhy mutation were removed by sequence randomization by taking the 20 bp corresponding to SEQ ID 4 in the pCLEAN-G185-PAPhy_a construct and subjecting the sequence to a nucleotide randomizer world wide web at molbiol.ru/eng/scripts/01_16.html using settings designed to preserve the nucleotide ratios of the original sequence. The resulting sequence, 5' gcatacgaagcatagtacga3', was only identical to the original in three nucleotide positions and did not contain any regulatory elements known by PlantCARE*. The original 20 bp in pCLEAN-G185-wt-proGUS was replaced by the randomized sequence as described by Zhu and co-workers using the primers:

```
Kill triad Fw
                                        (SEQ ID No. 56)
5' gcatacgaagcatagtacgaCGTAGGCGTCCAAACTTTG3';

Kill triad Rv
                                        (SEQ ID No. 57)
5'
tcgtactatgcttcgtatgcCTACAAAATGTAGCTTGAAATTAAAGAG3'

(SEQ ID No. 58)
The resulting construct was pCLEAN-G185-

KOtriad-proGUS.
```

13.3 Transient Expression in Developing Barley Endosperm and Aleurone:

The three constructs were individually introduced into developing (from 14 to 35 days after pollination) barley endosperm and aleurone cells by particle gun bombardment. Immature barley seeds were sterilized, and cultured on media and bombarded in a DuPont PDS 1100 helium biolistic delivery system using the procedures described in (BrinchPedersen, Galili, Knudsen, & Holm, 1996). Expression of the uidA gene was assayed in the plant tissues two days after bombardment, using the gus reaction buffer, as described in Jefferson, Kavanagh, & Bevan, 1987. Gus expression was scored by localizing blue spots on the bombarded tissues.

In tissues bombarded with the pCLEAN-G185-wt-proGUS plasmid, blue spots were mainly identified in the aleurone layers, with very limited expression in the endosperm. In pCLEAN-G185-HP-proGUS bombarded tissues more expression could be observed in the endosperm tissue. No expression was detected in grain bombarded with the pCLEAN-G185-KOtriad-proGUS. These data confirm that the HighPhy mutation in the context of the barley phytase gene enhancer confers both aleurone and endosperm-specific expression

EXAMPLE 14

Identification of the Wild Type Locus in the Wheat Genome Corresponding to the HighPhy Phytase Gene The mutant gene was aligned to the three homeologous PAPhy_a genes from the wild type cultivar "Chinese spring". The alignment was adjusted to include only the exons and introns of the gene. An UPGMA tree was generated with 1000 bootstrap replications (FIG. 13). The tree clearly points to TaPAPhy_a1 as the wild type locus corresponding to the HighPhy gene.

14.1 Chromosomal Mapping of the TaPAPhy_a1 Gene:

Wheat chromosomal mapping was performed using the Chinese Spring nullisomic-tetrasomic lines described by (Kimber & Sears, 1979. There are 42 possible nullisomic-tetrasomic lines, of which two were missing in the present set of lines (the nullisomic (N) 2A tetrasomic (T) 2B and the N4BT4D lines), but their absence did not compromise the mapping. The following primers where designed to specifically amplify a 522 basepair segment of the TaPAPhy_a1 gene:

```
                                        (SEQ ID NO: 60)
Forward 5'GAGATTCCGAGACCAACGAA3'

(SEQ ID NO: 61)
Reverse 5'TTTGCCTCCACTCTGCCTAC3'
```

The amplicon was exclusively absent from two lines nulisomic for chromosome 5D and tetrasomic for chromosome 5A and 5B respectively (N5DT5A and N5DT5B). Thus, TaPAPhy_a1 maps to chromosome 5D.

LITERATURE CITED

[1] Engelen A J, Heeft F C yen der, Randsdorp P H G, Smit E L C (1994) Simple and rapid determination of phytase activity. J AOAC Internat 77: 760-764.

[2] Eeckhout W, Depaepe M (1994) Total phosphorus, phytate-phosphorus and phytase activity in plant feedstuffs. Anim Feed Sci Tech 47: 19-29.

[3] Depater S, Katagiri F, Kijne J, Chua N H (1994) Bzip Proteins Bind to A Palindromic Sequence Without An Acgt Core Located in A Seed-Specific Element of the Pea Lectin Promoter. Plant Journal 6: 133-140

[4] Wu C Y, Suzuki A, Washida H, Takaiwa F (1998) The GCN4 motif in a rice glutelin gene is essential for endosperm-specific gene expression and is activated by Opaque-2 in transgenic rice plants. Plant Journal 14: 673-683

[5] Blackwell T K, Bowerman B, Priess J R, Weintraub H (1994) Formation of A Monomeric Dna-Binding Domain by Skn-1 Bzip and Homeodomain Elements. Science 266: 621-628

[6] Baumlein H, Nagy I, Villarroel R, Inze D, Wobus U (1992) Cis-Analysis of A Seed Protein Gene Promoter—the Conservative Ry Repeat Catgcatg Within the Legumin Box Is Essential for Tissue-Specific Expression of A Legumin Gene. Plant Journal 2: 233-239

[7] Fujiwaraa, T., Nambara, E., Yamagishi, K., Goto, D. B., Naito, S. (2002) Storage Proteins. The *Arabidopsis* Book, 2002 American Society of Plant Biologists.

[8] Olsen, O., et al. Proc. Natl. Acad. Sci. USA (1993) Vol. 90, pp. 8043-8047.

[9] Sambrook, Fritsch and Maniatis (2001) Molecular Cloning: A Laboratory Manual ($2^{nd}$ Edition) Cold Spring Harbor Laboratory Press.

[10] Wittwer, C. T., et al., (2003) High resolution genotyping by amplicon melting analysis using LCgreen Clinical Chemistry: 49:6 853-860.

BrinchPedersen, H., Galili, G., Knudsen, S., & Holm, P. B. (1996). Engineering of the aspartate family biosynthetic pathway in barley (*Hordeum vulgare* L) by transformation with heterologous genes encoding feed-back-insensitive aspartate kinase and dihydrodipicolinate synthase. *Plant Molecular Biology*, 32(4), 611-620.

Engelen, A. J., Vanderheeft, F. C., Randsdorp, P. H. G., & Smit, E. L. C. (1994). Simple and Rapid-Determination of Phytase Activity. *Journal of Aoac International*, 77(3), 760-764.

Jefferson, R. A., Kavanagh, T. A., & Bevan, M. W. (1987). GUS FUSIONS-BETA-GLUCURONIDASE AS A SENSITIVE AND VERSATILE GENE FUSION MARKER IN HIGHER-PLANTS. *Embo Journal*, 6(13), 3901-3907. Kimber, G., & Sears, E. G. (1979). Use of wheat aneuploids. *Basic Life Sciences*, 13, 427.

Vaintraub, I. A., & Lapteva, N. A. (1988). COLORIMETRIC DETERMINATION OF PHYTATE IN UNPURIFIED EXTRACTS OF SEEDS AND THE PRODUCTS OF THEIR PROCESSING. *Analytical Biochemistry*, 175(1), 227-230. doi: 10.1016/0003-2697(88)90382-x Zhu, B. G., Cai, G. F., Hall, E. O., & Freeman, G. J. (2007). In-Fusion™ assembly: seamless engineering of multidomain fusion proteins, modular vectors, and mutations. *Biotechniques*, 43(3), 356-359. doi: 10.2144/000112536

PlantCARE, a database of plant cis-acting regulatory elements and a portal to tools for in silico analysis of promoter sequences:

MAGALI Lescot, Patrice Déhais, Gert Thijs, Kathleen Marchal, Yves Moreau, Yves Van de Peer, Pierre Rouzé and Stephane Rombauts *Nucleic Acids Res.* 2002 Jan. 1;30(1): 325-327

The invention claimed is:

1. A method for producing a *Triticum* plant capable of producing an average phytase endosperm content of greater than 4300 FTU/kg, said method comprising:
   a) obtaining a sample of nucleic acids from a *Triticum* plant or portion thereof;
   b) detecting in said sample the presence of the nucleotide V at the 5' end of a polynucleotide having the nucleotide sequence ACA VGA GTC ATG CAT (SEQ ID NO:1), wherein V is a cytosine;
   c) breeding a *Triticum* plant comprising said nucleotide sequence with a second *Triticum* plant to obtain grains; and
   d) growing at least one *Triticum* plant from said grains; wherein said *Triticum* plant grown from said grains comprises said nucleotide V at the 5' end of a polynucleotide having the nucleotide sequence ACA VGA GTC ATG CAT (SEQ ID NO: 1), and wherein said V is a cytosine.

2. The method according to claim 1, wherein said sample of nucleic acids comprises a first polynucleotide located 5' upstream of and operably linked to a second polynucleotide, wherein said first polynucleotide comprises the nucleotide sequence ACA VGA GTC ATG CAT (SEQ ID NO:1), wherein V is a cytosine, and wherein said second polynucleotide encodes a phytase polypeptide having myo-inositol hexakisphosphate phosphohydrolase activity.

3. The method according to claim 1, wherein a population of *Triticum* plants grown from said grains have an average phytase grain content of greater than 4300 FTU/kg.

4. The method of claim 1 wherein said polynucleotide is operably linked to a phytase encoding sequence.

* * * * *